(12) United States Patent
Gittes et al.

(10) Patent No.: US 10,071,172 B2
(45) Date of Patent: Sep. 11, 2018

(54) ENDOGENOUS NEOGENESIS OF BETA CELLS

(71) Applicant: University of Pittsburgh—Of the Commonwealth System of Higher Education, Pittsburgh, PA (US)

(72) Inventors: George Gittes, Pittsburgh, PA (US); Ping Guo, Cheswick, PA (US); Xiangwei Xiao, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/305,083

(22) PCT Filed: Apr. 17, 2015

(86) PCT No.: PCT/US2015/026532
§ 371 (c)(1),
(2) Date: Oct. 18, 2016

(87) PCT Pub. No.: WO2015/164218
PCT Pub. Date: Oct. 29, 2015

(65) Prior Publication Data
US 2017/0087254 A1    Mar. 30, 2017

Related U.S. Application Data

(60) Provisional application No. 61/983,295, filed on Apr. 23, 2014.

(51) Int. Cl.
*C12N 7/00* (2006.01)
*A61K 48/00* (2006.01)
*A61K 38/17* (2006.01)

(52) U.S. Cl.
CPC ...... *A61K 48/0075* (2013.01); *A61K 38/1709* (2013.01); *A61K 48/0058* (2013.01); *C12N 7/00* (2013.01); *C12N 2750/14143* (2013.01)

(58) Field of Classification Search
CPC .............. A61K 38/1709; A61K 48/005; A61K 48/0058; A61K 48/0075; C12N 7/00; C12N 2750/14111; C12N 2750/14141; C12N 2750/14143
See application file for complete search history.

(56) References Cited

U.S. PATENT DOCUMENTS

| | | | | |
|---|---|---|---|---|
| 2002/0058640 A1* | 5/2002 | Abrams | ............... | A61K 9/0024 514/44 A |
| 2009/0280096 A1* | 11/2009 | Kubo | ............... | C07K 14/4705 424/93.7 |
| 2010/0137202 A1* | 6/2010 | Yang | ............... | A61K 48/005 514/21.5 |
| 2011/0065100 A1* | 3/2011 | Aldred | ............... | C12Q 1/6883 435/6.14 |
| 2011/0280842 A1 | 11/2011 | Melton | | |
| 2012/0071544 A1* | 3/2012 | Chen | ............... | A61K 31/7088 514/44 R |

FOREIGN PATENT DOCUMENTS

WO    WO 2010/022395 A2    2/2010

OTHER PUBLICATIONS

Skarnes et al, GenBank JN948751, 2011.*
Zhou et al, Nature 455:627-633, 2008.*
Taniguchi et al, Gene Therapy 10:15-23, 2003.*
Collombat et al, Cell 138:449-462, 2009.*
Chen et al, Molecular Therapy-Nucleic Acids 2(e85):pp. 1-10, Apr. 9, 2013; doi:10.1038/mtna.2013.15.*
Jimenez et al, Diabetologia 54:1075-1086, 2011.*
Loiler et al, Molecular Therapy 12(3):519-527, 2005.*
Rambow et al, Z. Gastroenterol. 26(5):279-282, 1988; abstract only.*
Aguayo-Mazzucato et al., "Mafa expression enhances glucose-responsive insulin secretion in neonatal rat beta cells," *Diabetologia* 54(3): 583-593 (Mar. 2011).
Banga et al., "Stable insulin-secreting ducts formed by reprogramming of cells in the liver using a three-gene cocktail and a PPAR agonist," *Gene Therapy* 21: 19-27 (published online Oct. 3, 2013).
Guo et al., "Rapid and simplified purification of recombinant adeno-associated Virus," *J. Virol. Methods* 183(2): 139-146 (Aug. 2012).
Guo et al., "Specific transduction and labeling of pancreatic ducts by targeted recombinant viral infusion into mouse pancreatic ducts," *Laboratory Investigation* 93: 1241-1253 (published online Oct. 7, 2013).
International Search Report from parent PCT Application No. PCT/US2015/026532, 5 pages (dated Jun. 16, 2015).
Kaneto et al., "Role of PDX-1 and MafA as a potential therapeutic target for diabetes," *Diabetes Research and Clinical Practice* 77S: S127-S137 (2007).

(Continued)

*Primary Examiner* — Kevin K Hill
(74) *Attorney, Agent, or Firm* — Klarquist Sparkman, LLP

(57) ABSTRACT

Methods are disclosed for producing pancreatic beta cells in a subject. The methods include administering to the subject a vector encoding heterologous Pancreas duodenal homeobox protein (Pdx) 1 and MafA, wherein the vector does not encode Neurogenin 3 (Ngn3) and wherein the subject is not administered any other nucleic acid encoding Ngn3. The vector is administered intraductally into a pancreatic duct of the subject. Compositions are disclosed that include a) a viral vector comprising a promoter operably linked to a nucleic acids encoding Pdx1 and a nucleic acid encoding MafA, wherein the vector does not encode Ngn3; b) a buffer; and c) a contrast dye for endoscopic retrograde cholangiopancreatography. These compositions are of use in any of the methods disclosed herein.

22 Claims, 25 Drawing Sheets
Specification includes a Sequence Listing.

(56) References Cited

OTHER PUBLICATIONS

Miyashita et al., "Sequential introduction and dosage balance of defined transcription factors affect reprogramming efficiency from pancreatic duct cells into insulin-producing cells," *Biochemical and Biophysical Research Communications* 444: 514-519 (Jan. 2014).
Wang et al., "Comparison of adenoviral and adeno-associated viral vectors for pancreatic gene delivery in vivo," *Human Gene Therapy* 15:405-413 (Apr. 2004).
Written Opinion from parent PCT Application No. PCT/US2015/026532, 4 pages (dated Jun. 16, 2015).
Xiao et al., "Neurogenin3 activation is not sufficient to direct duct-to-beta cell transdifferentiation in the adult pancreas," *J. Biol. Chem.* 288(35): 25297-25308 (Aug. 30, 2013).
Zhou et al., "In vivo reprogramming of adult pancreatic exocrine cells to β-cells," *Nature* 455: 627-633 (Oct. 2, 2008).

* cited by examiner

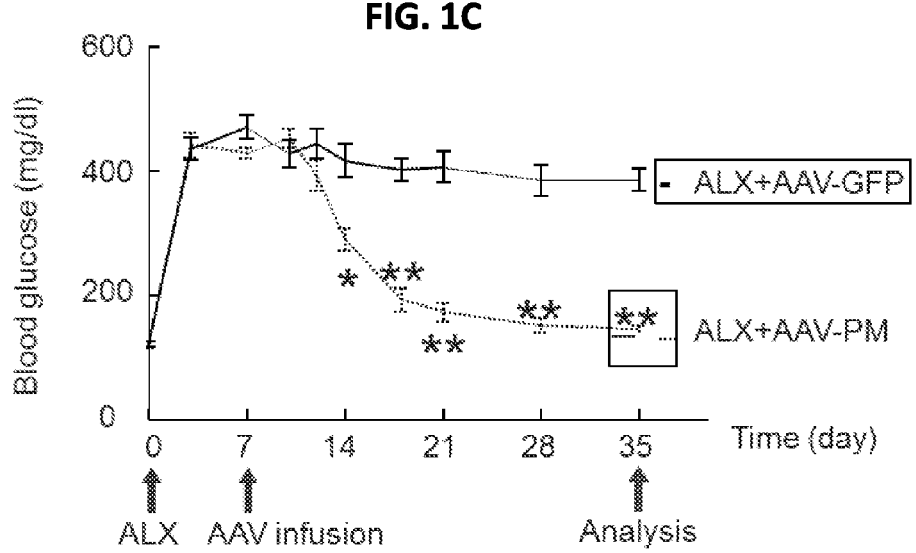
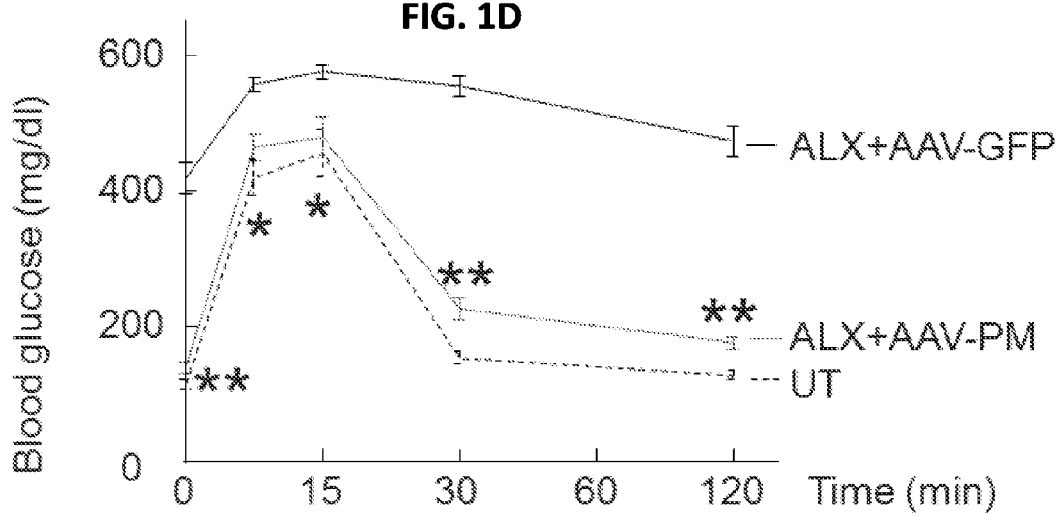

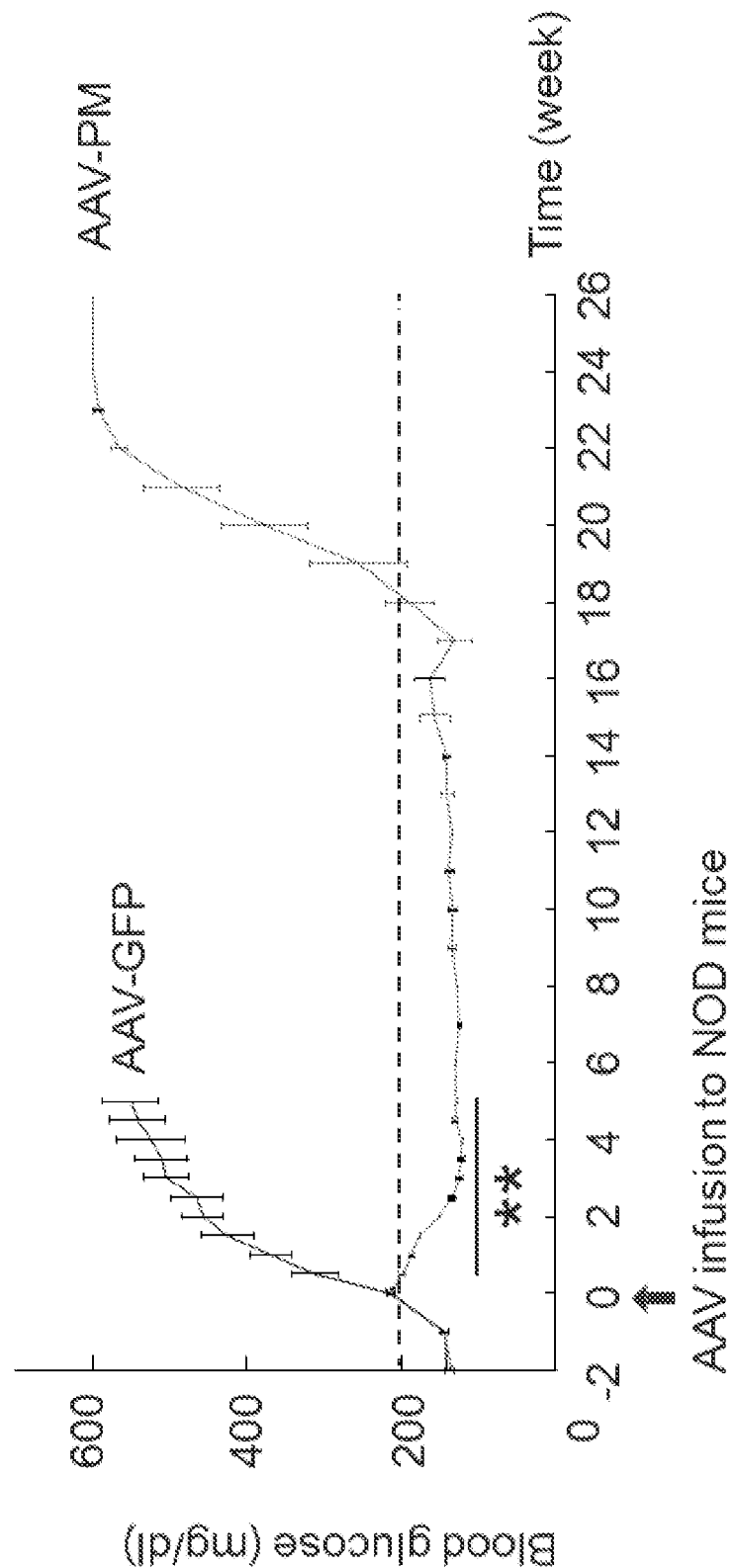

300 NOD/SCID islets
↓ kidney capsule
NOD/SCID
NOD AAV-GFP 2w
NOD AAV-PM 2w

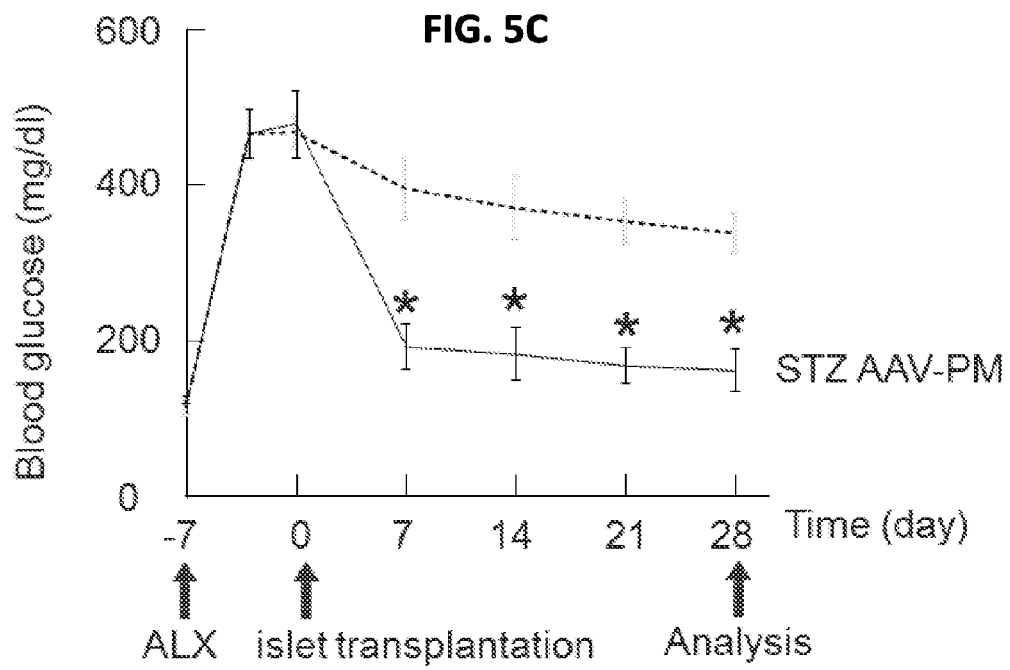
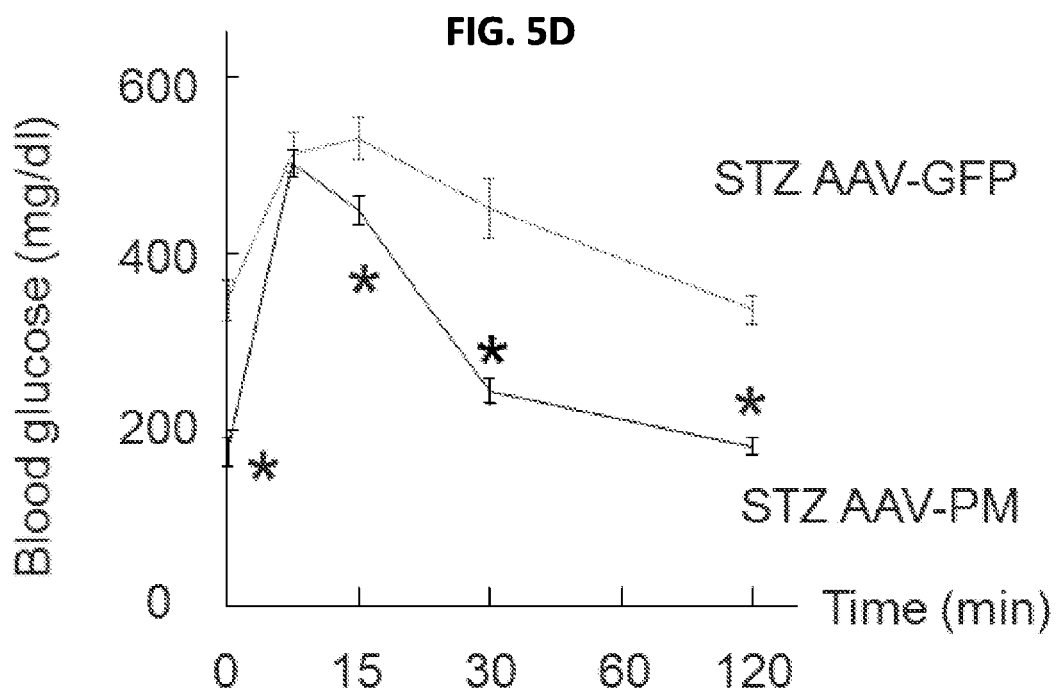

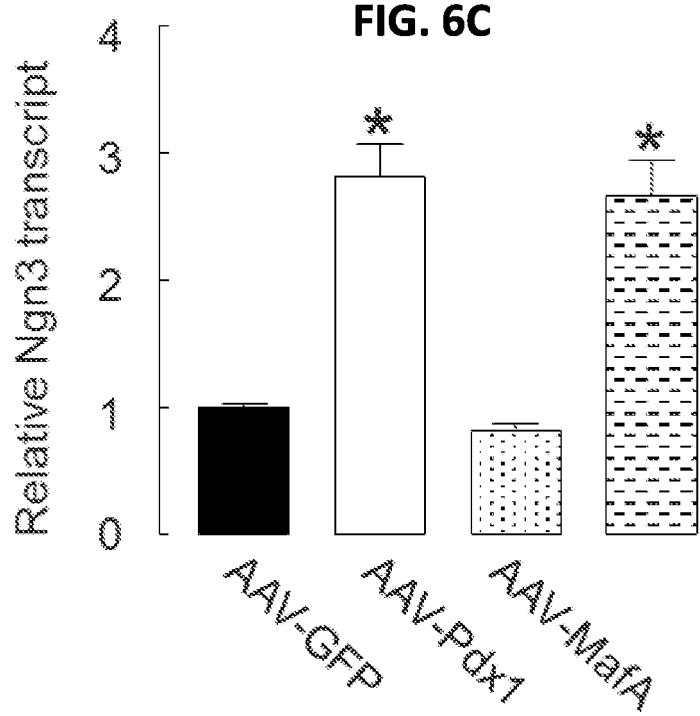
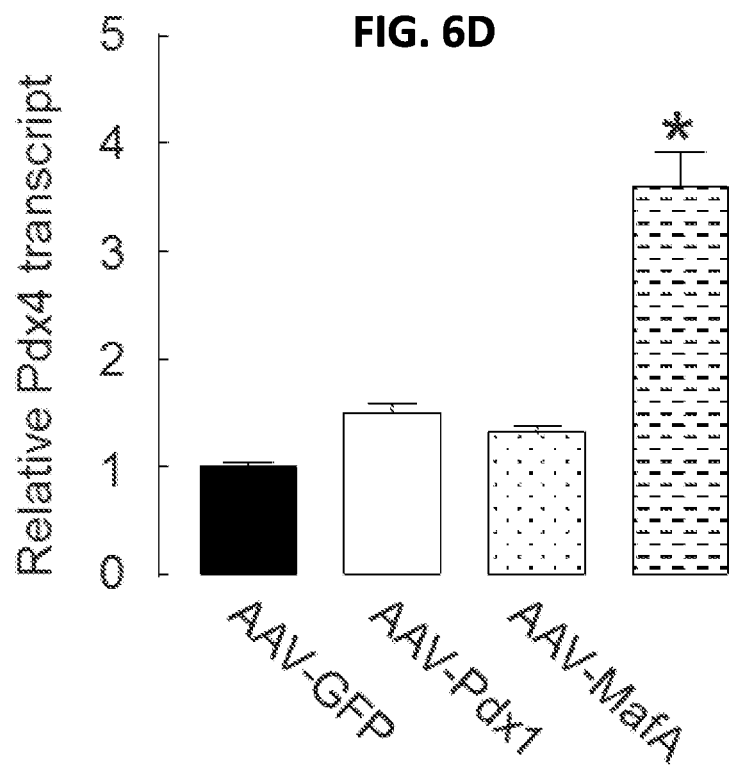

from AAV-PM treated GCG-Cre;
R26R^Tomato islets (new beta cells)

SEQUENCE LISTING

```
<160> NUMBER OF SEQ ID NOS: 17

<210> SEQ ID NO 1
<211> LENGTH: 459
<212> TYPE: DNA
<213> ORGANISM: Homo sapiens

<400> SEQUENCE: 1
aaaaaatacc agataatttc ctgttagcat cagctatctt ggatgtttaa tcttcatttt      60
gctccatcct ttctgcctga attccattta ttaaaacaga acacataggg gtttaatcaa     120
tatccttaaa ttttccacaa acataacata aataaactcc acgttgtgag gaagagagga     180
tttttaatac atatgtgttg aatgaatgat cattatttag ataaatgaat gactgaagtg     240
attgttatat tcaggtaaat tcatcatggc taggtagcaa accaaagact tgtaagaacc     300
tcaaatgagg acatgcacaa aacagggatg gccatgggct acgtaatttc aaggtctttt     360
gtcttcaacg tcaaaattca ctttagagaa cttaagtgat tttcatgcgt gattgaaagt     420
agaaggtgga tttccaagct gctctctcca ttcccaacc                            459

<210> SEQ ID NO 2
<211> LENGTH: 1243
<212> TYPE: DNA
<213> ORGANISM: Homo sapiens

<400> SEQUENCE: 2
tcagtgacat catgcggttg gttatattag aatattggaa tctagttagg aaatgttgtg      60
atgagtttgc aatatggaat aaaattttta ttttagaaaa gacatttacc aaccccctctc    120 attttacaaa taaggaggca gagacacaaa gagaatgcgt gacttgacca aggtcacaca     180
gctggtcaat aacagcaaaa ctaaaatcaa attatgccaa cactacttct tatgctgtct     240
ttccagatta tttaccattt ttctatttct ctacagtgac cagaatcatt tctgctaaat     300
gtcacagatc attaaagcct gtgtgtccag tcacaaaact caggaaacgt gaaaatatgc     360
atctcatctc aacagttttc ctcatatctc attcttttgt aacttagtac cccactctct     420
tatcagtaaa attagatttt aaatatatat tagaaggaaa aaaataccag ataatttcct     480
gttagcatca gctatcttgg atgtttaatc ttcattttgc tccatccttt ctgcctgaat     540
tccatttatt aaaacagaac acatagggt ttaatcaata tccttaaatt ttccacaaac      600
ataacataaa taaactccac gttgtgagga agagaggatt tttaatacat atgtgttgaa     660
tgaatgatca ttatttagat aaatgaatga ctgaagtgat tgttatattc aggtaaattc     720
atcatggcta ggtagcaaac caaagacttg taagaacctc aaatgaggac atgcacaaaa     780
cagggatggc catgggctac gtaatttcaa ggtcttttgt cttcaacgtc aaaattcact     840
ttagagaact taagtgattt tcatgcgtga ttgaaagtag aaggtggatt tccaagctgc     900
tctctccatt cccaaccaaa aaaaaaaaaa aaagatacaa gagtgcataa aaagtttcca     960
ggtctctaag gtctctcacc caatataagc atagaatgca gatgagcaaa gtgagtggga    1020
```

```
gagggaagtc atttgtaaca aaaactcatt atttacagat gagaaattta tattgtcagc    1080
gtaatatctg tgaggctaaa cagagctgga gagtatataa aagcagtgcg ccttggtgca    1140
gaagtacaga gcttaggaca cagagcacat caaaagttcc caaagagggc ttgctctctc    1200
ttcacctgct ctgttctaca gcacactacc agaaggtaag atg                     1243

<210> SEQ ID NO 3
<211> LENGTH: 461
<212> TYPE: DNA
<213> ORGANISM: Mus musculus

<400> SEQUENCE: 3
gagatatagc caaataccaa atcaagggat aagaccctca aatgagacta ggctcatttg      60
acgtcaaaat tcacttgaga aactttagc agttttcgt gcctgactga gaccgaaggg     120
tggatctcca aactgccctt ccattccca acagaaagg cacaagagta aataaaatgt      180
ttccgggcct ctgcggtctc aacccggtat cagcgtaaaa agcagatgag caaagtgagt     240
gggcgagtga aatcatttga acaaaacccc attatttaca gatgagaaat ttatattgtc     300
agcgtaatat ctgcaaggct aaacagcctg gagagcatat aaaagcacag caccctggtg     360
cagaagggca gagcttgggc ccaggacaca ctcaaagttc ccaaggggac tccctctgtc     420
tacacctgtt cgcagctcag gctcacaagg cagaaaaaaa a                        461

<210> SEQ ID NO 4
<211> LENGTH: 2520
<212> TYPE: DNA
<213> ORGANISM: Homo sapiens

<400> SEQUENCE: 4
tagccaaaaa gtgggaaatt ataacaatac ttgacggccc cacttaggaa aaaaaacagt      60
ccaggtttgg agttaaattt tggggtctga ctggctgtgg ggtttggggc cagtgatttg     120
acatctctga gcagatttca gaccctgaat ctgtaaaatg ggttgttgtg gggatttagt     180
gaggtgactg agctggcagc actttggaaa atgtgaggct ttacaaatga agctggtttt     240
tagcacttcc ttggaatggg ggctctgaga tggggaggga aatggatact ggaaaccggc     300 accccctca acatttcccc tgaacctagg cacatgagtc cattctgcat cctatgcacc      360
caccaaatgg gttctccaa gcctggcacc ccactccttt ccaccttgcc tgaggaccct      420
gaggcccctt ccctcttccc accttgttct agttgcaagc tgcagaggat ggcctgagtt     480
tccattcttc agcctggagg ctctggctgt agcctcagtc ttccagctgc agcctcaatc     540
ttctgcccca agagaatccg ttggatgatt tgggttgatc tttgggaggc aggagagcta     600
gttccaaggc ctgtgaccaa aacctttcag tcactctcga gtcccagaac ccatctttc      660 ttgaaccaag cctgctctgg tgcccaaagg aagggggtgt cagtgatggg ggcccacagg     720
agacttttac tgtggtccag ttttatctgt tatgctgctg gtctggcacc cacagaactg     780
ccctgtcccc ctcccgtctc tggcctcagt actggcgttg ccagtatgag agacagtga      840 gaggagggt gagggcttcg gagtgagaga ggctgacagg aggcggggac tctggggggc     900
tgaggactat aaagcggccc agccgagggc aggggcccat ccggcctgag gcaggtgctc     960
gcttggtcta gtgcccattt actctggact ccgggtaagt gggctcacgc ctgcctgggg    1020
ctctgggggc ctccccagg ctggggcctg ggatggagag gaggtggtgc tttgcagggc    1080
caggggcctt gggaggccta aggtcctgct tgggtcttgc tttctgcatc tggacagacc    1140
tgtcacgcta gaagagccgt ctgctgactg cacgtgtgtg tgcacactcg tgtgcatggc    1200
```

```
ctgtgaactg gaatgtgtga ctgtgacctt gtgagtgaac tggggtccct gtgtgagtgc    1260 cttttgctggt ctgtgcagga cgacatggac aatagcgtct tctccaggac cgatatctgt   1320
gtctctatcg cagggtggag ggccagcacc cacaaggcca tggtttctgt ccttggcttc    1380
ccgagttcat tctgtgtccc ccaccctgtg ggtgacctgc atgcccttat tcccactagc    1440
tgctgcctcc tgggagccat gaggccctag atgtcatcag tcccgtgtct ccaggactca    1500
catccccatt ttaactaact tgcgaggccc tggcttgctg gctgctcac aggacaggct     1560 gtccgtgcct tcagagcagt gtctaggagg tggagtggcc agcttggagt ggccctttgc    1620 tctgcccct tgtccccaag cttggagaaa tggatgatgg gctaaggggc tggatagttg     1680
ggccctgctt cctaggcacg ggaaaatctg caggcccggg cactccacct cccctctgct    1740
tgctcctcag atggctgccg cacgcctctg cctctccctg ctgctcctgt ccacctgcgt    1800
ggctctgtta ctacagccac tgctgggtgc ccagggagcc ccactggagc cagtgtaccc    1860
aggggacaat gccacaccag agcagatggc ccagtatgca gctgatctcc gtagatacat    1920
caacatgctg accaggccta ggtgtgtgcc acagttgggg agagagatcc cagcccctgg    1980
gaccctgggc ccactccaca ttcctggcca caccctatcc ccagccccag ccccagcccc   2040
cttctaggcc tgctcttggg aaacagggca tctgtcgctc aacaggccag accaatgtgc    2100
ctgggcaaga tggtgtccta caggtcagat atgaaacagg tgggctggca cctgggcaca    2160
gtgcttgccc ctgctgcctc ttccctccca ggtatgggaa aagacacaaa gaggacacgc    2220
tggccttctc ggagtggggg tccccgcatg ctgctgtccc caggtgagtt tgactccctg    2280
ccctgtctgt ccaggctccc tggggctgaa atgggggtgg tgggactgaa tcagggcttg    2340
gaaaggtgta gtgggggtg gaagagggag aacaggagcc cagggccagc gtgaggcctc    2400
ctgagggcac gaggcctacc ccctacactg ccatgttctg ccctgtcctc acagggagct    2460
cagcccgctg gacttataat gccaccttct gtctcctacg actccatgag cagcgccagc    2520
```

<210> SEQ ID NO 5
<211> LENGTH: 1243
<212> TYPE: DNA
<213> ORGANISM: Homo sapiens

<400> SEQUENCE: 5

```
gggatcatct cgtccatgct aggaaattag ctggtccttc ctcagtaagg aactatttag    60
ataaaagcag tcagaactct ggcctgaaca gtaaacattt aaccagagtt caatcagaat   120
tcaaggacag gttttcttaa actttctttg tttctaggag atcaggcaga gctgaattta   180
accaagaatc ttttgatcct ttccacatat agatatacaa tagtggtcac atatgttctg   240
ggagttccta gacctatat gtctaaactg gggcttcctg acataaaact atgcttaccg    300
gccaggaatc tgttagaaaa ctcagagctc agtagaagga acactggctt tggaatgtgg   360
aggtctggtt ttgctcaaag tgtgcagtat gtgaaggaga acaatttact gaccattact   420
ctgccttact gattcaaatt ctgaggttta ttgaataatt tcttagattg ccttccagct   480
ctaaatttct cagcaccaaa atgaagtcca tttcaatctc tctctctctc tttccctccc   540
gtacatatac acacactcat acatatatat ggtcacaata gaaaggcagg tagatcagaa   600
gtctcagttg ctgagaaaga gggagggagg gtgagccaga ggtaccttct cccccattgt   660
agagaaaagt gaagttcttt tagagcccg ttacatcttc aaggcttttt atgagataat    720
ggaggaaata aagagggctc agtccttcta ctgtccatat ttcattctca aatctgttat   780
```

```
tagaggaatg attctgatct ccacctacca tacacatgcc ctgttgcttg ttgggccttc      840
ctaaaatgtt agagtatgat gacagatgga gttgtctggg tacatttgtg tgcatttaag      900
ggtgatagtg tatttgctct ttaagagctg agtgtttgag cctctgtttg tgtgtaattg      960
agtgtgcatg tgtgggagtg aaattgtgga atgtgtatgc tcatagcact gagtgaaaat     1020
aaaagattgt ataaatcgtg gggcatgtgg aattgtgtgt gcctgtgcgt gtgcagtatt     1080
tttttttttt taagtaagcc actttagatc ttgtcacctc ccctgtcttc tgtgattgat     1140
tttgcgaggc taatggtgcg taaaagggct ggtgagatct gggggcgcct cctagcctga     1200
cgtcagagag agagtttaaa acagagggag acggttgaga gca                       1243
```

<210> SEQ ID NO 6
<211> LENGTH: 1723
<212> TYPE: DNA
<213> ORGANISM: Artificial Sequence
<220> FEATURE:
<223> OTHER INFORMATION: Promoter

<400> SEQUENCE: 6

```
gtcgacattg attattgact agttattaat agtaatcaat tacgggGtca ttagttcata       60
gcccatatat ggagttccgc gttacataac ttacggtaaa tggcccgcct ggctgaccgc      120
ccaacgaccc ccgcccattg acgtcaataa tgacgtatgt tcccatagta acgccaatag      180
ggactttcca ttgacgtcaa tgggtggact atttacggta aactgcccac ttggcagtac      240
atcaagtgta tcatatgcca agtacgcccc ctattgacgt caatgacggt aaatggcccg      300
cctggcatta tgcccagtac atgaccttat gggactttcc tacttggcag tacatctacg      360
tattagtcat cgctattacc atgggtcgag gtgagcccca cgttctgctt cactctcccc      420
atctcccccc cctccccacc cccaattttg tatttattta ttttttaatt attttgtgca      480
gcgatggggg cggggggggg ggggcgcgc gccaggcggg gcgggGcggg gcgagggGcg      540
gggcggggcg aggcggagag gtgcggcggc agccaatcag agcggcgcgc tccgaaagtt      600
tccttttatg gcgaggcggc ggcggcggcg gccctataaa aagcgaagcg cgcggcgggc      660
gggagtcgct gcgttgcctt cgccccgtgc cccgctccgc gccgcctcgc gccgcccgcc      720
ccggctctga ctgaccgcgt tactcccaca ggtgagcggg cgggacggcc cttctcctcc      780
gggctgtaat tagcgcttgg tttaatgacg gctcgtttct tttctgtggc tgcgtgaaag      840
ccttaaaggg ctccgggagg gcccctttgtg cggggggGgag cggctcgggg ggtgcgtgcg      900
tgtgtgtgtg cgtgggGagc gccgcgtgcg gcccgcgctg cccggcggct gtgagcgctg      960
cgggcgcggc gcgggGctTt gtgcgctccg cgtgtgcgcg aggggagcgc ggccgggggc     1020
ggtgccccgc ggtgcggggg ggctgcgagg gGaacaaagg ctgcgtgcgg ggtgtgtgcg     1080
tgggggggtg agcagggggt gtgggcgcgg cggtcgggct gtaaccccCc cctgcacccc     1140
cctccccgag ttgctgagca cggcccggct tcgggtgcgg ggctccgtgc ggggcgtggc     1200
gcggggctcg ccgtgccggg cggggggtgg cggcaggtgg gggtgccggg cggggcgggg     1260
ccgcctcggg ccggggaggg ctcgggggag gggcgcggcg gccccggagc gccggcggct     1320
gtcgaggcgc ggcgagccgc agccattgcc ttttatggta atcgtgcgag agggcgcagg     1380
gacttccttt gtcccaaatc tggcggagcc gaaatctggg aggcgccgcc gcaccccctc     1440
tagcgggcgc gggcgaagcg gtgcggcgcc ggcaggaagg aaatgggcgg gagggccttt     1500
cgtgcgtcgc cgcgccgccg tcccCttctc catctccagc ctcggggctg ccgcagggGg     1560
acggctgcct tcggggggga cggggcaggg cggggttcgg cttctggcgt gtgaccggcg     1620
```

| | |
|---|---|
| gctctagagc ctctgctaac catgttcatg ccttcttctt tttcctacag ctcctgggca | 1680 |
| acgtgctggt tattgtgctg tctcatcatt ttggcaaaga att | 1723 |

<210> SEQ ID NO 7
<211> LENGTH: 1178
<212> TYPE: DNA
<213> ORGANISM: Homo sapiens

<400> SEQUENCE: 7

| | |
|---|---|
| ggctccggtg cccgtcagtg ggcagagcgc acatcgccca cagtccccga gaagttgggg | 60 |
| ggaggggtcg gcaattgaac cggtgcctag agaaggtggc gcggggtaaa ctgggaaagt | 120 |
| gatgtcgtgt actggctccg ccttttccc gagggtgggg gagaaccgta tataagtgca | 180 |
| gtagtcgccg tgaacgttct ttttcgcaac gggtttgccg ccagaacaca ggtaagtgcc | 240 |
| gtgtgtggtt cccgcgggcc tggcctcttt acgggttatg gcccttgcgt gccttgaatt | 300 |
| acttccactg gctgcagtac gtgattcttg atcccgagct tcgggttgga agtgggtggg | 360 |
| agagttcgag gccttgcgct taaggagccc cttcgcctcg tgcttgagtt gaggcctggc | 420 |
| ctgggcgctg gggccgccgc gtgcgaatct ggtggcacct tcgcgcctgt ctcgctgctt | 480 |
| tcgataagtc tctagccatt taaaatttt gatgacctgc tgcgacgctt tttttctggc | 540 |
| aagatagtct tgtaaatgcg ggccaagatc tgcacactgg tatttcggtt tttggggccg | 600 |
| cgggcggcga cggggcccgt gcgtcccagc gcacatgttc ggcgaggcgg ggcctgcgag | 660 |
| cgcggccacc gagaatcgga cggggtagt ctcaagctgg ccggcctgct ctggtgcctg | 720 |
| gcctcgcgcc gccgtgtatc gccccgccct gggcggcaag gctggcccgg tcggcaccag | 780 |
| ttgcgtgagc ggaaagatgg ccgcttcccg gccctgctgc agggagctca aaatggagga | 840 |
| cgcggcgctc gggagagcgg gcgggtgagt caccccacaca aaggaaaagg gcctttccgt | 900 |
| cctcagccgt cgcttcatgt gactccacgg agtaccgggc gccgtccagg cacctcgatt | 960 |
| agttctcgag cttttggagt acgtcgtctt taggttgggg ggaggggttt tatgcgatgg | 1020 |
| agtttcccca cactgagtgg gtggagactg aagttaggcc agcttggcac ttgatgtaat | 1080 |
| tctccttgga atttgccctt tttgagtttg gatcttggtt cattctcaag cctcagacag | 1140 |
| tggttcaaag ttttttctt ccatttcagg tgtcgtga | 1178 |

<210> SEQ ID NO 8
<211> LENGTH: 1609
<212> TYPE: DNA
<213> ORGANISM: Homo sapiens

<400> SEQUENCE: 8

| | |
|---|---|
| gatctctatt tatttagcaa taatagagaa agcatttaag agaataaagc aatggaaata | 60 |
| agaaatttgt aaatttcctt ctgataacta gaaatagagg atccagtttc ttttggttaa | 120 |
| cctaaattt atttcatttt attgttttat tttattttat tttatttat tttgtgtaat | 180 |
| cgtagtttca gagtgttaga gctgaaagga agaagtagga gaaacatgca agtaaaagt | 240 |
| ataacacttt ccttactaaa ccgacatggg tttccaggta ggggcaggat tcaggatgac | 300 |
| tgacagggcc cttagggaac actgagaccc tacgctgacc tcataaatgc ttgctacctt | 360 |
| tgctgtttta attacatctt ttaatagcag gaagcagaac tctgcacttc aaaagttttt | 420 |
| cctcacctga ggagttaatt tagtacaagg ggaaaaagta caggggggatg ggagaaaggc | 480 |
| gatcacgttg ggaagctata gagaaagaag agtaaatttt agtaaggag gtttaaacaa | 540 |

```
acaaaatata aagagaaata ggaacttgaa tcaaggaaat gattttaaaa cgcagtattc    600
ttagtggact agaggaaaaa aataatctga gccaagtaga agaccttttc ccctcctacc    660
cctactttct aagtcacaga ggcttttgt tcccccagac actcttgcag attagtccag    720
gcagaaacag ttagatgtcc ccagttaacc tcctatttga caccactgat taccccattg   780
atagtcacac tttgggttgt aagtgactt ttattattt gtattttga ctgcattaag      840
aggtctctag ttttttatct cttgttccc aaaacctaat aagtaactaa tgcacagagc    900
acattgattt gtatttattc tatttttaga cataatttat tagcatgcat gagcaaatta   960
agaaaaacaa caacaaatga atgcatatat atgtatatgt atgtgtgtat atatacacac  1020
atatatatat atattttttc ttttcttacc agaaggtttt aatccaaata aggagaagat  1080
atgcttagaa ccgaggtaga gttttcatcc attctgtcct gtaagtattt tgcatattct  1140
ggagacgcag gaagagatcc atctacatat cccaaagctg aattatggta gacaaaactc  1200
ttccactttt agtgcatcaa cttcttattt gtgtaataag aaaattggga aaacgatctt  1260
caatatgctt accaagctgt gattccaaat attacgtaaa tacacttgca aaggaggatg  1320
tttttagtag caatttgtac tgatggtatg gggccaagag atatatctta gagggagggc  1380
tgaggggtttg aagtccaact cctaagccag tgccagaaga gccaaggaca ggtacggctg  1440
tcatcactta gacctcaccc tgtggagcca caccctaggg ttggccaatc tactcccagg  1500
agcagggagg gcaggagcca gggctgggca taaaagtcag gcagagcca tctattgctt   1560
acatttgctt ctgacacaac tgtgttcact agcaacctca aacagacac               1609
```

```
<210> SEQ ID NO 9
<211> LENGTH: 684
<212> TYPE: DNA
<213> ORGANISM: Artificial Sequence
<220> FEATURE:
<223> OTHER INFORMATION: cytomegalovirus promoter

<400> SEQUENCE: 9
tcaatattgg ccattagcca tattattcat tggttatata gcataaatca atattggcta    60
ttggccattg catacgttgt atctatatca taatatgtac atttatattg gctcatgtcc   120
aatatgaccg ccatgttggc attgattatt gactagttat taatagtaat caattacggg   180
gtcattagtt catagcccat atatggagtt ccgcgttaca taacttacgg taaatggccc   240
gcctggctga ccgcccaacg acccccgccc attgacgtca ataatgacgt atgttcccat   300
agtaacgcca atagggactt tccattgacg tcaatgggtg gagtatttac ggtaaactgc   360
ccacttggca gtacatcaag tgtatcatat gccaagtccg cccccattg acgtcaatga    420
cggtaaatgg cccgcctggc attatgccca gtacatgacc ttacgggact ttcctacttg   480
gcagtacatc tacgtattag tcatcgctat taccatggtg atgcggtttt ggcagtacac   540
caatgggcgt ggatagcggt ttgactcacg gggatttcca gtctccaccc ccattgacgt   600
caatgggagt ttgttttggc accaaaatca acgggacttt ccaaaatgtc gtaataaccc   660
cgccccgttg acgcaaatgg gcgg                                          684
```

```
<210> SEQ ID NO 10
<211> LENGTH: 353
<212> TYPE: PRT
<213> ORGANISM: Homo sapiens

<400> SEQUENCE: 10

Met Ala Ala Glu Leu Ala Met Gly Ala Glu Leu Pro Ser Ser Pro Leu
```

```
             1               5                  10                 15
           Ala Ile Glu Tyr Val Asn Asp Phe Asp Leu Met Lys Phe Glu Val Lys
                          20                  25                 30
           Lys Glu Pro Pro Glu Ala Glu Arg Phe Cys His Arg Leu Pro Pro Gly
                          35                  40                 45
           Ser Leu Ser Ser Thr Pro Leu Ser Thr Pro Cys Ser Ser Val Pro Ser
               50                  55                  60
           Ser Pro Ser Phe Cys Ala Pro Ser Pro Gly Thr Gly Gly Gly Gly Gly
           65                  70                  75                 80
           Ala Gly Gly Gly Gly Ser Ser Gln Ala Gly Gly Ala Pro Gly Pro
                              85                  90                 95
           Pro Ser Gly Gly Pro Gly Ala Val Gly Gly Thr Ser Gly Lys Pro Ala
                              100                 105                110
           Leu Glu Asp Leu Tyr Trp Met Ser Gly Tyr Gln His His Leu Asn Pro
                              115                 120                125
           Glu Ala Leu Asn Leu Thr Pro Glu Asp Ala Val Glu Ala Leu Ile Gly
                              130                 135                140
           Ser Gly His His Gly Ala His His Gly Ala His His Pro Ala Ala Ala
           145                 150                 155                160
           Ala Ala Tyr Glu Ala Phe Arg Gly Pro Gly Phe Ala Gly Gly Gly Gly
                              165                 170                175
           Ala Asp Asp Met Gly Ala Gly His His His Gly Ala His His Ala Ala
                              180                 185                 190
           His His His His Ala Ala His His His His His His His His
                          195                  200                 205
           Gly Gly Ala Gly His Gly Gly Ala Gly His His Val Arg Leu Glu
                          210                  215                 220
           Glu Arg Phe Ser Asp Asp Gln Leu Val Ser Met Ser Val Arg Glu Leu
           225                 230                 235                240
           Asn Arg Gln Leu Arg Gly Phe Ser Lys Glu Glu Val Ile Arg Leu Lys
                              245                 250                 255
           Gln Lys Arg Arg Thr Leu Lys Asn Arg Gly Tyr Ala Gln Ser Cys Arg
                              260                 265                 270
           Phe Lys Arg Val Gln Gln Arg His Ile Leu Glu Ser Glu Lys Cys Gln
                              275                 280                 285
           Leu Gln Ser Gln Val Glu Gln Leu Lys Leu Glu Val Gly Arg Leu Ala
                              290                 295                 300
           Lys Glu Arg Asp Leu Tyr Lys Glu Lys Tyr Glu Lys Leu Ala Gly Arg
           305                 310                 315                320
           Gly Gly Pro Gly Ser Ala Gly Gly Ala Gly Phe Pro Arg Glu Pro Ser
                              325                 330                 335
           Pro Pro Gln Ala Gly Pro Gly Ala Lys Gly Thr Ala Asp Phe Phe
                              340                 345                 350
           Leu
```

<210> SEQ ID NO 11
<211> LENGTH: 359
<212> TYPE: PRT
<213> ORGANISM: Mus musculus

<400> SEQUENCE: 11

```
           Met Ala Ala Glu Leu Ala Met Gly Ala Glu Leu Pro Ser Ser Pro Leu
           1               5                   10                 15

Ala Ile Glu Tyr Val Asn Asp Phe Asp Leu Met Lys Phe Glu Val Lys
```

```
            20                  25                  30
Lys Glu Pro Pro Glu Ala Glu Arg Phe Cys His Arg Leu Pro Pro Gly
        35                  40                  45

Ser Leu Ser Ser Thr Pro Leu Ser Thr Pro Cys Ser Ser Val Pro Ser
    50                  55                  60

Ser Pro Ser Phe Cys Ala Pro Ser Pro Gly Thr Gly Gly Gly Ala Gly
65                  70                  75                  80

Gly Gly Gly Ser Ala Ala Gln Ala Gly Gly Ala Pro Gly Pro Pro Ser
                85                  90                  95

Gly Gly Pro Gly Thr Val Gly Gly Ala Ser Gly Lys Ala Val Leu Glu
            100                 105                 110

Asp Leu Tyr Trp Met Ser Gly Tyr Gln His His Leu Asn Pro Glu Ala
        115                 120                 125

Leu Asn Leu Thr Pro Glu Asp Ala Val Glu Ala Leu Ile Gly Ser Gly
    130                 135                 140

His His Gly Ala His Gly Ala His His Pro Ala Ala Ala Ala Ala Ala
145                 150                 155                 160

Tyr Glu Ala Phe Arg Gly Gln Ser Phe Ala Gly Gly Gly Gly Ala Asp
                165                 170                 175

Asp Met Gly Ala Gly His His Gly Ala His His Thr Ala His His
            180                 185                 190

His His Ser Ala His His His His His His His His His Gly Gly
        195                 200                 205

Ser Gly His His Gly Gly Ala Gly His Gly Gly Gly Ala Gly
    210                 215                 220

His His Val Arg Leu Glu Glu Arg Phe Ser Asp Asp Gln Leu Val Ser
225                 230                 235                 240

Met Ser Val Arg Glu Leu Asn Arg Gln Leu Arg Gly Phe Ser Lys Glu
                245                 250                 255

Glu Val Ile Arg Leu Lys Gln Lys Arg Arg Thr Leu Lys Asn Arg Gly
            260                 265                 270

Tyr Ala Gln Ser Cys Arg Phe Lys Arg Val Gln Gln Arg His Ile Leu
        275                 280                 285

Glu Ser Glu Lys Cys Gln Leu Gln Ser Gln Val Glu Gln Leu Lys Leu
    290                 295                 300

Glu Val Gly Arg Leu Ala Lys Glu Arg Asp Leu Tyr Lys Glu Lys Tyr
305                 310                 315                 320

Glu Lys Leu Ala Gly Arg Gly Pro Gly Gly Ala Gly Gly Ala Gly
                325                 330                 335

Phe Pro Arg Glu Pro Ser Pro Ala Gln Ala Gly Pro Gly Ala Ala Lys
            340                 345                 350

Gly Ala Pro Asp Phe Phe Leu
        355

<210> SEQ ID NO 12
<211> LENGTH: 283
<212> TYPE: PRT
<213> ORGANISM: Homo sapiens

<400> SEQUENCE: 12

Met Asn Gly Glu Glu Gln Tyr Tyr Ala Ala Thr Gln Leu Tyr Lys Asp
1               5                   10                  15

Pro Cys Ala Phe Gln Arg Gly Pro Ala Pro Glu Phe Ser Ala Ser Pro
            20                  25                  30
```

```
Pro Ala Cys Leu Tyr Met Gly Arg Gln Pro Pro Pro Pro Pro His
         35                  40                  45
Pro Phe Pro Gly Ala Leu Gly Ala Leu Glu Gln Gly Ser Pro Pro Asp
 50                  55                  60
Ile Ser Pro Tyr Glu Val Pro Pro Leu Ala Asp Asp Pro Ala Val Ala
 65                  70                  75                  80
His Leu His His His Leu Pro Ala Gln Leu Ala Leu Pro His Pro Pro
                 85                  90                  95
Ala Gly Pro Phe Pro Glu Gly Ala Glu Pro Gly Val Leu Glu Glu Pro
                100                 105                 110
Asn Arg Val Gln Leu Pro Phe Pro Trp Met Lys Ser Thr Lys Ala His
                115                 120                 125
Ala Trp Lys Gly Gln Trp Ala Gly Gly Ala Tyr Ala Ala Glu Pro Glu
                130                 135                 140
Glu Asn Lys Arg Thr Arg Thr Ala Tyr Thr Arg Ala Gln Leu Leu Glu
145                 150                 155                 160
Leu Glu Lys Glu Phe Leu Phe Asn Lys Tyr Ile Ser Arg Pro Arg Arg
                165                 170                 175
Val Glu Leu Ala Val Met Leu Asn Leu Thr Glu Arg His Ile Lys Ile
                180                 185                 190
Trp Phe Gln Asn Arg Arg Met Lys Trp Lys Lys Glu Glu Asp Lys Lys
                195                 200                 205
Arg Gly Gly Gly Thr Ala Val Gly Gly Gly Val Ala Glu Pro Glu
                210                 215                 220
Gln Asp Cys Ala Val Thr Ser Gly Glu Glu Leu Leu Ala Leu Pro Pro
225                 230                 235                 240
Pro Pro Pro Pro Gly Gly Ala Val Pro Pro Ala Ala Pro Val Ala Ala
                245                 250                 255
Arg Glu Gly Arg Leu Pro Pro Gly Leu Ser Ala Ser Pro Gln Pro Ser
                260                 265                 270
Ser Val Ala Pro Arg Arg Pro Gln Glu Pro Arg
                275                 280

<210> SEQ ID NO 13
<211> LENGTH: 284
<212> TYPE: PRT
<213> ORGANISM: Mus musculus

<400> SEQUENCE: 13

Met Asn Ser Glu Glu Gln Tyr Tyr Ala Ala Thr Gln Leu Tyr Lys Asp
 1               5                  10                  15
Pro Cys Ala Phe Gln Arg Gly Pro Val Pro Glu Phe Ser Ala Asn Pro
                 20                  25                  30
Pro Ala Cys Leu Tyr Met Gly Arg Gln Pro Pro Pro Pro Pro Pro
         35                  40                  45
Gln Phe Thr Ser Ser Leu Gly Ser Leu Glu Gln Gly Ser Pro Pro Asp
 50                  55                  60
Ile Ser Pro Tyr Glu Val Pro Pro Leu Ala Ser Asp Asp Pro Ala Gly
 65                  70                  75                  80
Ala His Leu His His His Leu Pro Ala Gln Leu Gly Leu Ala His Pro
                 85                  90                  95
Pro Pro Gly Pro Phe Pro Asn Gly Thr Glu Pro Gly Gly Leu Glu Glu
                100                 105                 110
Pro Asn Arg Val Gln Leu Pro Phe Pro Trp Met Lys Ser Thr Lys Ala
                115                 120                 125
```

```
His Ala Trp Lys Gly Gln Trp Ala Gly Gly Ala Tyr Thr Ala Glu Pro
    130                 135                 140

Glu Glu Asn Lys Arg Thr Arg Thr Ala Tyr Thr Arg Ala Gln Leu Leu
145                 150                 155                 160

Glu Leu Glu Lys Glu Phe Leu Phe Asn Lys Tyr Ile Ser Arg Pro Arg
                165                 170                 175

Arg Val Glu Leu Ala Val Met Leu Asn Leu Thr Glu Arg His Ile Lys
            180                 185                 190

Ile Trp Phe Gln Asn Arg Arg Met Lys Trp Lys Lys Glu Glu Asp Lys
        195                 200                 205

Lys Arg Ser Ser Gly Thr Pro Ser Gly Gly Gly Gly Glu Glu Pro
    210                 215                 220

Glu Gln Asp Cys Ala Val Thr Ser Gly Glu Glu Leu Leu Ala Val Pro
225                 230                 235                 240

Pro Leu Pro Pro Pro Gly Gly Ala Val Pro Pro Gly Val Pro Ala Ala
                245                 250                 255

Val Arg Glu Gly Leu Leu Pro Ser Gly Leu Ser Val Ser Pro Gln Pro
            260                 265                 270

Ser Ser Ile Ala Pro Leu Arg Pro Gln Glu Pro Arg
        275                 280

<210> SEQ ID NO 14
<211> LENGTH: 48
<212> TYPE: DNA
<213> ORGANISM: Artificial Sequence
<220> FEATURE:
<223> OTHER INFORMATION: synthetic oligodeoxynucleotide connector

<400> SEQUENCE: 14
cgcgccaagc gcggctccgg cgccaccaac ttctccctgc tgaagcag                    48

<210> SEQ ID NO 15
<211> LENGTH: 81
<212> TYPE: DNA
<213> ORGANISM: Artificial Sequence
<220> FEATURE:
<223> OTHER INFORMATION: synthetic oligodeoxynucleotide connector

<400> SEQUENCE: 15
cgcgccaagc gcggctccgg ccagtgcacc aactacgccc tgctgaagct ggccggcgac      60
gtggagtcca accccggccc c                                                81

<210> SEQ ID NO 16
<211> LENGTH: 75
<212> TYPE: DNA
<213> ORGANISM: Artificial Sequence
<220> FEATURE:
<223> OTHER INFORMATION: synthetic oligodeoxynucleotide connector

<400> SEQUENCE: 16
cgcgccaagc gcggctccgg cgagggcaga ggaagtcttc taacatgcgg tgacgtggag      60
gagaatcccg gccct                                                        75

<210> SEQ ID NO 17
<211> LENGTH: 214
<212> TYPE: PRT
<213> ORGANISM: Homo sapiens

<400> SEQUENCE: 17
```

```
Met Ala Pro His Pro Leu Asp Ala Leu Thr Ile Gln Val Ser Pro Glu
1               5                   10                  15

Thr Gln Gln Pro Phe Pro Gly Ala Ser Asp His Glu Val Leu Ser Ser
            20              25                  30

Asn Ser Thr Pro Pro Ser Pro Thr Leu Ile Pro Arg Asp Cys Ser Glu
            35              40                  45

Ala Glu Val Gly Asp Cys Arg Gly Thr Ser Arg Lys Leu Arg Ala Arg
    50              55              60

Arg Gly Gly Arg Asn Arg Pro Lys Ser Glu Leu Ala Leu Ser Lys Gln
65              70              75                  80

Arg Arg Ser Arg Arg Lys Lys Ala Asn Asp Arg Glu Arg Asn Arg Met
            85              90                  95

His Asn Leu Asn Ser Ala Leu Asp Ala Leu Arg Gly Val Leu Pro Thr
            100             105                 110

Phe Pro Asp Asp Ala Lys Leu Thr Lys Ile Glu Thr Leu Arg Phe Ala
        115             120                 125

His Asn Tyr Ile Trp Ala Leu Thr Gln Thr Leu Arg Ile Ala Asp His
    130             135                 140

Ser Phe Tyr Gly Pro Glu Pro Pro Val Pro Cys Gly Glu Leu Gly Ser
145             150             155                 160

Pro Gly Gly Gly Ser Asn Gly Asp Trp Gly Ser Ile Tyr Ser Pro Val
            165             170                 175

Ser Gln Ala Gly Asn Leu Ser Pro Thr Ala Ser Leu Glu Glu Phe Pro
            180             185                 190

Gly Leu Gln Val Pro Ser Ser Pro Ser Tyr Leu Leu Pro Gly Ala Leu
        195             200                 205

Val Phe Ser Asp Phe Leu
        210
```

ENDOGENOUS NEOGENESIS OF BETA CELLS

CROSS REFERENCE TO RELATED APPLICATION

This is a § 371 U.S. national stage of International Application No. PCT/US2015/026532, filed Apr. 17, 2015, which was published in English under PCT Article 21(2), which claims the benefit of U.S. Provisional Application No. 61/983,295, filed Apr. 23, 2014, which is incorporated herein by reference.

ACKNOWLEDGMENT OF GOVERNMENT SUPPORT

This invention was made with government support under grant nos. DK083541 and DK098196 awarded by the National Institutes of Health. The government has certain rights in the invention.

FIELD

This relates to the field of beta cells, specifically to the intraductal administration of a viral vector encoding pancreas duodenal homeobox protein (Pdx)1 and MafA, wherein the vector does not encode Neurogenin (Ngn) 3, to induce the production of beta cells in the pancreas.

BACKGROUND

A mammalian pancreas is composed of two subclasses of tissue: the exocrine cells of the acinar tissue and the endocrine cells of the islets of Langerhans. The exocrine cells produce digestive enzymes that are secreted through the pancreatic duct to the intestine. The islet cells produce polypeptide hormones that are involved in carbohydrate metabolism. The islands of endocrine tissue that exist within the adult mammalian pancreas are termed the islets of Langerhans. Adult mammalian islets are composed of five major cell types, the $\alpha$, $\beta$, $\delta$, PP, and $\epsilon$ cells. These cells are distinguished by their production of glucagon, insulin, somatostatin, pancreatic polypeptide, and ghrelin, respectively.

Diabetes mellitus results from the failure of cells to transport endogenous glucose across their membranes either because of an endogenous deficiency of insulin or an insulin receptor defect. Type 1 diabetes (T1D) is caused by the destruction of $\beta$ cells, which results in insufficient levels of endogenous insulin. Current treatment of individuals with clinical manifestation of diabetes attempts to emulate the role of the pancreatic $\beta$ cells in a non-diabetic individual. Generally, treatment of a diabetic individual involves monitoring of blood glucose levels and the use of injected bovine, porcine, or cloned human insulin as required. Despite such intervention, there is often a gradual decline in the health of diabetics. Diabetes afflicts millions of people in the United States alone, and there is a clear need to provide additional treatments for this disease.

SUMMARY

It is disclosed herein that a viral vector, such as an adenoviral vector or an adeno-associated viral vector encoding pancreas duodenal homeobox protein (Pdx1) and musculoaponeurotic fibrosarcoma oncogene homolog A (MafA) can be infused through the pancreatic duct of a subject, such as a subject with type 1 diabetes, in order to reprogram alpha-cells into functional beta-cells. Surprisingly, these beta cells are immunologically unrecognized for an extended period by the immune system of the subject. The viral vector can be delivered to the subject using endoscopic retrograde cholangiopancreatography (ERCP). The subject is not administered Neurogenin 3 (Ngn3) or a nucleic acid encoding Ngn3.

In some embodiments, a method is disclosed for producing pancreatic beta cells in a subject. The methods include administering to the subject a vector encoding heterologous Pdx1 and MafA, wherein the vector does not encode Ngn3 and wherein the subject is not administered any other nucleic acid encoding Ngn3. The vector is administered intraductally into a pancreatic duct of the subject. In specific non-limiting examples, the subject has diabetes type 1.

In further embodiments a composition is disclosed that includes a) an adeno-associated virus vector comprising a promoter operably linked to a nucleic acids encoding Pdx1 and a nucleic acid encoding MafA, wherein the vector does not encode Ngn3; b) a buffer; and c) a contrast dye for endoscopic retrograde cholangiopancreatography. These compositions are of use in any of the methods disclosed herein. In specific non-limiting examples, these compositions are formulated for intraductal administration.

The foregoing and other objects, features, and advantages of the invention will become more apparent from the following detailed description, which proceeds with reference to the accompanying figures.

BRIEF DESCRIPTION OF THE DRAWINGS

FIGS. 1A-1E: Intraductal infusion of AAV-PM corrected ALX-induced hyperglycemia in GCG-Cre; R26R$^{Tomato}$ mice. (A) Schematic for the generation of GCG-Cre; R26R$^{Tomato}$ mice. (B) Representative image of an islet from GCG-Cre; R26R$^{Tomato}$ mice. TOM: tomato; INS: insulin; GCG: glucagon; HO: Hoechst, nuclear stain. (C) Hyperglycemia was induced in GCG-Cre; R26R$^{Tomato}$ mice by ALX injection. One week after alloxan (ALX) treatment, mice received a pancreatic intraductal infusion of either AAV-PM or control AAV-GFP (see the examples section). Fasting blood glucose levels were measured, showing sustained hyperglycemia in control mice (solid line), but normalization of hyperglycemia in mice within 2 weeks after infusion with AAV-PM (black dotted line). (D) Intraperitoneal glucose tolerance test (IPGTT) was performed in these mice 4 weeks after viral infusion. Untreated mice (no ALX, no virus, in dashed line) were used as an additional control. (E) Beta cell mass was analyzed 4 weeks after virus infusion, showing a significant recovery of beta cell mass in mice that received AAV-PM viral infusion (the contribution of beta cells without tomato red fluorescence is shown by the hatched bar contained within the black dots bar), compared to the beta cell mass in mice that received AAV-GFP viral infusion (black bar), and reached more than 60% of the beta cell mass of untreated mice (UT, no ALX, no virus, dashed bar). *: $p<0.05$. **: $p<0.01$ (compared to control ALX+ AAV-GFP). Scale bars are 50 µM.

FIGS. 3A-3C: Intraductal infusion of AAV-PM reversed hyperglycemia in NOD mice. (A) When the blood glucose of female non-obese diabetic (NOD) mice surpassed 200 mg/dl, the mice received an intraductal infusion of either AAV-PM or control AAV-GFP. Fasting blood glucose levels were measured, showing continuously increasing hyperglycemia in control mice (black line), but immediate stabilization and then, by 2-3 weeks, normalization of hyperglycemia in mice infused with AAV-PM (dotted line), lasting for about 4 months. (B) Immunostaining for insulin (INS) and CD45 (in white) 5 weeks after infusion of control AAV-GFP (upper panels) or AAV-PM (lower panels), along with direct green fluorescence (GFP) from viral infection. HO: Hoechst, nuclear stain. (C) Representative confocal images for insulin (INS) and GCG 5 weeks after infusion of AAV-PM, along with direct green fluorescence (GFP) from viral infection, showing many cells that were double positive for both INS and GCG (arrows). **: $p<0.01$ (compared to control AAV-GFP into NOD). Scale bars are 50 μM.

FIGS. 4A-4D: Assessment of the status of the NOD autoimmunity following viral therapy. (A) Splenocytes isolated from untreated diabetic NOD mice (UT), and from AAV-PM-infused and AAV-GFP-infused NOD mice 4 weeks after viral infusion were adoptively transferred into NOD/SCID mice. The development of diabetes in recipient NOD/SCID mice was compared. (B) NOD/SCID mouse islets (300) were transplanted under the kidney capsules of AAV-PM-treated and AAV-GFP-treated NOD mice 4 weeks after viral infusion, and into undisturbed NOD/SCID mice as a control. (C) Quantification of graft insulin content one week after transplantation. (D) Representative images for insulin (INS) and CD45 in the islet graft under the kidney capsule. *: $p<0.05$. **: $p<0.01$ (compared to control AAV-GFP). Scale bars are 50 μM.

FIGS. 5A-5F: AAV-PM induced generation of functional beta cells in human islets. (A) Human islets were treated with 20 mmol/l STZ for 12 hours, after which the islets were treated with either AAV-PM or AAV-GFP for 24 hours and then transplanted into ALX-treated hyperglycemic NOD/SCID mice. (B) The beta-cell-destroying effect of streptotozocin (STZ) was confirmed at 12 hours by examining insulin content per islet. (C-D) The ALX-NOD/SCID mice that received human islets treated with STZ and AAV-PM (solid line) had significantly lower fasted blood glucose levels (C), and significantly better glucose tolerance (D), as early as 1 week after transplantation, compared to the ALX-NOD/SCID mice that received human islets treated with STZ and AAV-GFP (dotted line). (E) Graft insulin content. (F) Representative images for insulin (INS, in black) and glucagon (GCG, in black dots) in the graft under the kidney capsule. *: $p<0.05$. **: $p<0.01$ (compared to control AAV-GFP in NOD). Scale bars are 50 μM.

FIG. 6A-6I: In vitro conversion of aTC cells into beta-like cells. (A-I) Two weeks after infection with AAV-GFP (controls), AAV-Pdx1, AAV-MafA or AAV-Pdx1-MafA (PM), aTC were tested by RT-qPCR for expression of Pdx1 (A), MafA (B), Ngn3 (C), Pax4 (D), Insulin (INS, E) and Glucagon (GCG, F) mRNA. (G-I) Representative images of immunostaining for Pax4 (G), GCG (H) and INS (I). *: $p<0.05$. **: $p<0.01$ (compared to controls). HO: Hoechst nuclear stain. Scale bars are 20 μM.

SEQUENCE LISTING

Figures 1A, 1B:
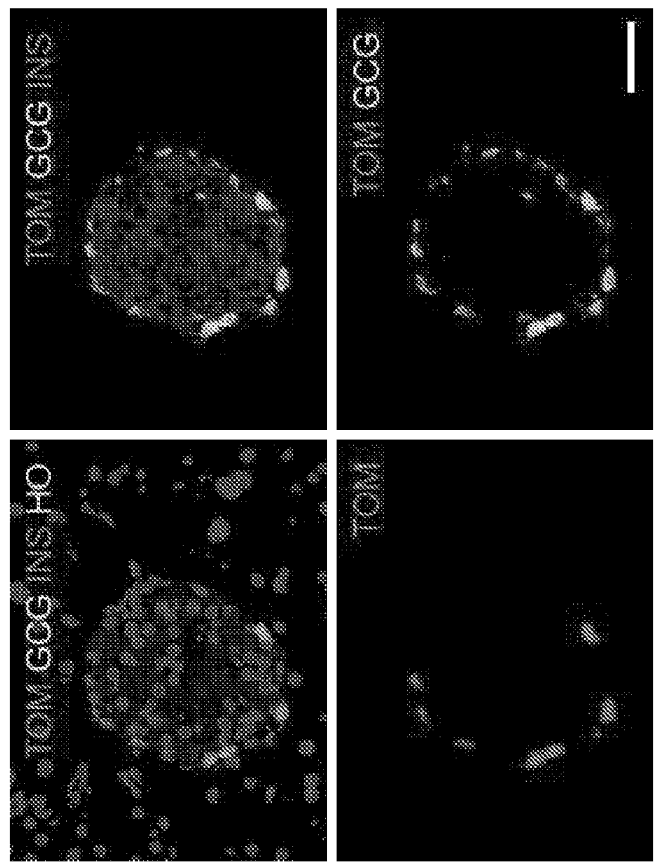

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "8123-92873-03 Sequence_Listing.txt" (~28.8 KB), which was created on Oct. 17, 2016, and is incorporated by reference herein. In the accompanying sequence listing:

SEQ ID NO: 1 is a nucleic acid sequence of a human glucagon promoter (short).

SEQ ID NO: 2 is a nucleic acid sequence of a human glucagon promoter (long).

SEQ ID NO: 3 is a nucleic acid sequence of a mouse glucagon promoter (short).

SEQ ID NO: 4 is a nucleic acid sequence of a human pancreatic polypeptide promoter.

SEQ ID NO: 5 is a nucleic acid sequence of a somatostatin promoter.

SEQ ID NO: 6 is a nucleic acid sequence of a CAG promoter.

SEQ ID NO: 7 is a nucleic acid sequence of an EF1 promoter.

SEQ ID NO: 8 is a nucleic acid sequence of a beta globin promoter.

SEQ ID NO: 9 is a nucleic acid sequence of a cytomegalovirus promoter.

SEQ ID NO: 10 is an amino acid sequence of human MafA protein.

SEQ ID NO: 11 is an amino acid sequence of mouse MafA protein.

SEQ ID NO: 12 is an amino acid sequence of human Pdx1 protein.

SEQ ID NO: 13 is an amino acid sequence of mouse Pdx1 protein.

SEQ ID NO: 14 is a nucleic acid sequence of a 2A connector.

SEQ ID NO: 15 is a nucleic acid sequence of a connector.

SEQ ID NO: 16 is a nucleic acid sequence of a connector.

SEQ ID NO: 17 is an amino acid sequence of human Ngn3 protein.

DETAILED DESCRIPTION

It is disclosed herein that adeno-associated virus encoding Pdx1 and MafA can be infused through the pancreatic duct, such as by using endoscopic retrograde cholangiopancreatography (ERCP), to reprogram alpha-cells into functional beta-cells. In some embodiments, the adeno-associated virus includes a glucagon promoter operably linked to a nucleic acid encoding Pdx1 and MafA. Strikingly, the new beta cells are immunologically unrecognized for an extended period, resulting in persistent euglycemia without further interventions. Without being bound by theory, the methods can result in the autoimmune immune system returning to a naive state in which immune cells are not actively being exposed to beta-cell autoantigens. Thus, expression of Pdx1 and MafA in the islet niche can be important for protecting new beta-cells in type 1 diabetes (T1D).

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Alpha (α) cells: Mature glucagon producing endocrine cells. In vivo, these cells are found in the pancreatic islets of Langerhans.

Beta (β) cells: Mature insulin producing endocrine cells. In vivo, these cells are found in the pancreatic islets of Langerhans, Delta (δ) cells: Mature somatostatin producing endocrine cells. In vivo, these cells are found in the pancreatic islets of Langerhans.

PP cells: Mature pancreatic polypeptide (PP) producing endocrine cells. In vivo, these cells are found in the pancreatic islets of Langerhans.

Adeno-associated virus (AAV): A small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. There are currently 11 recognized serotypes of AAV (AAV1-11).

Administration: To provide or give a subject an agent by any effective route. Exemplary routes of administration include, but are not limited to, oral, injection (such as subcutaneous, intramuscular, intradermal, intraperitoneal, intravenous, and intratumoral), sublingual, rectal, transdermal, intranasal, vaginal and inhalation routes. In some embodiments, administration is to a pancreatic duct.

Agent: Any polypeptide, compound, small molecule, organic compound, salt, polynucleotide, or other molecule of interest. Agent can include a therapeutic agent, a diagnostic agent or a pharmaceutical agent. A therapeutic agent is a substance that demonstrates some therapeutic effect by restoring or maintaining health, such as by alleviating the symptoms associated with a disease or physiological disorder, or delaying (including preventing) progression or onset of a disease, such as T1D.

Amplification: Of a nucleic acid molecule (such as, a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Anti-diabetic lifestyle modifications: Changes to lifestyle, habits, and practices intended to alleviate the symptoms of diabetes or pre-diabetes. Obesity and sedentary lifestyle may both independently increase the risk of a subject developing type II diabetes, so anti-diabetic lifestyle modifications include those changes that will lead to a reduction in a subject's body mass index (BMI), increase physical activity, or both. Specific, non-limiting examples include the lifestyle interventions described in *Diabetes Care,* 22(4):623-34 at pages 626-27, herein incorporated by reference.

Conservative Substitutions: Modifications of a polypeptide that involve the substitution of one or more amino acids for amino acids having similar biochemical properties that do not result in change or loss of a biological or biochemical function of the polypeptide are designated "conservative" substitutions. These conservative substitutions are likely to have minimal impact on the activity of the resultant protein. Table 1 shows amino acids that can be substituted for an original amino acid in a protein, and which are regarded as conservative substitutions.

TABLE

| Original Residue | Conservative Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

One or more conservative changes, or up to ten conservative changes (such as two substituted amino acids, three substituted amino acids, four substituted amino acids, or five substituted amino acids, etc.) can be made in the polypeptide without changing a biochemical function of the protein, such as Pdx1 or MafA.

Diabetes mellitus: A group of metabolic diseases in which a subject has high blood sugar, either because the pancreas does not produce enough insulin, or because cells do not respond to the insulin that is produced. Type 1 diabetes results from the body's failure to produce insulin. This form has also been called "insulin-dependent diabetes mellitus" (IDDM) or "juvenile diabetes". Type 1 diabetes mellitus is characterized by loss of the insulin-producing βcells, leading to insulin deficiency. This type can be further classified as immune-mediated or idiopathic. Type 2 diabetes results from insulin resistance, a condition in which cells fail to use insulin properly, sometimes combined with an absolute insulin deficiency. This form is also called "non insulin-dependent diabetes mellitus" (NIDDM) or "adult-onset diabetes." The defective responsiveness of body tissues to insulin is believed to involve the insulin receptor. Diabetes mellitus is characterized by recurrent or persistent hyperglycemia, and is diagnosed by demonstrating any one of:

a. Fasting plasma glucose level ≥7.0 mmol/l (126 mg/dl);
b. Plasma glucose ≥11.1 mmol/l (200 mg/dL) two hours after a 75 g oral glucose load as in a glucose tolerance test;
c. Symptoms of hyperglycemia and casual plasma glucose ≥11.1 mmol/l (200 mg/dl);
d. Glycated hemoglobin (Hb A1C)≥6.5%

Differentiation: The process whereby a first cell acquires specialized structural and/or functional features characteristic of a certain type of mature cells. Similarly, "differentiate" refers to this process. Typically, during differentiation, cellular structure alters and tissue-specific proteins appear. The term "differentiated pancreatic endocrine cell" refers to cells expressing a protein characteristic of the specific pancreatic endocrine cell type. A differentiated pancreatic endocrine cell includes an α cell, a β cell, a δ cell, and a PP cell, which express glucagon, insulin, somatostatin, and pancreatic polypeptide, respectively.

Endocrine: Tissue which secretes regulatory hormones directly into the bloodstream without the need for an associated duct system.

Enhancer: A nucleic acid sequence that increases the rate of transcription by increasing the activity of a promoter.

Expand: A process by which the number or amount of cells is increased due to cell division. Similarly, the terms "expansion" or "expanded" refers to this process. The terms "proliferate," "proliferation" or "proliferated" may be used interchangeably with the words "expand," "expansion," or "expanded."

Expressed: Translation of a nucleic acid into a protein. Proteins may be expressed and remain intracellular, become a component of the cell surface membrane, or be secreted into the extracellular matrix or medium.

Exocrine: Secretory tissue which distributes its products, such as enzymes, via an associated duct network. The exocrine pancreas is the part of the pancreas that secretes enzymes required for digestion. The exocrine cells of the pancreas include the centroacinar cells and basophilic cells, which produce secretin and cholecystokinin.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

Glucagon: A pancreatic enzyme produced by the pancreatic α cells in vivo. Exemplary glucagon amino acid sequences are shown in GENBANK® accession Nos: NP_002045.1 (pro-protein) (human); NP_032126.1

(mouse), both incorporated by reference. The term Glucagon also encompasses species variants, homologues, allelic forms, mutant forms, and equivalents thereof, including conservative substitutions, additions, deletions therein not adversely affecting the function, such as binding to the glucagon receptor. Glucagon is encoded by nucleic acid corresponding to GENBANK® Accession No: NM_002054.2 (human); NM_008100.3 (mouse), both incorporated by reference. The glucagon protein encoded by the glucagon is gene is a preproprotein that is cleaved into four distinct mature peptides. One of these, glucagon, is a pancreatic hormone that counteracts the glucose-lowering action of insulin by stimulating glycogenolysis and gluconeogenesis. Glucagon is a ligand for a specific G-protein linked receptor whose signalling pathway controls cell proliferation.

Heterologous: A heterologous sequence is a sequence that is not normally (in the wild-type sequence) found adjacent to a second sequence. In one embodiment, the sequence is from a different genetic source, such as a virus or organism, than the second sequence.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Insulin: A protein hormone involved in the regulation of blood sugar levels that is produced by pancreatic beta cells. In vivo, insulin is produced as a precursor proinsulin, consisting of the B and A chains of insulin linked together via a connecting C-peptide. Insulin itself includes only the B and A chains. Exemplary insulin sequences are provided in GENBANK® Accession NO. NM_000207.2 (human) and NM_008386.3 (mouse), as available on Apr. 1, 2015, and are incorporated by reference herein. Exemplary nucleic acid sequences encoding insulin are provided in GENBANK® Accession No: NM_000207.2 (human) and NM_008386.3 (mouse), as available on Apr. 1, 2015, and are incorporated by reference herein. The term insulin also encompasses species variants, homologues, allelic forms, mutant forms, and equivalents thereof, including conservative substitutions, additions, deletions therein not adversely affecting the structure of function.

Islets of Langerhans: Small discrete clusters of pancreatic endocrine tissue. In vivo, in an adult mammal, the islets of Langerhans are found in the pancreas as discrete clusters (islands) of pancreatic endocrine tissue surrounded by the pancreatic exocrine (or acinar) tissue. In vivo, the islets of Langerhans consist of the α cells, β cells, δ cells, PP cells, and ε cells. Histologically, in rodents, the islets of Langerhans consist of a central core of 0 cells surrounded by an outer layer of α cells, δ cells, and PP cells. The structure of human islets of Langerhans is different and distinct from rodents. The islets of Langerhans are sometimes referred to herein as "islets."

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. An isolated cell type has been substantially separated from other cell types, such as a different cell type that occurs in an organ. A purified cell or component can be at least 90%, at least 95%, at least 96%, at least 97%, at least 98%, or at least 99% pure.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes.

Musculoaponeurotic fibrosarcoma oncogene homolog A (MafA): MAFA is a transcription factor that binds RIPE3b, a conserved enhancer element that regulates pancreatic beta cell-specific expression of the insulin gene (INS; MIM 176730) (Olbrot et al., 2002). MafA is referred in the art as aliases; v-maf musculoaponeurotic fibrosarcoma oncogene homolog A (avian), hMafA; RIPE3b1; MAFA. Examplary MafA proteins are the MafA protein of GENBANK® Accession No: NM_194350 (mouse) (SEQ ID NO:3 32 of U.S. Published Patent Application No. 2011/0280842) or NP_963883.2 (Human)(SEQ ID NOs: 33 and 32 of U.S. Published Patent Application No. 2011/0280842); GeneID No: 389692, which are all incorporated by reference. The term MafA also encompasses species variants, homologues, allelic forms, mutant forms, and equivalents thereof, including conservative substitutions, additions, deletions that do not adversely affecting the structure of function. The term "MafA", or "MafA" protein"as used herein refers to a polypeptide having a naturally occurring amino acid sequence of a MafA" protein or a fragment, variant, or derivative thereof retains the ability of the naturally occurring protein to bind to DNA and activate gene transcription of Glut2 and pyruvate carboxylase, and other genes such as Glut2, Pdx-1, Nkx6.1, GLP-1 receptor, prohormone convertase-1/3 as disclosed in Wang et al., Diabetologia. 2007 February; 50(2): 348-358, which is incorporated herein by reference. Exemplary MafA nucleic acids are GENBANK® Accession No: NM_201589 (human) (SEQ ID NO:36 32 of U.S. Published Patent Application No. 2011/0280842) and GENBANK® Accession No: NM_194350 (mouse) (SEQ ID NO: 39 32 of U.S. Published Patent Application No. 2011/0280842), which are all incorporated by reference. In addition to naturally-occurring allelic variants of the MafA sequences that may exist in the population, it will be appreciated that, as is the case for virtually all proteins, a variety of changes can be introduced into the sequences of SEQ ID NO: 3 32 of U.S. Published Patent Application No. 2011/0280842 or SEQ ID NO: 33 32 of U.S. Published Patent Application No. 2011/0280842 (referred to as "wild type" sequences) without substantially altering the functional (biological) activity of the polypeptides. Such variants are included within the scope of the terms "MafA", "MafA protein", etc. U.S. Published Patent Application No. 2011/0280842 and all of the GENBANK entries are incorporated herein by reference.

Mammal: This term includes both human and non-human mammals. Similarly, the term "subject" includes both human and veterinary subjects.

Neurogenin (Ngn)3: Neurogenin-3 (also known as NEUROG3) is expressed in endocrine progenitor cells and is required for endocrine cell development in the pancreas and intestine. It belongs to a family of basic helix-loop-helix transcription factors involved in the determination of neural precursor cells in the neuroectoderm. Ngn3 is referred in the art as aliases; Neurogenin 3; Atoh5; Math4B; bHLHa7;

NEUROG3. Exemplary Ngn3 proteins are provided in GENBANK® Accession No: NM_009719 (mouse) and SEQ ID NO:2 of U.S. Published Patent Application No. 2011/0280842, both incorporated by reference herein or GENBANK® Accession No: NP_033849.3 (Human) and SEQ ID NO: 32 of U.S. Published Patent Application No. 2011/0280842, both incorporated by reference herein; GeneID No: 50674. The term Ngn3 also encompasses species variants, homologues, allelic forms, mutant forms, and equivalents thereof, including conservative substitutions, additions, deletions therein not adversely affecting the structure of function. Human Ngn3 is encoded by nucleic acid corresponding to GENBANK® Accession No: NM_020999 (human), SEQ ID NO:35 of U.S. Published Patent Application No. 2011/0280842 or NM_009719 (mouse), SEQ ID NO: 38 of U.S. Published Patent Application No. 2011/0280842. U.S. Published Patent Application No. 2011/0280842 and these GENBANK® Accession Nos. are incorporated by reference herein. The term "Ngn3", or "Ngn3 protein" as used herein refers to a polypeptide having a naturally occurring amino acid sequence of a Ngn3 protein or a fragment, variant, or derivative thereof that retains the ability of the naturally occurring protein to bind to DNA and activate gene transcription of NeuroD, Delta-like 1 (Dll1), HeyL, insulinoma-associated-1 (IA1), Nk2.2, Notch, HesS, Isl1, Somatostatin receptor 2 (Sstr2) and other genes as disclosed in Serafimidis et al., Stem cells; 2008; 26; 3-16, which is incorporated herein in its entirety by reference. In addition to naturally-occurring allelic variants of the Ngn3 sequences that may exist in the population, it will be appreciated that, as is the case for virtually all proteins, a variety of changes can be introduced into a wild-type sequence (listed above in GENBANK® entries) without substantially altering the functional (biological) activity of the polypeptides. Such variants are included within the scope of the terms "Ngn3", "Ngn3 protein", etc.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (http://www.ncbi.nlm.nih.gov/). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids without any termination codons. These sequences are usually translatable into a peptide.

Pancreatic endocrine cell: An endocrine cell of pancreatic origin that produces one or more pancreatic hormone, such as insulin, glucagon, somatostatin, or pancreatic polypeptide. Subsets of pancreatic endocrine cells include the α (glucagon producing), β (insulin producing) δ (somatostatin producing) or PP (pancreatic polypeptide producing) cells. Additional subsets produce more than one pancreatic hormone, such as, but not limited to, a cell that produces both insulin and glucagon, or a cell that produces insulin, glucagon, and somatostatin, or a cell that produces insulin and somatostatin.

Pancreas duodenal homeobox protein (Pdx)1: Pdx1 protein is a transcriptional activator of several genes, including insulin, somatostatin, glucokinase, islet amyloid polypeptide, and glucose transporter type 2 (GLUT2). Pdx1 is a nuclear protein is involved in the early development of the pancreas and plays a major role in glucose-dependent regulation of insulin gene expression. Defects in the gene encoding the Pdx1 preotein are a cause of pancreatic agenesis, which can lead to early-onset insulin-dependent diabetes mellitus (NIDDM), as well as maturity onset diabetes of the young type 4 (MODY4). Pdx1 is referred in the art as aliases; pancreatic and duodenal homeobox 1, IDX-1, STF-1, PDX-1, MODY4, Ipfl. Exemplary Pdx1 proteins are shown in GENBANK® Accession No. NM_008814 (mouse) (SEQ ID NO:1 of U.S. Published Patent Application No. 2011/0280842) or GENBANK® Accession No. NP_000200.1 (Human)(SEQ ID NO: 31 of U.S. Published Patent Application No. 2011/0280842), or Gene ID: 3651, which are all incorporated herein by reference. The term Pdx1 also encompasses species variants, homologues, allelic forms, mutant forms, and equivalents thereof, including conservative substitutions, additions, deletions therein not adversely affecting the structure of function. Exemplary nucleic acid sequences are shown in GENBANK® Accession No NM_000209 (human) (SEQ ID NO:34 of U.S. Published Patent Application No. 2011/0280842) or GENBANK® Accession No NM_008814 (mouse)(SEQ ID NO: 37 of U.S. Published Patent Application No. 2011/0280842), which are all incorporated by reference. The term "Pdx1", or "Pdx1 protein" as used herein refers to a polypeptide having a naturally occurring amino acid sequence of a Pdx1 protein or a fragment, variant, or derivative thereof that at least in part retains the ability of the naturally occurring protein to bind to DNA and activate gene transcription of insulin, somatostatin, glucokinase, islet amyloid polypeptide, and glucose transporter type 2 (GLUT2). In addition to naturally-occurring allelic variants of the Pdx1 sequences that may exist in the population, it will be appreciated that, as is the case for virtually all proteins, a variety of changes can be introduced into a wild type sequence (see the listed GENBANK® entries) without substantially altering the functional (biological) activity of the polypeptides. Such variants are included within the scope of the terms "Pdx1", "Pdx1 protein", etc. The listed GENBANK® Accession Nos. and of U.S. Published Patent Application No. 2011/0280842 are incorporated by reference herein.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or a composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Pre-diabetes: A state in which some, but not all, of the criteria for diabetes are met. For example, a subject can have impaired fasting glycaemia or impaired fasting glucose (IFG). Subjects with fasting glucose levels from 110 to 125 mg/dl (6.1 to 6.9 mmol/l) are considered to have impaired fasting glucose. Subjects with plasma glucose at or above 140 mg/dL (7.8 mmol/L), but not over 200 mg/dL (11.1 mmol/L), two hours after a 75 g oral glucose load are considered to have impaired glucose tolerance.

Predisposition for diabetes: A subject that is at high risk for developing diabetes. A number of risk factors are known to those of skill in the art and include: genetic factors (e.g., carrying alleles that result in a higher occurrence of diabetes than in the average population or having parents or siblings with diabetes); overweight (e.g., body mass index (BMI) greater or equal to 25 kg/m·sup.2); habitual physical inactivity, race/ethnicity (e.g., African-American, Hispanic-American, Native Americans, Asian-Americans, Pacific Islanders); previously identified impaired fasting glucose or impaired glucose tolerance, hypertension (e.g., greater or equal to 140/90 mmHg in adults); HDL cholesterol greater or equal to 35 mg/dl; triglyceride levels greater or equal to 250 mg/dl; a history of gestational diabetes or delivery of a baby over nine pounds; and/or polycystic ovary syndrome. See, e.g., "Report of the Expert Committee on the Diagnosis and Classification of Diabetes Mellitus" and "Screening for Diabetes" Diabetes Care 25(1): S5-S24 (2002).

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

The term "polypeptide fragment" refers to a portion of a polypeptide which exhibits at least one useful epitope. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell. An "epitope" is a region of a polypeptide capable of binding an immunoglobulin generated in response to contact with an antigen. Thus, smaller peptides containing the biological activity of insulin, or conservative variants of the insulin, are thus included as being of use.

The term "soluble" refers to a form of a polypeptide that is not inserted into a cell membrane.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Variations in the cDNA sequence that result in amino acid changes, whether conservative or not, should be minimized in order to preserve the functional and immunologic identity of the encoded protein. The immunologic identity of the protein may be assessed by determining if it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80, 90 or even 95% or 98% identical to the native amino acid sequence.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Preventing, treating or ameliorating a disease: "Preventing" a disease (such as type 1 diabetes) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987).

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, such as by genetic engineering techniques. Similarly, a recombinant protein is one encoded for by a recombinant nucleic acid molecule. In addition, a recombinant virus is a virus comprising sequence (such as genomic sequence) that is non-naturally occurring or made by artificial combination of at least two sequences of different origin. The term "recombinant" also includes nucleic acids, proteins and viruses that have been altered solely by addition, substitution, or deletion of a portion of a natural nucleic acid molecule, protein or virus. As used herein, "recombinant AAV" refers to an AAV particle in which a recombinant nucleic acid molecule (such as a recombinant nucleic acid molecule encoding Pdx1 and MafA) has been packaged.

Selectable Marker: A gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select specific cells of interest. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or *Renilla* luciferase) are also of use. The term "selectable marker" as used herein can refer to a gene or to an expression product of the gene, e.g., an encoded protein.

Sequence identity of amino acid sequences: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of proteins, such as MafA or Pdx1 are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus a 13 cell specific binding agent is an agent that binds substantially to a 0 cell, and a pancreatic endocrine cell specific binding agent is an gent that binds substantially only to pancreatic endocrine cells or a subset thereof (and not to pancreatic exocrine cells). Similarly, a pancreatic exocrine cell specific binding agent is an agent that binds substantially to exocrine cells. In one embodiment, the specific binding agent is a monoclonal or polyclonal antibody that specifically binds a type of pancreatic cell.

The term "specifically binds" refers, with respect to a cell, such as a pancreatic endocrine cell, to the preferential association of an antibody or other ligand, in whole or part, with a cell or tissue bearing that antigen and not to cells or tissues lacking that antigen. It is, of course, recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue expressing the target epitope as compared to a cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Subject: Any mammal, such as humans, non-human primates, pigs, sheep, cows, rodents and the like which is to be the recipient of the particular treatment. In two non-limiting examples, a subject is a human subject or a murine subject.

Therapeutic agent: Used in a generic sense, it includes treating agents, prophylactic agents, and replacement agents. A therapeutic agent can be a nucleic acid molecule encoding MafA and Pdx-1, or a vector encoding these factors.

Therapeutically effective amount: A quantity of a specified pharmaceutical or therapeutic agent (e.g. a recombinant AAV) sufficient to achieve a desired effect in a subject, or in a cell, being treated with the agent, such as increasing insulin production. The effective amount of the agent will be dependent on several factors, including, but not limited to the subject or cells being treated, and the manner of administration of the therapeutic composition.

Transduced and Transformed: A virus or vector "transduces" a cell when it transfers nucleic acid into the cell. A cell is "transformed" or "transfected" by a nucleic acid transduced into the cell when the DNA becomes stably replicated by the cell, either by incorporation of the nucleic acid into the cellular genome, or by episomal replication.

Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses {Wolff, J. A., ed, Gene Therapeutics, Birkhauser, Boston, USA (1994)}. In the case of infection by retroviruses, the infecting retrovirus particles are absorbed by the target cells, resulting in reverse transcription of the retroviral RNA genome and integration of the resulting provirus into the cellular DNA. Methods for the introduction of genes into the pancreatic endocrine cells are known (e.g. see U.S. Pat. No. 6,110,743, herein incorporated by reference). These methods can be used to transduce a pancreatic endocrine cell produced by the methods described herein, or an artificial islet produced by the methods described herein.

Genetic modification of the target cell is an indicium of successful transfection. "Genetically modified cells" refers to cells whose genotypes have been altered as a result of cellular uptakes of exogenous nucleotide sequence by transfection. A reference to a transfected cell or a genetically modified cell includes both the particular cell into which a vector or polynucleotide is introduced and progeny of that cell.

Transgene: An exogenous gene supplied by a vector.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like. In some embodiments herein, the vector is an AAV vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Overview of Several Embodiments

Disclosed herein are methods of producing pancreatic beta cells in a subject. These methods include administering to the subject a vector encoding heterologous Pdx1 and MafA, wherein the vector does not encode Neurogenin 3 (Ngn3) and wherein the subject is not administered any other nucleic acid encoding Ngn3. In some embodiments, the vector is administered intraductally into a pancreatic duct of the subject in order to produce pancreatic beta cells in the subject. In additional embodiments, the vector is an adenovirus vector or an adeno-associated virus vector, such as, but not limited to, an adeno-associated virus 8 vector. The subject can be a human or a veterinary subject. In some embodiments, the subject has type I diabetes.

In some embodiments, the method induces pancreatic alpha cells to transform into pancreatic beta cells. In additional embodiments, the pancreatic beta cells are not rejected by the immune system of the subject. Thus, in further embodiments, the subject is not administered an additional immunosuppressive agent.

In some embodiments, the vector, such as the adenovirus vector or adeno-associated virus vector includes a promoter operably linked to a nucleic acid sequence encoding Pdx1 and a nucleic acid sequence encoding MaFA. As noted above, the adenovirus vector or the adeno-associated virus vector does not include a nucleic acid sequence encoding Ngn3. In some embodiments, the promoter is a glucagon promoter. An exemplary glucagon promoter includes or consists of the nucleic acid sequence set forth as SEQ ID NO: 1.

In additional embodiments, the adenovirus vector or the adeno-associated virus vector comprises the promoter operably linked to the nucleic acid sequence encoding Pdx1 and the nucleic acid sequence encoding MaFA, wherein the nucleic acid sequence encoding Pdx1 and the nucleic acid sequence encoding MafA are linked using a connector. An exemplary connector is a 2A connector. The adenovirus or adeno-associated virus vector also can include a nucleic acid sequence encoding a label.

In further embodiments, the vector, such as the adenovirus vector, for example, the adenovirus 8 vector, is administered intraductally using endoscopic retrograde cholangiopancreatography (ERCP).

Compositions for use in any of the methods disclosed herein also are provided. In some embodiments, these compositions include a) a adeno-associated virus vector comprising a promoter operably linked to a nucleic acids encoding Pdx1 and a nucleic acid encoding MafA, wherein the vector does not encode Ngn3; b) a pharmaceutically acceptable carrier; and optionally c) a contrast dye for endoscopic retrograde cholangiopancreatography. In specific non-limiting examples, the dye is included in the composition. Generally, these compositions does not include a nucleic acid encoding Ngn3 (either in the vector or as a separate nucleic acid) and do not include a Ngn3 polypeptide. In some embodiments, the promoter in the adeno-associated virus vector or adenovirus vector is a glucagon promoter. In a specific non-limiting example, the glucagon promoter includes or consists of the nucleic acid sequence set forth as SEQ ID NO: 1.

In additional non-limiting examples, the adeno-associated virus vector is an adeno-associated virus 8 vector. This adeno-associated virus vector includes a promoter, such as a glucagon promoter, operably linked to a nucleic acid sequence encoding Pdx1 and a nucleic acid sequence encoding MafA, wherein the adeno-associated virus vector does not include a nucleic acid sequence encoding Ngn3. In some embodiments, the nucleic acid sequence encoding Pdx1 and a nucleic acid sequence encoding MafA are joined by a connector. The connector can be a 2A connector. The adeno-associated virus vector also can include a nucleic acid sequence encoding a label.

In some embodiments, the contrast dye is a low-osmolar low-viscosity non-ionic dye, a low-viscosity high-osmolar dye, or a dissociable high-viscosity dye. Specific non-limiting examples of a contrast dye are Iopromid, Ioglicinate, and Ioxaglinate.

The composition can be formulated for administration to the pancreatic duct, for example by using endoscopic retrograde cholangiopancreatography (ERCP).

Thus, the use is disclosed of an adenovirus of adeno-associated virus vector comprising a glucagon promoter operably linked to a nucleic acid encoding Pdx1 and a nucleic acid encoding MafA, wherein the vector does not encode Ngn3, and wherein the vector is administered intraductally into a pancreatic duct of the subject, for the production of pancreatic beta cells and/or the treatment of type 1 diabetes in the subject.

Vectors

Disclosed herein are vectors, such as a viral vector, such as a retroviral vector, an adenoviral vector, or an adeno-associated vector (AAV) that encodes MafA and Pdx1. Viral vectors include an attenuated or defective DNA or RNA viruses, including, but not limited to, adenovirus or adeno-associated virus (AAV). Defective viruses, that entirely or almost entirely lack viral genes, can be used. Use of defective viral vectors allows for administration to specific cells without concern that the vector can infect other cells. In some examples, the vector is an attenuated adenovirus vector, such as the vector described by Stratford-Perricaudet et al. (*J. Clin. Invest.*, 90:626-630 1992; La Salle et al., *Science* 259:988-990, 1993); and a defective adeno-associated virus vector (Samulski et al., *J. Virol.*, 61:3096-3101, 1987; Samulski et al., *J. Virol.*, 63:3822-3828, 1989; Lebkowski et al., *Mol. Cell. Biol.*, 8:3988-3996, 1988).

Suitable vectors are known in the art, and include viral vectors such as retroviral, lentiviral, adenoviral vectors, and AAV. In specific, non-limiting examples, the vector is a lentiviral vector, gammaretroviral vector, self-inactivating retroviral vector, adenoviral vector, or adeno-associated vector (AAV).

Adenoviral vectors and/or adeno-associated viral vectors can be used in the methods disclosed herein. AAV belongs to the family Parvoviridae and the genus Dependovirus. AAV is a small, non-enveloped virus that packages a linear, single-stranded DNA genome. Both sense and antisense strands of AAV DNA are packaged into AAV capsids with equal frequency. In some embodiments the AAV DNA includes a nucleic acid encoding Pdx1 and MafA, but does not include a nucleic acid encoding Ngn3. Further provided are recombinant vectors, such as recombinant adenovirus vectors and recombinant adeno-associated virus (rAAV) vectors comprising a nucleic acid molecule disclosed herein. In some embodiments, the AAV is rAAV8 and/or AAV2. However, the AAV serotype can be any other suitable AAV serotype, such as AAV1, AAV2, AAV3, AAV4, AAV5, AAV6, AAV7, AAV9, AAV10, AAV11 or AAV12, or a hybrid of two or more AAV serotypes (such as, but not limited to AAV2/1, AAV2/7, AAV2/8 or AAV2/9).

The AAV genome is characterized by two inverted terminal repeats (ITRs) that flank two open reading frames (ORFs). In the AAV2 genome, for example, the first 125 nucleotides of the ITR are a palindrome, which folds upon itself to maximize base pairing and forms a T-shaped hairpin structure. The other 20 bases of the ITR, called the D sequence, remain unpaired. The ITRs are cis-acting sequences important for AAV DNA replication; the ITR is the origin of replication and serves as a primer for second-strand synthesis by DNA polymerase. The double-stranded DNA formed during this synthesis, which is called replicating-form monomer, is used for a second round of self-priming replication and forms a replicating-form dimer. These double-stranded intermediates are processed via a strand displacement mechanism, resulting in single-stranded DNA used for packaging and double-stranded DNA used for transcription. Located within the ITR are the Rep binding elements and a terminal resolution site (TRS). These features are used by the viral regulatory protein Rep during AAV replication to process the double-stranded intermediates. In addition to their role in AAV replication, the ITR is also essential for AAV genome packaging, transcription, negative regulation under non-permissive conditions, and site-specific integration (Daya and Berns, *Clin Microbiol Rev* 21(4):583-593, 2008). In some embodiments, these elements are included in the AAV vector.

The left ORF of AAV contains the Rep gene, which encodes four proteins—Rep78, Rep 68, Rep52 and Rep40. The right ORF contains the Cap gene, which produces three viral capsid proteins (VP1, VP2 and VP3). The AAV capsid contains 60 viral capsid proteins arranged into an icosahedral symmetry. VP1, VP2 and VP3 are present in a 1:1:10 molar ratio (Daya and Berns, *Clin Microbiol Rev* 21(4):583-593, 2008). In some embodiments, these elements are included in the AAV vector.

AAV vectors can be used for gene therapy. Exemplary AAV of use are AAV2, AAV5, AAV6, AAV8 and AAV9. Adenovirus, AAV2 and AAV8 are capable of transducing cells in the pancreas. Thus, any of a rAAV2 or rAAV8 vector can be used in the methods disclosed herein. However, rAAV6 and rAAV9 vectors are also of use.

Although AAV infects humans and some other primate species, it is not known to cause disease and elicits a very mild immune response. Gene therapy vectors that utilize AAV can infect both dividing and quiescent cells and persist in an extrachromosomal state without integrating into the genome of the host cell. AAV8 preferentially infects cells of the pancreas. Because of the advantageous features of AAV, the present disclosure contemplates the use of an rAAV for the methods disclosed herein.

AAV possesses several additional desirable features for a gene therapy vector, including the ability to bind and enter target cells, enter the nucleus, the ability to be expressed in the nucleus for a prolonged period of time, and low toxicity.

AAV can be used to transfect cells, and suitable vector are known in the art, see for example, U.S. Published Patent Application No. 2014/0037585, incorporated herein by reference. Methods for producing rAAV suitable for gene therapy are well known in the art (see, for example, U.S. Published Patent Application Nos. 2012/0100606; 2012/0135515; 2011/0229971; and 2013/0072548; and Ghosh et al., Gene Ther 13(4):321-329, 2006), and can be utilized with the methods disclosed herein.

In some embodiments, the vector is an rAAV8 vector, an rAAV6 vector, or an rAAV9 vector. AAV8 vectors are disclosed, for example, in U.S. Pat. No. 8,692,332, which is incorporated by reference herein. An exemplary AAV8 nucleic acid sequence is shown in FIG. 1 and SEQ ID NO: 1 of U.S. Pat. No. 8,692,332. It is disclosed that AAV nucleic acid sequence can be greater than about 90%, 95%, 98% or 99% identical to this nucleic acid sequence. The location and sequence of the capsid, rep 68/78, rep 40/52, VP1, VP2 and VP3 are disclosed in this U.S. Pat. No. 8,692,332. The location and hypervariable regions of AAV8 are also provided.

The vectors of use in the methods disclosed herein can contain nucleic acid sequences encoding an intact AAV capsid which may be from a single AAV serotype (e.g., AAV2, AAV, 6, AAV8 or AAV9). As disclosed in U.S. Pat. No. 8,692,332, vectors of use can also can be recombinant, and thus can contain sequences encoding artificial capsids which contain one or more fragments of the AAV8 capsid fused to heterologous AAV or non-AAV capsid proteins (or fragments thereof). These artificial capsid proteins are selected from non-contiguous portions of the AAV2, AAV6, AAV8 or AAV9 capsid or from capsids of other AAV serotypes. For example, a rAAV vector may have a capsid protein comprising one or more of the AAV8 capsid regions selected from the VP2 and/or VP3, or from VP1, or fragments thereof selected from amino acids 1 to 184, amino acids 199 to 259; amino acids 274 to 446; amino acids 603 to 659; amino acids 670 to 706; amino acids 724 to 738 of the AAV8 capsid, see SEQ ID NO: 2 of U.S. Pat. No. 8,692,332. In another example, it may be desirable to alter the start codon of the VP3 protein to GTG. Alternatively, the rAAV may contain one or more of the AAV serotype 8 capsid protein hypervariable regions, for example aa 185-198; aa 260-273; aa447-477; aa495-602; aa660-669; and aa707-723 of the AAV8 capsid set forth in SEQ ID NO: 2 of U.S. Pat. No. 8,692,332.

In some embodiments, a recombinant adeno-associated virus (rAAV) is generated having an AAV serotype 8 capsid. To produce the vector, a host cell which can be cultured that contains a nucleic acid sequence encoding an adeno-associated virus (AAV) serotype 8 capsid protein, or fragment thereof, as defined herein; a functional rep gene; a minigene composed of, at a minimum, AAV inverted terminal repeats (ITRs) and a transgene, such as a transgene encoding Pdx1 and MafA; and sufficient helper functions to permit packaging in the AAV8 capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art. In some embodiments, a stable host cell will contain the required component(s) under the control of an inducible promoter. However, the required component(s) can be under the control of a constitutive promoter. Examples of suitable inducible and constitutive promoters are provided below. Similar methods can be used to generate a rAAV2, rAAV6 or rAAV9 vector and.or virion.

In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing a rAAV can be delivered to the packaging host cell in the form of any genetic element which transfer the sequences carried thereon. The selected genetic element may be delivered by any suitable method, including those described herein. The methods used to construct vectors are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, J. Virol., 70:520-532 (1993) and U.S. Pat. No. 5,478,745. In some embodiments, selected AAV components can be readily isolated using techniques available to those of skill in the art from an AAV serotype, including AAV8. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GENBANK®.

The adenovirus and AAV vectors disclosed herein include a promoter operably linked to a nucleic acid encoding PDx1 and MafA, but do not include a nucleic acid encoding Ngn3. In some embodiments, the promoter is a glucagon promoter, such as a human or a mouse glucagon promoter. An exemplary glucagon promoter includes, or consists of:

AAAAAATACCAGATAATTTCCTGTTAGCATCAGCTATCTTGGATGTTTAA

TCTTCATTTTGCTCCATCCTTTCTGCCTGAATTCCATTTATTAAAACAGA

ACACATAGGGGTTTAATCAATATCCTTAAATTTTCCACAAACATAACATA

AATAAACTCCACGTTGTGAGGAAGAGAGGATTTTTAATACATATGTGTTG

AATGTATGATCATTATTTAGATAAATGAATGACTGAAGTGATTGTTATAT

TCAGGTAAATTCATCATGGCTAGGTAGCAAACCAAAGACTTGTAAGAACC

TCAAATGAGGACATGCACAAAACAGGGATGGCCATGGGCTACGTAATTTC

AAGGTCTTTTGTCTTCAACGTCAAAATTCACTTTAGAGAACTTAAGTGAT

TTTCATGCGTGATTGAAAGTAGAAGGTGGATTTCCAAGCTGCTCTCTCCA

TTCCCAACC (SEQ ID NO: 1, human short glucagon promoter).

An additional exemplary glucagon promoter includes, or consists of:

```
TCAGTGACATCATGCGGTTGGTTATATTAGAATATTGGAATCTAGTTAGG
AAATGTTGTGATGAGTTTGCAATATGGAATAAAATTTTTATTTTAGAAAA
GACATTTACCAACCCCTCTCATTTTACAAATAAGGAGGCAGAGACACAAA
GAGAATGCGTGACTTGACCAAGGTCCACAGCTGGTCAATAACAGCAAAAC
TAAAATCAAATTATGCCAACACTACTTCTTATGCTGTCTTTCCAGATTAT
TTACCATTTTCTATTTCTCTACAGTGACCAGAATCATTTCTGCTAAATG
TCACAGATCATTAAAGCCTGTGTGTCCAGTCACAAAACTCAGGAAACGTG
AAAATATGCATCTCATCTCAACAGTTTTCCTCATATCTCATTCTTTTGTA
ACTTAGTACCCCACTCTCTTATCAGTAAAATTAGATTTTAAATATATATT
AGAAGGAAAAAAATACCAGATAATTTCCTGTTAGCATCAGCTATCTTGGA
TGTTTAATCTTCATTTTGCTCCATCCTTTCTGCCTGAATTCCATTTATTA
AAACAGAACACATAGGGGTTTAATCAATATCCTTAAATTTTCCACAAACA
TAACATAAATAAACTCCACGTTGTGAGGAAGAGAGGATTTTTAATACATA
TGTGTTAATGAATGATCATTATTTAGATAAATGAATGACTGAAGTGATT
GTTATATTCAGGTAAATTCATCATGGCTAGGTAGCAAACCAAAGACTTGT
AAGAACCTCAAATGAGGACATGCACAAAACAGGGATGGCCATGGGCTACG
TAATTTCAAGGTCTTTTGTCTTCAACGTCAAAATTCACTTTAGAGAACTT
AAGTGATTTTCATGCGTGATTGAAAGTAGAAGGTGGATTTCCAAGCTGCT
CTCTCCATTCCCAACCAAAAAAAAAAAAAAAGATACAAGAGTGCATAAA
AAGTTTCCAGGTCTCTAAGGTCTCTCACCCAATATAAGCATAGAATGCAG
ATGAGCAAAGTGAGTGGGAGAGGGAAGTCATTTGTAACAAAAACTCATTA
TTTACAGATGAGAAATTTATATTGTCAGCGTAATATCTGTGAGGCTAAAC
AGAGCTGGAGAGTATATAAAAGCAGTGCGCCTTGGTGCAGAAGTACAGAG
CTTAGGACACAGAGCACATCAAAAGTTCCCAAAGAGGGCTTGCTCTCTCT
TCACCTGCTCTGTTCTACAGCACACTACCAGAAGGTAAGATG
```

(SEQ ID NO: 2, human long glucagon promoter).

Yet another exemplary glucagon promoter, includes, or consists of:

```
GAGATATAGCCAAATACCAAATCAAGGGATAAGACCCTCAAATGAGACT
AGGCTCATTTGACGTCAAAATTCACTTGAGAGAACTTTAGCAGTTTTTC
GTGCCTGACTGAGACCGAAGGGTGGATCTCCAAACTGCCCTTTCCATTC
CCAAACAGAAAGGCACAAGAGTAAATAAAATGTTTCCGGGCCTCTGCGG
TCTCAACCCGGTATCAGCGTAAAAAGCAGATGAGCAAAGTGAGTGGGCG
AGTGAAATCATTTGAACAAAACCCCATTATTTACAGATGAGAAATTTAT
ATTGTCAGCGTAATATCTGCAAGGCTAAACAGCCTGGAGAGCATATAAA
AGCACAGCACCCTGGTGCAGAAGGGCAGAGCTTGGGCCCAGGACACACT
CAAAGTTCCCAAGGGGACTCCCTCTGTCTACACCTGTTCGCAGCTCAGG
CTCACAAGGCAGAAAAAAAA (SEQ ID NO: 3, mouse
glucagon promoter)
```

Any of these promoters can be utilized in the methods disclosed herein. Other promoters of use include:
PP Promoter:

```
                                              (SEQ ID NO: 4)
TAGCCAAAAAGTGGGAAATTATAACAATACTTGACGGCCCCACTTAGGAA
AAAAAACAGTCCAGGTTTGGAGTTAAATTTTGGGGTCTGACTGGCTGTGG
GGTTTGGGGCCAGTGATTTGACATCTCTGAGCAGATTTCAGACCCTGAAT
CTGTAAAATGGGTTGTTGTGGGGATTTAGTGAGGTGACTGAGCTGGCAGC
ACTTTGGAAAATGTGAGGCTTTACAAATGAAGCTGGTTTTTAGCACTTCC
TTGGAATGGGGGCTCTGAGATGGGGAGGGAAATGGATACTGGAAACCGGC
ACCCCCCTCAACATTTCCCCTGAACCTAGGCACATGAGTCCATTCTGCAT
CCTATGCACCCACCAAATGGGTTTCTCCAAGCCTGGCACCCCACTCCTTT
CCACCTTGCCTGAGGACCCTGAGGCCCCTTCCCTCTTCCCACCTTGTTCT
AGTTGCAAGCTGCAGAGGATGGCCTGAGTTTCCATTCTTCAGCCTGGAGG
CTCTGGCTGTAGCCTCAGTCTTCCAGCTGCAGCCTCAATCTTCTGCCCCA
AGAGAATCCGTTGGATGATTTGGGTTGATCTTTGGGAGGCAGGAGAGCTA
GTTCCAAGGCCTGTGACCAAAACCTTTCAGTCACTCTCGAGTCCCAGAAC
CCCATCTTTCTTGAACCAAGCCTGCTCTGGTGCCCAAAGGGAAGGGGTGT
CAGTGATGGGGCCCACAGGAGACTTTTACTGTGGTCCAGTTTTATCTGT
TATGCTGCTGGTCTGGCACCCACAGAACTGCCCTGTCCCCCTCCCGTCTC
TGGCCTCAGTACTGGCGTTGCCAGTATGAGGAGACAGTGAGAGGAGGGGT
GAGGGCTTCGGAGTGAGAGAGGCTGACAGGAGGCGGGGACTCTGGGGGGC
TGAGGACTATAAAGCGGCCCAGCCGAGGGCAGGGGCCCATCCGGCCTGAG
GCAGGTGCTCGCTTGGTCTAGTGCCCATTTACTCTGGACTCCGGGTAAGT
GGGCTCACGCCTGCCTGGGGCTCTGGGGGCCTCCCCCAGGCTGGGGCCTG
GGATGGAGAGGAGGTGGTGCTTTGCAGGGCCAGGGGCCTTGGGAGGCCTA
AGGTCCTGCTTGGGTCTTGCTTTCTGCATCTGGACAGACCTGTCACGCTA
GAAGAGCCGTCTGCTGACTGCACGTGTGTGTGCACACTCGTGTGCATGGC
CTGTGAACTGGAATGTGTGACTGTGACCTTGTGAGTGAACTGGGGTCCCT
GTGTGAGTGCCTTTGCTGGTCTGTGCAGGACGACATGGACAATAGCGTCT
TCTCCAGGACCGATATCTGTGTCTCTATCGCAGGGTGGAGGGCCAGCACC
CACAAGGCCATGGTTTCTGTCCTTGGCTTCCCGAGTTCATTCTGTGTCCC
CCACCCTGTGGGTGACCTGCATGCCCTTATTCCCACTAGCTGCTGCCTCC
TGGGAGCCATGAGGCCCTAGATGTCATCAGTCCCGTGTCTCCAGGACTCA
CATCCCCATTTTAACTAACTTGCGAGGCCCTGGCTTGCTGGGCTGCTCAC
AGGACAGGCTGTCCGTGCCTTCAGAGCAGTGTCTAGGAGGTGGAGTGGCC
AGCTTGGAGTGGCCCTTTGCTCTGCCCCCTTGTCCCCAAGCTTGGAGAAA
TGGATGATGGGCTAAGGGGCTGGATAGTTGGGCCCTGCTTCCTAGGCACG
```

```
GGAAAATCTGCAGGCCCGGGCACTCCACCTCCCCTCTGCTTGCTCCTCAG

ATGGCTGCCGCACGCCTCTGCCTCTCCCTGCTGCTCCTGTCCACCTGCGT

GGCTCTGTTACTACAGCCACTGCTGGGTGCCCAGGGAGCCCCACTGGAGC

CAGTGTACCCAGGGGACAATGCCACACCAGAGCAGATGGCCCAGTATGCA

GCTGATCTCCGTAGATACATCAACATGCTGACCAGGCCTAGGTGTGTGCC

ACAGTTGGGGAGAGAGATCCCAGCCCCTGGGACCCTGGGCCCACTCCACA

TTCCTGGCCACACCCTATCCCCAGCCCCAGCCCCAGCCCCTTCTAGGCC

TGCTCTTGGGAAACAGGGCATCTGTCGCTCAACAGGCCAGACCAATGTGC

CTGGGCAAGATGGTGTCCTACAGGTCAGATATGAAACAGGTGGGCTGGCA

CCTGGGCACAGTGCTTGCCCCTGCTGCCTCTTCCCTCCCAGGTATGGGAA

AAGACACAAAGAGGACACGCTGGCCTTCTCGGAGTGGGGGTCCCCGCATG

CTGCTGTCCCCAGGTGAGTTTGACTCCCTGCCCTGTCTGTCCAGGCTCCC

TGGGGCTGAAATGGGGGTGGTGGGACTGAATCAGGGCTTGGAAAGGTGTA

GTGGGGGTGGAAGAGGGAGAACAGGAGCCCAGGGCCAGCGTGAGGCCTC

CTGAGGGCACGAGGCCTACCCCCTACACTGCCATGTTCTGCCCTGTCCTC

ACAGGGAGCTCAGCCCGCTGGACTTATAATGCCACCTTCTGTCTCCTACG

ACTCCATGAGCAGCGCCAGC
```

Human Somatostatin Promoter:

```
                                           (SEQ ID NO: 5)
GGGATCATCTCGTCCATGCTAGGAAATTAGCTGGTCCTTCCTCAGTAAG

GAACTATTTAGATAAAAGCAGTCAGAACTCTGGCCTGAACAGTAAACAT

TTAACCAGAGTTCAATCAGAATTCAAGGACAGGTTTTCTTAAACTTTCT

TTGTTTCTAGGAGATCAGGCAGAGCTGAATTTAACCAAGAATCTTTTGA

TCCTTTCCACATATAGATATACAATAGTGGTCACATATGTTCTGGGAGT

TCCTAGACCTTATATGTCTAAACTGGGGCTTCCTGACATAAAACTATGC

TTACCGGCCAGGAATCTGTTAGAAAACTCAGAGCTCAGTAGAAGGAACA

CTGGCTTTGGAATGTGGAGGTCTGGTTTTGCTCAAAGTGTGCAGTATGT

GAAGGAGAACAATTTACTGACCATTACTCTGCCTTACTGATTCAAATTC

TGAGGTTTATTGAATAATTTCTTAGATTGCCTTCCAGCTCTAAATTTCT

CAGCACCAAAATGAAGTCCATTTCAATCTCTCTCTCTCTTTCCCTCC

CGTACATATACACACTCATACATATATATGGTCACAATAGAAAGGCA

GGTAGATCAGAAGTCTCAGTTGCTGAGAAAGAGGGAGGGAGGGTGAGCC

AGAGGTACCTTCTCCCCCATTGTAGAGAAAAGTGAAGTTCTTTTAGAGC

CCCGTTACATCTTCAAGGCTTTTTATGAGATAATGGAGGAAATAAAGAG

GGCTCAGTCCTTCTACTGTCCATATTTCATTCTCAAATCTGTTATTAGA

GGAATGATTCTGATCTCCACCTACCATACACATGCCCTGTTGCTTGTTG

GGCCTTCCTAAAATGTTAGAGTATGATGACAGATGGAGTTGTCTGGGTA

CATTTGTGTGCATTTAAGGGTGATAGTGTATTTGCTCTTTAAGAGCTGA

GTGTTTGAGCCTCTGTTTGTGTGTAATTGAGTGTGCATGTGTGGGAGTG

AAATTGTGGAATGTGTATGCTCATAGCACTGAGTGAAAATAAAAGATTG

TATAAATCGTGGGCATGTGGAATTGTGTGTGCCTGTGCGTGTGCAGTA

TTTTTTTTTTTTTAAGTAAGCCACTTTAGATCTTGTCACCTCCCCTGTC

TTCTGTGATTGATTTTGCGAGGCTAATGGTGCGTAAAAGGGCTGGTGAG

ATCTGGGGCGCCTCCTAGCCTGACGTCAGAGAGAGAGTTTAAAACAGA

GGGAGACGGTTGAGAGCA
```

Alternatively, the promoter can be any promoter of interest, including constitutive and inducible promoters. Exemplary promoter sequences are provided below.

CAG Promoter:

```
                                           (SEQ ID NO: 6)
GTCGACATTGATTATTGACTAGTTATTAATAGTAATCAATTACGGGGTCA

TTAGTTCATAGCCCATATATGGAGTTCCGCGTTACATAACTTACGGTAAA

TGGCCCGCCTGGCTGACCGCCCAACGACCCCCGCCCATTGACGTCAATAA

TGACGTATGTTCCCATAGTAACGCCAATAGGGACTTTCCATTGACGTCAA

TGGGTGGACTATTTACGGTAAACTGCCCACTTGGCAGTACATCAAGTGTA

TCATATGCCAAGTACGCCCCCTATTGACGTCAATGACGGTAAATGGCCCG

CCTGGCATTATGCCCAGTACATGACCTTATGGGACTTTCCTACTTGGCAG

TACATCTACGTATTAGTCATCGCTATTACCATGGGTCGAGGTGAGCCCCA

CGTTCTGCTTCACTCTCCCCATCTCCCCCCCCTCCCCACCCCCAATTTTG

TATTTATTTATTTTTTAATTATTTTGTGCAGCGATGGGGGCGGGGGGGG

GGGGGCGCGCGCCAGGCGGGGCGGGGCGGGGCGAGGGGCGGGGCGGGGCG

AGGCGGAGAGGTGCGGCGGCAGCCAATCAGAGCGGCGCGCTCCGAAAGTT

TCCTTTTATGGCGAGGCGGCGGCGGCGGCGGCCCTATAAAAAGCGAAGCG

CGCGGCGGGCGGGAGTCGCTGCGTTGCCTTCGCCCCGTGCCCCGCTCCGC

GCCGCCTCGCGCCGCCCGCCCCGGCTCTGACTGACCGCGTTACTCCCACA

GGTGAGCGGGCGGGACGGCCCTTCTCCTCCGGGCTGTAATTAGCGCTTGG

TTTAATGACGGCTCGTTTCTTTTCTGTGGCTGCGTGAAAGCCTTAAAGGG

CTCCGGGAGGGCCCTTTGTGCGGGGGGGAGCGGCTCGGGGGGTGCGTGCG

TGTGTGTGTGCGTGGGGAGCGCCGCGTGCGGCCCGCGCTGCCCGGCGGCT

GTGAGCGCTGCGGGCGCGGCGCGGGCTTTGTGCGCTCCGCGTGTGCGCG

AGGGGAGCGCGGCCGGGGCGGTGCCCCGCGGTGCGGGGGGCTGCGAGG

GGAACAAAGGCTGCGTGCGGGGTGTGTGCGTGGGGGGGTGAGCAGGGGGT

GTGGGCGCGGCGGTCGGGCTGTAACCCCCCCCTGCACCCCCCTCCCCGAG

TTGCTGAGCACGGCCCGGCTTCGGGTGCGGGGCTCCGTGCGGGGCGTGGC

GCGGGGCTCGCCGTGCCGGGCGGGGGTGGCGGCAGGTGGGGGTGCCGGG

CGGGGCGGGGCCGCCTCGGGCCGGGGAGGGCTCGGGGGAGGGGCGCGGCG

GCCCCGGAGCGCCGGCGGCTGTCGAGGCGCGGCGAGCCGCAGCCATTGCC

TTTTATGGTAATCGTGCGAGAGGGCGCAGGGACTTCCTTTGTCCCAAATC

TGGCGGAGCCGAAATCTGGGAGGCGCCGCCGCACCCCCTCTAGCGGGCGC

GGGCGAAGCGGTGCGGCGCCGGCAGGAAGGAAATGGGCGGGAGGGCCTT

CGTGCGTCGCCGCGCCGCCGTCCCCTTCTCCATCTCCAGCCTCGGGGCTG
```

-continued
CCGCAGGGGGACGGCTGCCTTCGGGGGGGACGGGGCAGGGCGGGGTTCGG
CTTCTGGCGTGTGACCGGCGGCTCTAGAGCCTCTGCTAACCATGTTCATG
CCTTCTTCTTTTTCCTACAGCTCCTGGGCAACGTGCTGGTTATTGTGCTG
TCTCATCATTTTGGCAAAGAATT Human Elongation Factor (EF1) Promoter:

(SEQ ID NO: 7)
GGCTCCGGTGCCCGTCAGTGGGCAGAGCGCACATCGCCCACAGTCCCCGA
GAAGTTGGGGGGAGGGGTCGGCAATTGAACCGGTGCCTAGAGAAGGTGGC
GCGGGGTAAACTGGGAAAGTGATGTCGTGTACTGGCTCCGCCTTTTTCCC
GAGGGTGGGGGAGAACCGTATATAAGTGCAGTAGTCGCCGTGAACGTTCT
TTTTCGCAACGGGTTTGCCGCCAGAACACAGGTAAGTGCCGTGTGTGGTT
CCCGCGGGCCTGGCCTCTTTACGGGTTATGGCCCTTGCGTGCCTTGAATT
ACTTCCACTGGCTGCAGTACGTGATTCTTGATCCCGAGCTTCGGGTTGGA
AGTGGGTGGGAGAGTTCGAGGCCTTGCGCTTAAGGAGCCCCTTCGCCTCG
TGCTTGAGTTGAGGCCTGGCCTGGGCGCTGGGGCCGCCGCGTGCGAATCT
GGTGGCACCTTCGCGCCTGTCTCGCTGCTTTCGATAAGTCTCTAGCCATT
TAAAATTTTTGATGACCTGCTGCGACGCTTTTTTTCTGGCAAGATAGTCT
TGTAAATGCGGGCCAAGATCTGCACACTGGTATTTCGGTTTTTGGGGCCG
CGGGCGGCGACGGGGCCCGTGCGTCCCAGCGCACATGTTCGGCGAGGCGG
GGCCTGCGAGCGCGGCCACCGAGAATCGGACGGGGGTAGTCTCAAGCTGG
CCGGCCTGCTCTGGTGCCTGGCCTCGCGCCGCCGTGTATCGCCCCGCCCT
GGGCGGCAAGGCTGGCCCGGTCGGCACCAGTTGCGTGAGCGGAAAGATGG
CCGCTTCCCGGCCCTGCTGCAGGGAGCTCAAAATGGAGGACGCGGCGCTC
GGGAGAGCGGGCGGGTGAGTCACCCACACAAAGGAAAAGGGCCTTTCCGT
CCTCAGCCGTCGCTTCATGTGACTCCACGGAGTACCGGGCGCCGTCCAGG
CACCTCGATTAGTTCTCGAGCTTTTGGAGTACGTCGTCTTTAGGTTGGGG
GGAGGGGTTTTATGCGATGGAGTTTCCCCACACTGAGTGGGTGGAGACTG
AAGTTAGGCCAGCTTGGCACTTGATGTAATTCTCCTTGGAATTTGCCCTT
TTTGAGTTTGGATCTTGGTTCATTCTCAAGCCTCAGACAGTGGTTCAAAG
TTTTTTTCTTCCATTTCAGGTGTCGTGA

Beta Globin Promoter:

(SEQ ID NO: 8)
GATCTCTATTTATTTAGCAATAATAGAGAAAGCATTTAAGAGAATAAAG
CAATGGAAATAAGAAATTTGTAAATTTCCTTCTGATAACTAGAAATAGA
GGATCCAGTTTCTTTTGGTTAACCTAAATTTTATTTCATTTTATTGTTT
TATTTTATTTTATTTTATTTTATTTTGTGTAATCGTAGTTTCAGAGTGT
TAGAGCTGAAAGGAAGAAGTAGGAGAAACATGCAAAGTAAAAGTATAAC
ACTTTCCTTACTAAACCGACATGGGTTTCCAGGTAGGGGCAGGATTCAG
GATGACTGACAGGGCCCTTAGGGAACACTGAGACCCTACGCTGACCTCA
TAAATGCTTGCTACCTTTGCTGTTTTAATTACATCTTTTAATAGCAGGA
AGCAGAACTCTGCACTTCAAAAGTTTTTCCTCACCTGAGGAGTTAATTT
AGTACAAGGGGAAAAAGTACAGGGGGATGGGAGAAAGGCGATCACGTTG
GGAAGCTATAGAGAAAGAAGAGTAAATTTTAGTAAAGGAGGTTTAAACA
AACAAAATATAAAGAGAAATAGGAACTTGAATCAAGGAAATGATTTTAA
AACGCAGTATTCTTAGTGGACTAGAGGAAAAAAATAATCTGAGCCAAGT
AGAAGACCTTTTCCCCTCCTACCCCTACTTTCTAAGTCACAGAGGCTTT
TTGTTCCCCCAGACACTCTTGCAGATTAGTCCAGGCAGAAACAGTTAGA
TGTCCCCAGTTAACCTCCTATTTGACACCACTGATTACCCCATTGATAG
TCACACTTTGGGTTGTAAGTGACTTTTTATTTATTTGTATTTTTGACTG
CATTAAGAGGTCTCTAGTTTTTTATCTCTTGTTTCCCAAAACCTAATAA
GTAACTAATGCACAGAGCACATTGATTTGTATTTATTCTATTTTTAGAC
ATAATTTATTAGCATGCATGAGCAAATTAAGAAAAACAACAACAAATGA
ATGCATATATATGTATATGTATGTGTATATATACACACATATATATA
TATATTTTTCTTTTCTTACCAGAAGGTTTTAATCCAAATAAGGAGAAG
ATATGCTTAGAACCGAGGTAGAGTTTTCATCCATTCTGTCCTGTAAGTA
TTTTGCATATTCTGGAGACGCAGGAAGAGATCCATCTACATATCCCAAA
GCTGAATTATGGTAGACAAAACTCTTCCACTTTTAGTGCATCAACTTCT
TATTTGTGTAATAAGAAAATTGGGAAAACGATCTTCAATATGCTTACCA
AGCTGTGATTCCAAATATTACGTAAATACACTTGCAAAGGAGGATGTTT
TTAGTAGCAATTTGTACTGATGGTATGGGGCCAAGAGATATATCTTAGA
GGGAGGGCTGAGGGTTTGAAGTCCAACTCCTAAGCCAGTGCCAGAAGAG
CCAAGGACAGGTACGGCTGTCATCACTTAGACCTCACCCTGTGGAGCCA
CACCCTAGGGTTGGCCAATCTACTCCCAGGAGCAGGGAGGGCAGGAGCC
AGGGCTGGGCATAAAAGTCAGGGCAGAGCCATCTATTGCTTACATTTGC
TTCTGACACAACTGTGTTCACTAGCAACCTCAAACAGACAC

CMV Promoter (SEQ ID NO: 9)
TCAATATTGG CCATTAGCCA TATTATTCAT TGGTTATATA
GCATAAATCA ATATTGGCTATTGGCCATTG CATACGTTGT
ATCTATATCA TAATATGTAC ATTTATATTG
GCTCATGTCCAATATGACCG CCATGTTGGC ATTGATTATT
GACTAGTTAT TAATAGTAAT CAATTACGGGGTCATTAGTT
CATAGCCCAT ATATGGAGTT CCGCGTTACA TAACTTACGG
TAAATGGCCCGCCTGGCTGA CCGCCCAACG ACCCCCGCCC
ATTGACGTCA ATAATGACGT ATGTTCCCAT AGTAACGCCA
ATAGGGACTT TCCATTGACG TCAATGGGTG GAGTATTTAC
GGTAAACTGCCCACTTGGCA GTACATCAAG TGTATCATAT
GCCAAGTCCG CCCCCTATTG ACGTCAATGACGGTAAATGG
CCCGCCTGGC ATTATGCCCA GTACATGACC TTACGGGACT
TTCCTACTTGGCAGTACATC TACGTATTAG TCATCGCTAT

```
TACCATGGTG ATGCGGTTTT GGCAGTACACCAATGGGCGT

GGATAGCGGT TTGACTCACG GGGATTTCCA AGTCTCCACC

CCATTGACGT CAATGGGAGT TTGTTTTGGC ACCAAAATCA

ACGGGACTTT CCAAAATGTC GTAATAACCCCGCCCCGTTG

ACGCAAATGG GCGG
```

Other promoters include a cell specific promoters, housekeeping gene promoters (GAPDH, Actin, Cyclophilin), or chimeric promoters with viral enhancers with gene promoters. In some embodiments, the promoter in a non-viral promoter, in other embodiments, the promoter is a viral promoter.

One of skill in the art will readily appreciate that variants of these promoters can be used, such as promoters at least 95%, 96%, 97%, 98%, 99% identical to one of SEQ ID NO: 1, SEQ ID NO: 2, or SEQ ID NO: 3, provided the promoter functions, such that a heterologous nucleic acid operably linked to the promoter is expressed when transferred into a in a host cell that expresses glucagon. Similarly, promoters at least 95%, 96%, 97%, 98%, 99% identical to one of SEQ ID NO: 4 or SEQ ID NO: 5, provided the promoter functions, such that a heterologous nucleic acid operably linked to the promoter is expressed when transferred into a in a host cell Promoters at 95%, 96%, 97%, 98%, 99% identical to one of SEQ NOs: 6-9, provided the promoter functions, such that a heterologous nucleic acid operably linked to the promoter is expressed when transferred into a in a host cell. In additional embodiments, the promoter can include at most 15, 14, 13, 12, 11, 10, 9, 8, 7, 6, 5, 4, 3, 2, 1 nucleic acid substitutions in any one of SEQ NOs: 1-9, provided the promoter functions, such that a heterologous nucleic acid operably linked to the promoter can be expressed when transferred into a in a host cell. Additional nucleotides can be added, provided the promoter functions, such that a heterologous nucleic acid operably linked to the promoter is expressed when transferred into a in a host cell. The promoter can include the nucleic acid sequence set forth as SEQ ID NO: 1, and 10, 20, 30, 40, 50, 60, 70, 80, 90, 100, 200, 300, 400, 500, 600, 700, or 800 nucleotides of SEQ ID NO: 2, provided the promoter functions to provide transcription of a nucleic acid encoding a heterologous protein, such as Pdx1 and/or MafA. Similarly, promoter can include the nucleic acid sequence set forth as SEQ ID NO: 3, and 10, 20, 30, 40, 50, 60, 70, 80, 90, 100, 200, 300, 400, 500, 600, 700, or 800 nucleotides of SEQ ID NO: 2, or the full-length mouse glucagon promoter, provided the promoter functions to provide transcription of a nucleic acid encoding a heterologous protein, such as Pdx1 and/or MafA Thus, in specific examples, the heterologous nucleic acid encodes Pdx1 and/or MafA. In additional examples, the heterologous nucleic acid encodes Pdx1 and/or MafA and does not encode Ngn3. In some embodiments, the promoter functions such that both MafA and/or Pdx1 transcripts are produced. In specific non-limiting examples, the promoter is operably linked to a nucleic acid encoding MafA and a nucleic acid encoding Pdx1, but is not operably linked to a nucleic acid encoding Ngn3, and a vector including the promoter and the heterologous nucleic acid, such as rAAV vector, does not include a nucleic acid encoding Ngn3.

In some embodiments, the vectors encode a MafA amino acid sequence including the amino acid sequence set forth as:

```
MAAELAMGAE LPSSPLAIEY VNDFDLMKFE VKKEPPEAER

FCHRLPPGSL SSTPLSTPCS SVPSSPSFCA PSPGTGGGGG

AGGGGGSSQA GGAPGPPSGG PGAVGGTSGK

PALEDLYWMSGYQHHLNPEA LNLTPEDAVE ALIGSGHHGA

HHGAHHPAAA AAYEAFRGPG FAGGGGADDMGAGHHHGAHH

AAHHHHAAHH HHHHHHHHGG AGHGGGAGHH VRLEERFSDD

QLVSMSVRELNRQLRGFSKE EVIRLKQKRR TLKNRGYAQS

CRFKRVQQRH ILESEKCQLQ SQVEQLKLEVGRLAKERDLY

KEKYEKLAGR GGPGSAGGAG FPREPSPPQA GPGGAKGTAD FFL
```

(human MafA, SEQ ID NO: 10, GENBANK® Accession No. NP_963883.2, May 10, 2014, incorporated herein by reference), or

```
MAAELAMGAE LPSSPLAIEY VNDFDLMKFE VKKEPPEAER

FCHRLPPGSL SSTPLSTPCS SVPSSPSFCA PSPGTGGGAG

GGGSAAQAGG APGPPSGGPG TVGGASGKAV

LEDLYWMSGYQHHLNPEALN LTPEDA VEAL IGSGHHGAHH

GAHHPAAAAA YEAFRGQSFA GGGGADDMGAGHHHGAHHTA

HHHHSAHHHH HHHHHHGGSG HHGGGAGHGG GGAGHHVRLE

ERFSDDQLVSMSVRELNRQL RGFSKEEVIR LKQKRRTLKN

RGYAQSCRFK RVQQRHILES EKCQLQSQVEQLKLEVGRLA

KERDLYKEKY EKLAGRGGPG GAGGAGFPRE PSPAQAGPGA

AKGAPDFFL
```

(mouse MafA, SEQ ID NO: 11, GENBANK® Accession No. NP_919331, Apr. 26, 2014, incorporated herein by reference MafA is a beta cell specific and glucose regulated transcription factor for insulin gene expression. The vector, such as an rAAV vector, can encode a MafA protein that has an amino acid sequence at least 95%, 96%, 97%, 98%, 99% or 100% identical to SEQ ID NO: 10 or SEQ ID NO: 11, wherein the protein functions as a transcription factor. The vector can encode a MafA protein that includes at most 10, 9, 8, 7, 6, 5, 4, 3, 2, or 1 conservative amino acid substitutions in SEQ ID NO: 10 or SEQ ID NO: 11, wherein the protein functions as a transcription factor. The vector can be a rAAV8 vector.

In some embodiments, the vectors encode a human Pdx1 amino acid sequence including the amino acid sequence set forth as:

```
MNGEEQYYAA TQLYKDPCAF QRGPAPEFSA SPPACLYMGR

QPPPPPPHPF PGALGALEQGSPPDISPYEV PPLADDPAVA

HLHHHLPAQL ALPHPPAGPF PEGAEPGVLE

EPNRVQLPFPWMKSTKAHAW KGQWAGGAYA AEPEENKRTR

TAYTRAQLLE LEKEFLFNKY ISRPRRVELAVMLNLTERHI

KIWFQNRRMK WKKEEDKKRG GGTAVGGGGV AEPEQDCAVT
```

SGEELLALPPPPPPGGAVPP AAPVAAREGR LPPGLSASPQ

PSSVAPRRPQ EPR (human Pdx 1, SEQ ID NO: 12, GENBANK Accession
No. NP_000200.1, Mar. 15, 2015, incorporated
herein by reference),
or

MNSEEQYYAATQLYKDPCAFQRGPVPEFSANPPACLYMGRQPPPPPPPQ

FTSSLGSLEQGSPPDISPYEVPPLASDDPAGAHLHHHLPAQLGLAHPPP

GPFPNGTEPGGLEEPNRVQLPFPWMKSTKAHAWKGQWAGGAYTAEPEEN

KRTRTAYTRAQLLELEKEFLFNKYISRPRRVELAVMLNLTERHIKIVVF

QNRRMKWKKEEDKKRSSGTPSGGGGGEEPEQDCAVTSGEELLAVPP

LPPPGGAVPPGVPAAVREGLLPSGLSVSPQPSSIAPLRPQEPR (mouse Pdx 1, SEQ ID NO: 13, GENBANK Accession
No: NM_008814.3, Feb. 15, 2015, incorporated
herein by reference).

Pdx1 is a transcriptional activator of several genes, including insulin, somatostatin, glucokinase, islet amyloid polypeptide, and glucose transporter type 2.

The vector, such as an rAAV vector, can encode a Pdx1 protein that has an amino acid sequence at least 95%, 96%, 97%, 98%, 99% or 100% identical to SEQ ID NO: 12 or SEQ ID NO: 13, wherein the protein functions as a transcription factor. The vector can encode a MafA protein that includes at most 10, 9, 8, 7, 6, 5, 4, 3, 2, or 1 conservative amino acid substitutions in SEQ ID NO: 12 or SEQ ID NO: 13, wherein the protein functions as a transcription factor. The vector can be a rAAV2, rAAV6, rAAV8 or rAAV9 vector.

In some embodiments, the nucleic acid sequences encoding MafA and Pdx1 are separated by a connector. In specific non-limiting examples, the connector is 2A. The nucleic acid sequence of the 2A connector is shown below:

(SEQ ID NO: 14)
CGCGCCAAGCGCGGCTCCGGCGCCACCAACTTCTCCCTGCTGAAGCAG

Other exemplary connectors are:

(SEQ ID NO: 15)
CGCGCCAAGCGCGGCTCCGGCCAGTGCACCAACTACGCCCTGCTGAAGCT
GGCCGGCGACGTGGAGTCCAACCCCGGCCCC;
and (SEQ ID NO: 16)
CGCGCCAAGCGCGGCTCCGGCGAGGGCAGAGGAAGTCTTCTAACATGCGG
TGACGTGGAGGAGAATCCCGGCCCT.

Suitable connectors also include a nucleic acid sequence with at most 1, 2, 3, 4, or 5 substitutions in one of SEQ ID NO: 14-16. Suitable connectors are, for example, 40 to 90 nucleotides in length, such as 45 to 85 nucleotides in length, such as 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 nucleotides in length.

The vectors of use in the method disclosed herein encode MafA and Pdx1, but do not encode Ngn3, for example, the Ngn3 protein of GENBANK® Accession No: NM_009719 (mouse), Feb. 15, 2015 and GENBANK® Accession No: NP_033849.3 (Human), Feb. 15, 2015. An exemplary Ngn3 protein is shown below:

(SEQ ID NO: 17)
MAPHPLDALT IQVSPETQQP FPGASDHEVL SSNSTPPSPT

LIPRDCSEAE VGDCRGTSRK LRARRGGRNR PKSELALSKQ

RRSRRKKAND RERNRMHNLN SALDALRGVL

PTFPDDAKLTKIETLRFAHN YIWALTQTLR IADHSFYGPE

PPVPCGELGS PGGGSNGDWG SIYSPVSQAGNLSPTASLEE

FPGLQVPSSP SYLLPGALVF SDFL

Thus, the vector, such as an rAAV vector, does not encode protein that has an amino acid sequence at least 95%, 96%, 97%, 98%, 99% or 100% identical to SEQ ID NO: 17, wherein the protein functions as a transcription factor. The vector doe not encode a protein that includes at most 10, 9, 8, 7, 6, 5, 4, 3, 2, or 1 conservative amino acid substitutions in SEQ ID NO: 17, wherein the protein functions as a transcription factor.

U.S. Published Patent Application No. 2011/0280842, is incorporated by reference herein, which provides Pdx1, MafA and Ngn3 amino acid and nucleic acid sequence. In some embodiments, a rAAV vector includes a nucleic acid encoding Pdx1 and MafA, but does not include a nucleic acid encoding Ngn3.

In some embodiments, a vector of use includes a gene encoding a selectable marker, which includes, but are not limited to, a protein whose expression can be readily detected such as a fluorescent or luminescent protein or an enzyme that acts on a substrate to produce a colored, fluorescent, or luminescent substance ("detectable markers"). There are other genes of use, such as genes that encode drug resistance of provide a function that can be used to purify cells. Selectable markers include neomycin resistance gene (neo), puromycin resistance gene (puro), guanine phosphoribosyl transferase (gpt), dihydrofolate reductase (DHFR), adenosine deaminase (ada), puromycin-N-acetyl-transferase (PAC), hygromycin resistance gene (hyg), multidrug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or *Renilla* luciferase) are also selectable makers.

Pharmaceutical Compositions and Administration to the Pancreatic Duct

Methods are provided for producing pancreatic beta cells in a subject. These method include administering to the subject a vector, such as an adenovirus vector or an AAV vector, encoding heterologous Pdx1 and MafA. The vector does not include a nucleic acid encoding Neurogenin 3 (Ngn3). The subject is not administered any other nucleic acid encoding Ngn3.

For in vivo delivery, a vector, such as an adenovirus or an AAV vector can be formulated into a pharmaceutical composition and will generally be administered locally or systemically. In some embodiments, the vector is administered directly to the pancreas. In other embodiments, intraductally into a pancreatic duct of the subject. In other embodiments, the subject has diabetes, such as type 1 diabetes.

In some embodiments, method are provided for producing pancreatic beta cells from pancreatic alpha cells in a subject. These methods include administering to the subject a vector encoding heterologous Pancreas duodenal homeobox protein (Pdx) 1 and MafA, wherein the vector does not encode Ngn3 and wherein the subject is not administered any other nucleic acid encoding Ngn3, wherein the vector is administered intraductally into a pancreatic duct of the subject.

In additional embodiments, methods are provided for treating diabetes type 1 or pre-diabetes in a subject. The subject can be any mammalian subject, including human and veterinary subjects. The subject can be a child or an adult. The method can include selecting a subject of interest, such as a subject with diabetes. The subject can also be administered insulin. The method can include measuring beta cell number.

In some examples, a subject with diabetes may be clinically diagnosed by a fasting plasma glucose (FPG) concentration of greater than or equal to 7.0 millimole per liter (mmol/L) (126 milligram per deciliter (mg/dL)), or a plasma glucose concentration of greater than or equal to 11.1 mmol/L (200 mg/dL) at about two hours after an oral glucose tolerance test (OGTT) with a 75 gram (g) load, or in a patient with classic symptoms of hyperglycemia or hyperglycemic crisis, a random plasma glucose concentration of greater than or equal to 11.1 mmol/L (200 mg/dL), or HbA1c levels of greater than or equal to 6.5%. In other examples, a subject with pre-diabetes may be diagnosed by impaired glucose tolerance (IGT). An OGTT two-hour plasma glucose of greater than or equal to 140 mg/dL and less than 200 mg/dL (7.8-11.0 mM), or a fasting plasma glucose (FPG) concentration of greater than or equal to 100 mg/dL and less than 125 mg/dL (5.6-6.9 mmol/L), or HbA1c levels of greater than or equal to 5.7% and less than 6.4% (5.7-6.4%) is considered to be IGT, and indicates that a subject has pre-diabetes. Additional information can be found in *Standards of Medical Care in Diabetes*—2010 (American Diabetes Association, *Diabetes Care* 33:S11-61, 2010, incorporated herein by reference).

The disclosed methods produce pancreatic beta cells in a subject. Generally, these cells produce insulin. In some embodiments, the subject is a subject with type 1 diabetes and the pancreatic beta cells produced by the disclosed methods are not recognized by the immune system of the subject. In some embodiments, T cell and/or B cells do not produce an immune response to the pancreatic beta cells produced by the disclosed methods. Thus, in some embodiments, the subject does not mount an autoimmune response to the pancreatic beta cells produced by the disclosed methods. In specific non-limiting examples, the subject does not have immune destruction of the pancreatic beta cells, and does not exhibit a increased lymphocyte invasion of the islets.

Appropriate doses depend on the subject being treated (e.g., human or nonhuman primate or other mammal), age and general condition of the subject to be treated, the severity of the condition being treated, the mode of administration of the AAV vector/virion, among other factors. An appropriate effective amount can be readily determined by one of skill in the art. Thus, a "therapeutically effective amount" will fall in a relatively broad range that can be determined through clinical trials. The method can include measuring an outcome, such as insulin production, improvement in a fasting plasma glucose tolerance test, or pancreatic beta cell number. The method can include administering other therapeutic agents, such as insulin. The method can also include having the subject make lifestyle modifications.

For example, for in vivo injection, i.e., injection directly to the subject, a therapeutically effective dose will be on the order of from about $10^5$ to $10^{16}$ of the AAV virions, such as $10^8$ to $10^{14}$ AAV virions. The dose, of course, depends on the efficiency of transduction, promoter strength, the stability of the message and the protein encoded thereby, and clinical factors. Effective dosages can be readily established by one of ordinary skill in the art through routine trials establishing dose response curves.

Dosage treatment may be a single dose schedule or a multiple dose schedule to ultimately deliver the amount specified above. Moreover, the subject may be administered as many doses as appropriate. Thus, the subject may be given, e.g., $10^5$ to $10^{16}$ AAV virions in a single dose, or two, four, five, six or more doses that collectively result in delivery of, e.g., $10^5$ to $10^{16}$ AAV virions. One of skill in the art can readily determine an appropriate number of doses to administer.

In some embodiments, the AAV is administered at a dose of about $1 \times 10^{11}$ to about $1 \times 10^{14}$ viral particles (vp)/kg. In some examples, the AAV is administered at a dose of about $1 \times 10^{12}$ to about $8 \times 10^{13}$ vp/kg. In other examples, the AAV is administered at a dose of about $1 \times 10^{13}$ to about $6 \times 10^{13}$ vp/kg. In specific non-limiting examples, the AAV is administered at a dose of at least about $1 \times 10^{11}$, at least about $5 \times 10^{11}$, at least about $1 \times 10^{12}$, at least about $5 \times 10^{12}$, at least about $1 \times 10^{13}$, at least about $5 \times 10^{13}$, or at least about $1 \times 10^{14}$ vp/kg. In other non-limiting examples, the rAAV is administered at a dose of no more than about $5 \times 10^{11}$, no more than about $1 \times 10^{12}$, no more than about $5 \times 10^{12}$, no more than about $1 \times 10^{13}$, no more than about $5 \times 10^{13}$, or no more than about $1 \times 10^{14}$ vp/kg. In one non-limiting example, the AAV is administered at a dose of about $1 \times 1012$ vp/kg. The AAV can be administered in a single dose, or in multiple doses (such as 2, 3, 4, 5, 6, 7, 8, 9 or 10 doses) as needed for the desired therapeutic results, such as the production of 0 cells and/or treatment of type 1 diabetes.

Pharmaceutical compositions include sufficient genetic material to produce a therapeutically effective amount of MafA and Pdx1. In some embodiments, AAV virions will be present in the subject compositions in an amount sufficient to provide a therapeutic effect, such as the production of pancreatic beta cells and/or the treatment of diabetes when given in one or more doses.

AAV virions can be provided as lyophilized preparations and diluted in a stabilizing compositions for immediate or future use. Alternatively, the AAV virions can be provided immediately after production and stored for future use.

The pharmaceutical compositions can contain the vector, such as the rAAV vector, and/or virions, and a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

In some embodiments, the excipients confer a protective effect on the AAV virion such that loss of AAV virions, as well as transduceability resulting from formulation procedures, packaging, storage, transport, and the like, is minimized. These excipient compositions are therefore considered "virion-stabilizing" in the sense that they provide higher AAV virion titers and higher transduceability levels than their non-protected counterparts, as measured using standard assays, see, for example, Published U.S. Application No. 2012/0219528, incorporated herein by reference. These Compositions therefore demonstrate "enhanced transduceability levels" as compared to compositions lacking the particular excipients described herein, and are therefore more stable than their non-protected counterparts.

Exemplary excipients that can used to protect the AAV virion from activity degradative conditions include, but are not limited to, detergents, proteins, e.g., ovalbumin and bovine serum albumin, amino acids, e.g., glycine, polyhydric and dihydric alcohols, such as but not limited to polyethylene glycols (PEG) of varying molecular weights, such as PEG-200, PEG-400, PEG-600, PEG-1000, PEG-1450, PEG-3350, PEG-6000, PEG-8000 and any molecular weights in between these values, with molecular weights of 1500 to 6000 preferred, propylene glycols (PG), sugar alcohols, such as a carbohydrate, preferably, sorbitol. The detergent, when present, can be an anionic, a cationic, a zwitterionic or a nonionic detergent. An exemplary detergent is a nonionic detergent. One suitable type of nonionic detergent is a sorbitan ester, e.g., polyoxyethylenesorbitan monolaurate (TWEEN®-20) polyoxyethylenesorbitan monopalmitate (TWEEN®-40), polyoxyethylenesorbitan monostearate (TWEEN®-60), polyoxyethylenesorbitan tristearate (TWEEN®-65), polyoxyethylenesorbitan monooleate (TWEEN®-80), polyoxyethylenesorbitan trioleate (TWEEN®-85), such as TWEEN®-20 and/or TWEEN®-80. These excipients are commercially available from a number of vendors, such as Sigma, St. Louis, Mo.

The amount of the various excipients present in any of the disclosed compositions varies and is readily determined by one of skill in the art. For example, a protein excipient, such as BSA, if present, will can be present at a concentration of between 1.0 weight (wt.) % to about 20 wt. %, preferably 10 wt. %. If an amino acid such as glycine is used in the formulations, it can be present at a concentration of about 1 wt. % to about 5 wt. %. A carbohydrate, such as sorbitol, if present, can be present at a concentration of about 0.1 wt % to about 10 wt. %, such as between about 0.5 wt. % to about 15 wt. %, or about 1 wt. % to about 5 wt. %. If polyethylene glycol is present, it can generally be present on the order of about 2 wt. % to about 40 wt. %, such as about 10 wt. % top about 25 wt. %. If propylene glycol is used in the subject formulations, it will typically be present at a concentration of about 2 wt. % to about 60 wt. %, such as about 5 wt. % to about 30 wt. %. If a detergent such as a sorbitan ester (TWEEN®) is present, it can be present at a concentration of about 0.05 wt. % to about 5 wt. %, such as between about 0.1 wt. % and about 1 wt %, see U.S. Published Patent Application No. 2012/0219528, which is incorporated herein by reference. In one example, an aqueous virion-stabilizing formulation comprises a carbohydrate, such as sorbitol, at a concentration of between 0.1 wt. % to about 10 wt. %, such as between about 1 wt. % to about 5 wt. %, and a detergent, such as a sorbitan ester (TWEEN®) at a concentration of between about 0.05 wt. % and about 5 wt. %, such as between about 0.1 wt. % and about 1 wt. %. Virions are generally present in the composition in an amount sufficient to provide a therapeutic effect when given in one or more doses, as defined above.

The pharmaceutical compositions can include a contrast dye is administered in addition to the viral vector, such an adenoviral vector, encoding Pdx1 and MafA. The contrast dye can be a low-osmolar low-viscosity non-ionic dye, a low-viscosity high-osmolar dye, or a dissociable high-viscosity dye. In specific non-limiting examples the dye is Iopromid, Ioglicinate, or Ioxaglinate. Thus, provided herein is a pharmaceutical composition including a) an adeno-associated virus vector, such as rAAV8, comprising a promoter operably linked to a nucleic acids encoding Pdx1 and a nucleic acid encoding MafA, wherein the vector does not encode Ngn3; b) a buffer; and c) a contrast dye for endoscopic retrograde cholangiopancreatography. The pharmaceutical composition does not include a nucleic acid encoding Ngn3. Any of the AAV vectors disclosed herein can be included in this composition. The AAV vector can be encapsulated in a virion. The composition can be formulated for administration to the pancreatic duct.

The disclosed pharmaceutical compositions including a viral vector, such an adenoviral vector, encoding Pdx1 and MafA, or a virion, can be delivered to humans or other animals by any means, including orally, intravenously, intramuscularly, intraperitoneally, intranasally, intradermally, intrathecally, subcutaneously, via inhalation or via suppository. In one non-limiting example, the composition is administered into the pancreatic duct of a subject in vivo.

One exemplary method for intraductal administration is Endoscopic Retrograde Cholangiopancreatography (ERCP). ERCP is an endoscopic technique that involves the placement of a side-viewing instrument (generally either an endoscope or duodenoscope) within the descending duodenum. The procedure eliminates the need for invasive surgical procedures for administration to the pancreatic duct.

In an ERCP procedure, the patient will generally lie on their side on an examining table. The patient will then be given medication to help numb the back of the patient's throat, and a sedative to help the patient relax during the examination. The patient then swallows the endoscope. The thin, flexible endoscope is passed carefully through the alimentary canal of the patient. The physician guides the endoscope through the patient's esophagus, stomach, and the first part of the small intestine known as the duodenum. Because of the endoscope's relatively small diameter, most patients can tolerate the unusualness of having the endoscope advanced through the opening of their mouth.

The physician stops the advancement of the endoscope when the endoscope reaches the junction where the ducts of the biliary tree and pancreas open into the duodenum. This location is called the papilla of Vater, or also commonly referred to as the ampulla of Vater. The papilla of Vater is a small mound of tissue looking and acting similarly to a nipple. The papilla of Vater emits a substance known as bile into the small intestine, as well as pancreatic secretions that contain digestive enzymes. Bile is a combination of chemicals made in the liver and is necessary in the act of digestion. Bile is stored and concentrated in the gallbladder between meals. When digestive indicators stimulate the gallbladder, however, the gallbladder squeezes the bile through the common bile duct and subsequently through the papilla of Vater. The pancreas secretes enzymes in response to a meal, and the enzymes help digest carbohydrates, fats, and proteins.

The patient will be instructed (or manually maneuvered) to lie flat on their stomach once the endoscope reaches the papilla of Vater. For visualization or treatment within the biliary tree, the distal end of the endoscope is positioned proximate the papilla of Vater. A catheter is then advanced through the endoscope until the distal tip of the catheter emerges from the opening at the endoscope's distal end. The distal end of the catheter is guided through the endoscope's orifice to the papilla of Vater (located between the sphincter of Oddi) leading to the common bile duct and the pancreatic duct. In the case of pancreas-specific delivery of reagents, the pancreatic duct proper can be entered.

ERCP catheters can be constructed from Teflon, polyurethane and polyaminde. ERCP catheters also can also be constructed from resin comprised of nylon and PEBA (see U.S. Pat. No. 5,843,028), and can be construed for use by a single operator (see U.S. Pat. No. 7,179,252). At times, a spring wire guide may be placed in the lumen of the catheter to assist in cannulation of the ducts. A stylet, used to stiffen the catheter, must first be removed prior to spring wire guide insertion.

A dual or multi-lumen ERCP catheter in which one lumen could be utilized to accommodate the spring wire guide or diagnostic or therapeutic device, and in which a second lumen could be utilized for contrast media and/or dye infusion and or for administration of a pharmaceutical composition including a viral vector, such an adenoviral vector, encoding Pdx1 and MafA. In some embodiments, a contrast dye is administered in addition to the pharmaceutical composition including a viral vector, such an adenoviral vector, encoding Pdx1 and MafA. The contrast dye can be a low-osmolar low-viscosity non-ionic dye, a low-viscosity high-osmolar dye, or a dissociable high-viscosity dye. In specific non-limiting examples the dye is Iopromid, Ioglicinate, or Ioxaglinate. Endoscopes have been designed for the delivery of more than one liquid solution, such as a first liquid composition including a viral vector, such an adenoviral vector, encoding Pdx1 and MafA, and a second liquid composition including dye, see U.S. Pat. No. 7,597,662, which is incorporated herein by reference. Thus, the pharmaceutical composition including a viral vector, such an adenoviral vector, encoding Pdx1 and MafA and the dye can be delivered in the same or separate liquid compositions. Methods and devices for using biliary catheters for accessing the biliary tree for ERCP procedures are disclosed in U.S. Pat. No. 5,843,028, U.S. Pat. No. 5,397,302 U.S. Pat. No. 5,320,602, which are incorporated by reference herein.

In additional examples, the vector is administered using a viral infusion technique into a pancreatic duct. Suitable methods are disclosed, for example, in Guo et al. Laboratory Invest. 93: 1241-1253, 2013, incorporated by reference herein.

EXAMPLES

Insulin is a key regulator of glucose homeostasis, and is produced by pancreatic beta cells. Insufficient insulin leads to diabetes mellitus, a metabolic disease that affects at least 200 million people worldwide (Pipeleers, D. et al. *Ann N Y Acad Sci* 958, 69-76 (2002); Zaret, K. S. & Grompe, M. *Science* 322, 1490-1494, doi:10.1126/science.1161431 (2008); Weir, G. C. & Bonner-Weir, S. *J Am Optom Assoc* 69, 727-732 (1998); Ackermann, A. M. & Gannon, M. *J Mol Endocrinol* 38, 193 206, doi:38/2/193 [pii]10.1677/JME-06-0053 (2007); Pipeleers, D. et al. *Diabetes Obes Metab* 10 Suppl 4, 54-62, doi: 10.1111/j 0.1463-1326.2008.00941.x (2008); Pipeleers, D. & Ling, Z. *Diabetes Metab Rev* 8, 209-227 (1992)). The fundamental objective of diabetes treatment is to preserve and restore a functional beta cell mass, perhaps through beta-cell replacement therapy. However, beta-cell replacement may fall short in type I diabetes (T1D) due to persistent autoimmunity against the new beta-cells (with preexisting primed immune cells ready to attack any newly delivered beta-cells) (Pipeleers, D. et al. *Ann N Acad Sci* 958, 69-76 (2002); Zaret, K. S. & Grompe, M. *Science* 322, 1490-1494, doi:10.1126/science.1161431 (2008); Weir, G. C. & Bonner-Weir, S. *J Am Optom Assoc* 69, 727-732 (1998); Ackermann, A. M. & Gannon, M. *J Mol Endocrinol* 38, 193-206, doi:38/2/193 10.1677/JME-06-0053 (2007); Pipeleers, D. et al. *Diabetes Obes Metab* 10 Suppl 4, 54-62, doi:10.1111/j.1463-1326.2008.00941.x (2008)). In fact, this form of renewed autoimmune attack has been found to be particularly aggressive (Purcell, L. J. & Mottram, P. L. *Transplant Proc* 27, 2166-2167 (1995)). Unfortunately, a clinically applicable strategy leading to an increase in beta-cell mass without the need for immunosuppression has yet to be developed for T1D. Such a clinical strategy would be hugely advantageous. T1D could be cured, without the need for immunosuppression. In addition, it would avoid the need for allogeneic islet transplants, which can exacerbate an immune attack against future transplants of any kind, especially kidney (Campbell, P. M. et al. *Am J Transplant* 7, 1242-1248, doi:10.1111/j.1600-6143.2007.01777.x (2007)).

Although great efforts have been made to identify, isolate and purify beta cell progenitors in the adult pancreas (Kushner, J. A., Weir, G. C. & Bonner-Weir, S. *Cell Metab* 11, 2-3, doi:S1550-4131(09)00379-9 [pii] 10.1016/j.cmet.2009.12.005 (2010); Kopp, J. L. et al. *Cell Cycle* 10, 1921-1927 (2011)), accumulating evidence does not support a substantial contribution of beta-cell neogenesis to a functional beta-cell mass in the adult pancreas (Dor, Y., Brown, J., Martinez, O. I. & Melton, D. A. *Nature* 429, 41-46, (2004); Teta, M., Rankin, M. M., Long, S. Y., Stein, G. M. & Kushner, J. A. *Dev Cell* 12, 817-826, (2007); Meier, J. J. et al. *Diabetes* 57, 1584-1594, (2008); Georgia, S. & Bhushan, A. *J Clin Invest* 114, 963-968, doi:10.1172/JCI22098 (2004); Xiao, X. et al. *J Biol Chem* 288, 25297-25308, (2013); Xiao, X. et al. *J Clin Invest* 123, 2207-2217, (2013); Xiao, X. et al. *Diabetes* 62, 1217-1226, (2013); Rankin, M. M. et al. *Diabetes* 62, 16341645, (2013); Solar, M. et al. *Dev Cell* 17, 849-860, (2009); Kopp, J. L. et al. *Development* 138, 653-665, (2011); Chintinne, M. et al. *PLoS One* 7, e43959, (2012); Kopinke, D. et al. *Development* 138, 431-441, (2011); Desai, B. M. et al. *J Clin Invest* 117, 971-977; Pan, F. C. et al. *Development* 140, 751-764, (2013); Cavelti-Weder, C. et al. *Endocrinology* 154, 4493-4502, (2013); Tonne, J. M. et al. *Diabetologia*, doi:10.1007/s00125-014-3416-4 (2014)), except for a few rare situations (Thorel, F. et al. *Nature* 464, 1149-1154, (2010); Baeyens, L. et al. *Nat Biotechnol* 32, 76-83, (2014); Chera, S. et al. *Nature* 514, 503-507, (2014)). Thus, gene manipulation may be required for generating new beta-cells from other cell Types (Zhou, Q., Brown, J., Kanarek, A., Rajagopal, J. & Melton, D. A. *Nature* 455, 627-632, (2008); Lee, J. et al. *eLife* 2, e00940, doi:10.7554/eLife.00940 (2013); Li, W. et al. *Nat Biotechnol* 32, 1223-1230, (2014)). Ectopic expression of a combination of three key pancreatic beta-cell transcription factors [Pdx1, Neurogenin 3 (Ngn3) and MafA] has been shown to reprogram adult mouse pancreatic acinar cells into beta-cell-like cells (Zhou, Q., Brown, J., Kanarek, A., Rajagopal, J. & Melton, D. A. *Nature* 455, 627-632, (2008); Lee, J. et al. *eLife* 2, e00940, doi:10.7554/eLife.00940 (2013); Akinci, E., et al., *Biochem J* 442, 539-550, (2012)). Moreover, co-overexpression of these three genes has been shown to convert Sox9$^+$ liver cells into insulin-producing cells (Banga, A. et al., *Proc Natl Acad Sci USA* 109, 15336-15341, (2012)). As disclosed herein, it is the alpha cells that are the ideal source for beta-cell replacement. It was examined if forced expression of key beta-cell transcription factors in alpha cells triggers their reprogramming to generate beta or beta-like cells. Non-integrative adeno-associated viral (AAV) vectors can impart long-term expression of transgenes up to 4.5 kb in length. Moreover, AAV vectors have been found to be more efficient than adenoviral and lentiviral vectors in transducing pancreatic cells (Jimenez, V. et al. Diabetologia 54, 1075-1086, (2011); Guo, P. et al. Journal of virological methods 183, 139-146 (2012); Guo, P. et al. Bioengineered 4 (2012)). Among AAV vectors, serotype 8 has been shown to have the highest transduction efficiency for islet endocrine cells (Tonne, J. M. et al. Diabetologia, (2014); Jimenez, V. et al. Diabetologia 54, 1075-1086, (2011); Guo, P. et al. Bioengineered 4 (2012)). It is disclosed herein that two beta-cell-specific transcription factors, Pdx1 and MafA, were expressed in an immortalized mouse alpha cell line alpha-TC1 (aTC) using an AAV vector. This expression resulted in expression of insulin and suppression of glucagon. Next, using a transgenic mouse model that allows lineage tracing of alpha cells, Pdx1 and MafA expressing viruses were delivered through pancreatic intraductal infusion system to the mouse pancreas (Xiao, X. et al. J Biol Chem 288, 25297-25308, (2013); Xiao, X. et al. Diabetologia 57, 991-1000, (2014); Xiao, X. et al. Proc Natl Acad Sci USA 111, E1211-1220, (2014); Xiao, X. et al. Nat Protoc 9, 2719-2724, (2014)). Glucose normalization was observed in beta-cell-toxin-treated mice, and the new beta cells were found to derive almost exclusively from alpha cells. Virus was similarly delivered to autoimmune, actively diabetic non-obese diabetes (NOD) mice, and durable euglycemia was observed for as long as 4 months. Diabetogenic T-cells responded to these alpha-cell-derived beta-cells in vitro, but adoptive transfers and islet transplants suggested that the NOD autoimmune cells had returned to a naive state in which they are not being exposed to beta-cell autoantigens. Thus, the islet niche may be important for protecting any replacement beta-cells in T1D. In addition, the use of a truncated glucagon promoter resulted in increased efficacy.

Example 1

Materials and Methods

Virus Production:

AAV serotype 8 vectors were generated by transfection of human embryonic kidney 293 cells as described before (Guo, P. et al. Journal of virological methods 183, 139-146, (2012); Guo, P. et al. Bioengineered 4 (2013) 4(2):103-6. Mouse gene open reading frames for Pdx1 and MafA were amplified from embryonic pancreatic cDNA. GFP was amplified from pLVX-IRES-ZsGreen (Clontech, USA). The small 2A peptide that connects Pdx1 and MafA in the AAV-PM construct allows efficient, stoichiometric production of discrete protein products within a single vector through a "cleavage" event within the 2A peptide sequence (Guo, P. et al. Bioengineered 4 (2012)). Transfection was performed with Lipofectamine 2000 reagent (Invitrogen, USA), according to the instructions of the manufacturer. Purified AAV vectors were filtered and stored at −80° C. Titration of viral vectors was determined by Viral p24 ELISA kit (Clontech).

Cell Culture and In Vitro Transduction with AAV:

Mouse aTC cells (ATCC, USA) were grown in low-glucose DMEM supplemented with 10% FBS. For transduction of aTC cells in vitro, the cells were incubated with the AAV in serum-deprived culture media at a multiplicity of infection (MOI) of 100 for 24 hours before the serum was added (Guo, P. et al. Bioengineered 4 (2013) 4(2):103-6. The cells were then harvested for analysis 2 weeks after infection.

Mouse Manipulation:

All mouse experiments were approved. Female C57BL/6, NOD, NOD/SCID and R26R$^{Tomato}$ (C56BL/6 background) mice were all purchased from the Jackson Lab (USA). Glucagon promoter Cre (GCG-Cre; C56BL/6 background) mice were purchased from MMRRC (USA). GCG-Cre; R26R$^{Tomato}$ mice were generated by crossing male GCG-Cre with female R26R$^{Tomato}$ mice and eight-week-old females heterozygous for both Cre and Tomato were used for the experiments. Female C57BL/6 and NOD/SCID mice were used at 10 weeks of age. Female NOD mice were used when the blood glucose reached a specified level. Measurements of mouse blood sugar were performed at 10 am after a two-hour fasting period. Intraperitoneal glucose tolerance test (IPGTT) was performed as previously described (Xiao, X. et al. Diabetes 62, 1217-1226 (2013); Xiao, X. et al. Diabetologia 57, 991-1000, (2014)).

The beta-cell toxin ALX was injected via the dorsal tail vein at 65 mg/kg body weight, while STZ was injected intraperitoneally at 150 mg/kg body weight, as described before (Xiao, X. et al. J Clin Invest 123, 2207-2217, (2013)). For destroying beta cells in human islets, STZ (20 mmol/l) was given to cultured human islets for 24 hours before further treatment.

Pancreatic intraductal viral infusion was performed as described previously (Xiao, X. et al. Nat Protoc 9, 2719-2724, (2014)). For infection of alpha cells, 1500 viruses were infused at a rate of 5 μl/min. For labeling proliferating cells, BrdU drinking water was given immediately after viral infusion and renewed weekly until the end of the experiment as described before (Xiao, X. et al. Diabetes 62, 1217-1226, (2013); Xiao, X. et al. Proc Natl Acad Sci USA 111, E1211-1220, (2014)). Islet transplantation was performed as described before (Xiao, X. et al. Diabetologia 57, 991-1000, (2014)).

RNA Isolation and Quantitative Polymerase Chain Reaction (RT-qPCR):

RNA extraction and cDNA synthesis have been described before (Xiao, X. et al. J Biol Chem 288, 25297-25308, (2013); Xiao, X. et al. J Clin Invest 123, 2207-2217, (2013); Xiao, X. et al. Diabetologia 57, 991-1000, (2014); Xiao, X. et al. Proc Natl Acad Sci USA 111, E1211-1220, (2014)). RT-qPCR primers were all purchased from Qiagen. They are CycloA (QT00247709), Pdx1 (QT00102235), Ngn3 (QT00262850), MafA (QT01037638), Pax4 (QT01052772), Nkx6.1 (QT00143318), NeuroD1 (QT00156982), Glut2 (QT00103537), Insulin (QT00114289) and Glucagon (QT00124033). RT-qPCR was performed as described before (Xiao, X. et al. J Biol Chem 288, 25297-25308, (2013); Xiao, X. et al. J Clin Invest 123, 2207-2217, (2013); Xiao, X. et al. Diabetologia 57, 991-1000, (2014); Xiao, X. et al. Proc Natl Acad Sci USA 111, E1211-1220, (2014)). Values were normalized against CycloA, which proved to be stable across the samples, and then compared to controls.

Immunocytochemistry and Immunohistochemistry:

Cells cultured in staining-plates were fixed for 2 hours in 4% formalin before immunocytochemical staining. All the mice received heart perfusion to remove red blood cells from the vessels before the pancreas was harvested, as described before (Xiao, X. et al. Diabetes 62, 1217-1226, (2013)). Pancreas samples were then fixed in zinc (BD Biosciences) for 6 hours before an additional 2 hours' fixation in 4% formalin, then cryo-protected in 30% sucrose overnight, followed by freezing in a longitudinal orientation (from tail to head of the pancreas) and sectioned at 6 μm. Tomato and GFP were detected by direct fluorescence. Primary antibodies for immunostaining are: guinea pig polyclonal insulin-specific (Dako, USA), mouse monoclonal glucagon-specific (Sigma, USA), rabbit polyclonal Pax4-specific (Santa CruZ, USA), rat polyclonal BrdU-specific and CD45-specific (Abcam, USA), rabbit polyclonal glucagon-specific (Cell signaling, USA). No antigen retrieval was necessary, except for BrdU, which was performed as described before (Xiao, X. et al. *Diabetes* 62, 1217-1226, (2013). Secondary antibodies for indirect fluorescent staining were Cy2, Cy3, or Cy5 conjugated streptavidin-, rabbit-, rat-, goat-, mouse- and guinea pig-specific (Jackson ImmunoResearch Labs, USA). Nuclear staining was performed with Hoechst solution (HO, BD Bioscience, USA). Confocal images were acquired as previously described (Xiao, X. et al. *J Biol Chem* 288, 25297-25308, (2013); Xiao, X. et al. *J Clin Invest* 123, 2207-2217, (2013)).

Adoptive Transfer of Splenocytes into NOD/SCID Mice:

Isolation of splenocytes and adoptive transfer of splenocytes into NOD/SCID mice were performed as described before (Delmastro, M. M. et al. *Diabetes* 61, 1760-1768, (2012)).

In Vitro BDC2.5 T Cell Assay:

BDC2.5 T cell clones ($2\times10^4$), NOD.scid splenocytes as antigen-presenting cells ($4\times10^5$), and $5\times10^3$ islet cells from control or neogenic mice were combined in 200 µl supplemented DMEM in triplicate in 96-well tissue culture plates and incubated at 37° C. for 72 hours. The antigenicity of the islet cells from both groups was determined by measuring IFN-γ secretion from culture supernatants by enzyme-linked immunosorbent assay (ELISA). Absorbances were measured at 450 nm with a SpectraMax M2 microplate reader (Molecular Devices). Data were analyzed with SoftMax Pro (Molecular Devices).

Human Islets:

Human islets were isolated from previously healthy, non-diabetic organ donors. Five independent human islet batches from three male donors and two female donors aged ranging from 32 to 55 were used in this study. Each experiment used islets from the same batch to compare different groups. The final data are from a summary of 5 experiments using these 5 batches accordingly.

Quantifications and Statistics:

For in vitro experiments, each condition contains five repeats. For in vivo experiments, five mice were used for each group. Alpha cell mass, beta cell mass, percentage of proliferating beta cells were quantified as described before (Xiao, X. et al. *Proc Natl Acad Sci USA* 111, E1211-1220 (2014)). All data were statistically analyzed by one-way ANOVA with a Bonferoni correction. Significance was presented as * when p<0.05, and s** when p<0.01. No significance was presented as NS.

Example 2

Overexpression of Pdx1 and MafA Significantly Increased Insulin Production in aTC Cells To induce alpha-to-beta cell conversion, a mouse alpha cell line, aTC, was used in a proof-of-principle overexpression experiment to screen for the optimal transcription factors for inducing such a conversion. Specifically, it was found that overexpression of a combination of Pdx1 and MafA (PM) using AAV (AAV-PM) in aTC cells increased insulin transcripts by nearly 8 fold, compared to aTC cells transduced by control AAV-GFP virus, and decreased glucagon transcripts by more than 5-fold, which was further confirmed by immunocytochemistry (FIG. 6). Thus, a possible alpha-to-beta cell conversion was investigated in vivo with this viral gene delivery approach.

Example 3

Intraductal Infusion of PM Virus Reversed Toxin-Induced Diabetes in Mice

Figure 7A:
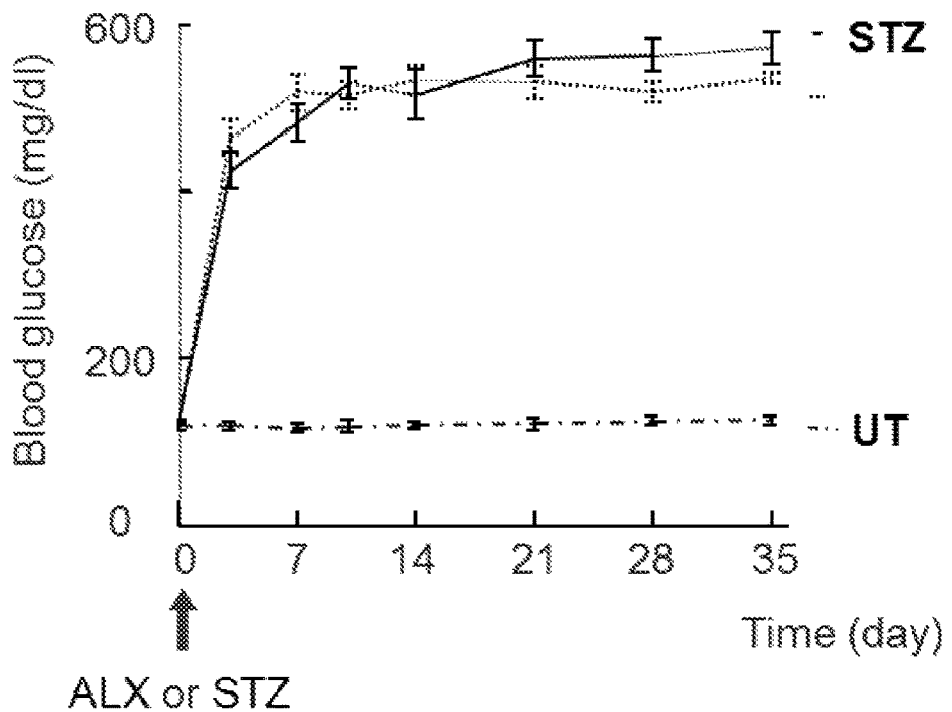
FIGS. 7A-7E: Islet effects of toxin-induced massive beta-cell loss. ALX or STZ was given to C57BL/6 mice. (A) Sustained fasting hyperglycemia was induced in mice within 3 days after injection of either type of toxin. (B) A significant decrease (>90%) in beta-cell mass and a modest but significant increase in alpha-cell mass were detected in mice one week after toxin injection. (C-E) Representative images for islets in untreated (UT) mice (C), in mice one week after ALX treatment (D), and in mice one week after STZ treatment (E). INS: insulin; GCG: glucagon; HO: Hoechst, nuclear stain. *: $p<0.05$. **: $p<0.01$ (compared to control UT). Scale bars are 20 μM.
Figure 7B:
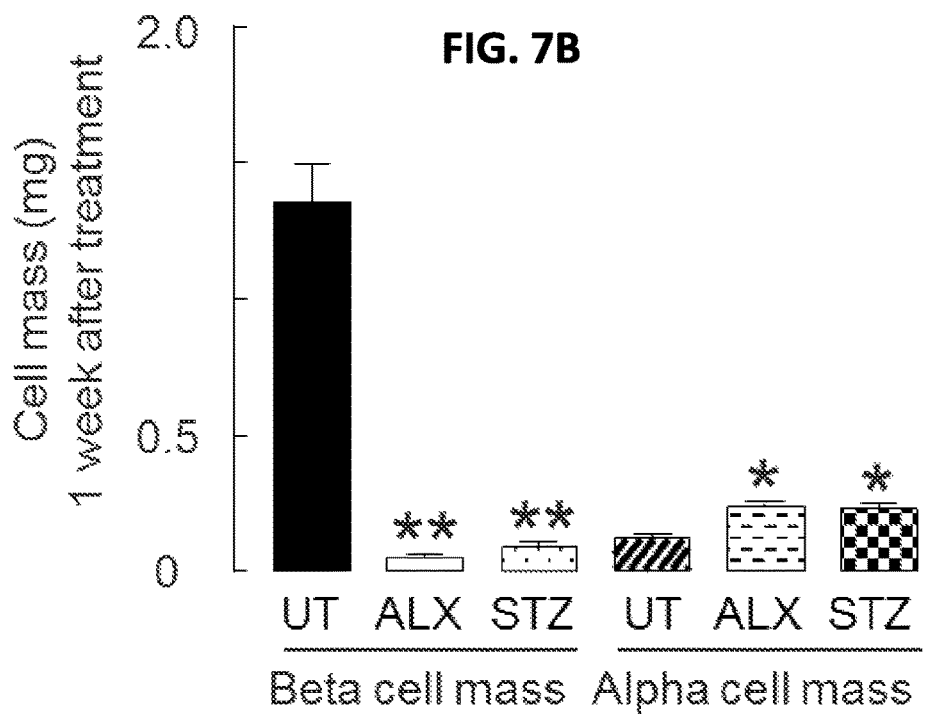
Figure 7E:
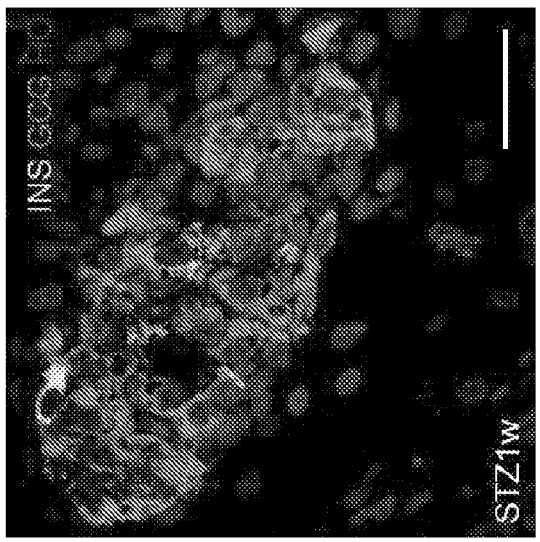
Figure 7D:
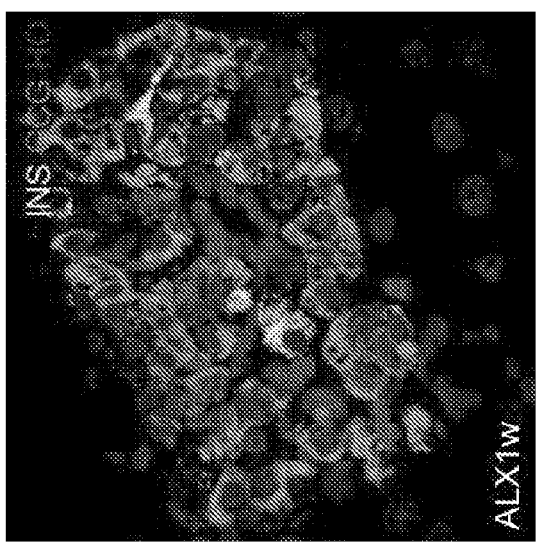
Figure 7C:
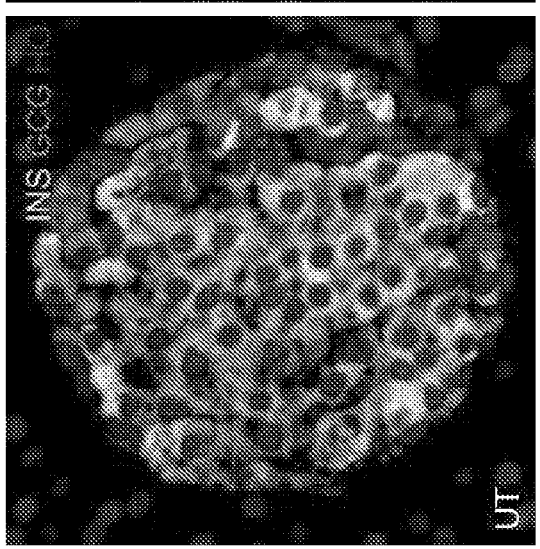

It was examined whether overexpression of AAV-PM could trigger alpha-to-beta cell conversion in vivo to generate functional beta cells. Administration of a single dose of either alloxan (ALX) or streptotozocin (STZ) induced sustained hyperglycemia in C57BL/6 mice (FIG. 7A) (Xiao, X. et al. *J Clin Invest* 123, 2207-2217, (2013)) due to a Significant decrease in beta-cell mass (FIG. 7B-E, ALX: decreased to 3.8±0.2%, STZ: decreased to 6.5±0.9%). Moreover, both ALX and STZ induced a modest but significant increase in alpha-cell mass (FIG. 7B-E), similar to that seen in some diabetic patients (Zaret, K. S. & White, M. F. *Nature* 464, 1132-1133, (2010)). ALX was used in further studies to examine alpha-to-beta cell conversion in vivo, due to the higher and more consistent degree of beta-cell ablation at the dosages used. To allow lineage tracing of alpha cells, GCG-Cre; R26R$^{Tomato}$ reporter mice (Xiao, X. et al. *J Biol Chem* 288, 25297-25308, (2013); Herrera, P. L. *Development* 127, 2317-2322 (2000); Xiao, X. et al. *J Biol Chem* 288, 8636-8646, (2013)) were generated, in which tomato red fluorescence specifically labels the GCG$^+$ alpha cell lineage in the pancreas (FIG. 1A). Quantification showed that the baseline labeling of alpha cells in GCG-Cre; R26R$^{Tomato}$ mice was 71.5±5.5%, with complete absence of off-target labeling (FIG. 1B). To deliver virus to the pancreas, a recently developed pancreatic intraductal viral infusion technique was used in which infusion of 150 µl of AAV serotype 8 efficiently transduced endocrine cells (Xiao, X. et al. *J Biol Chem* 288, 25297-25308, (2013); Xiao, X. et al. *Diabetologia* 57, 991-1000, (2014); Xiao, X. et al. *Proc Natl Acad Sci USA* 111, E1211-1220, (2014); Xiao, X. et al. *Nat Protoc* 9, 2719-2724, (2014)).

Figure 1E:
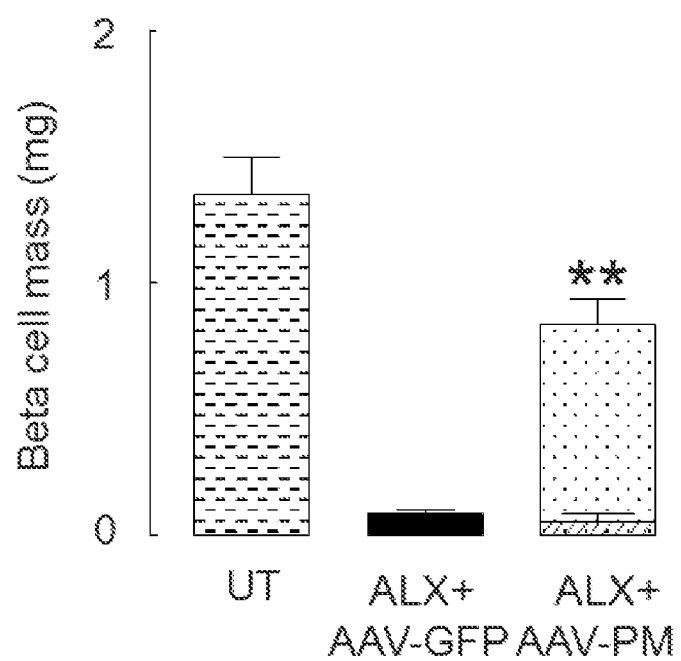

Thus, ALX was given to destroy the majority of beta cells in these GCG-Cre; R26R$^{Tomato}$ mice. One week later, an intraductal infusion with AAV-PM or control AAV-GFP was performed. It was found that ALX-induced hyperglycemia was corrected within 2 weeks by intraductal infusion with AAV-PM, but not by control AAV-GFP (FIG. 1C). A significant improvement in the glucose response (intraperitoneal glucose tolerance test, IPGTT) was also seen in ALX-treated, AAV-PM-infused mice at 4 weeks after viral infusion (FIG. 1D). Moreover, beta cell mass significantly increased in ALX-mice receiving AAV-PM (0.84±0.06 mg), compared to mice receiving AAV-GFP (0.09±0.01 mg) at 4 weeks after viral infusion, reaching more than 60% of the beta cell mass in untreated mice (UT, no ALX, no virus; 1.35±0.11 mg) (FIG. 1E). Thus, intraductal infusion of AAV-PM reversed ALX-induced diabetes in mice.

Example 4

Regenerated Beta Cells are Mainly Derived from Reprogrammed Alpha Cells

Figure 2A:
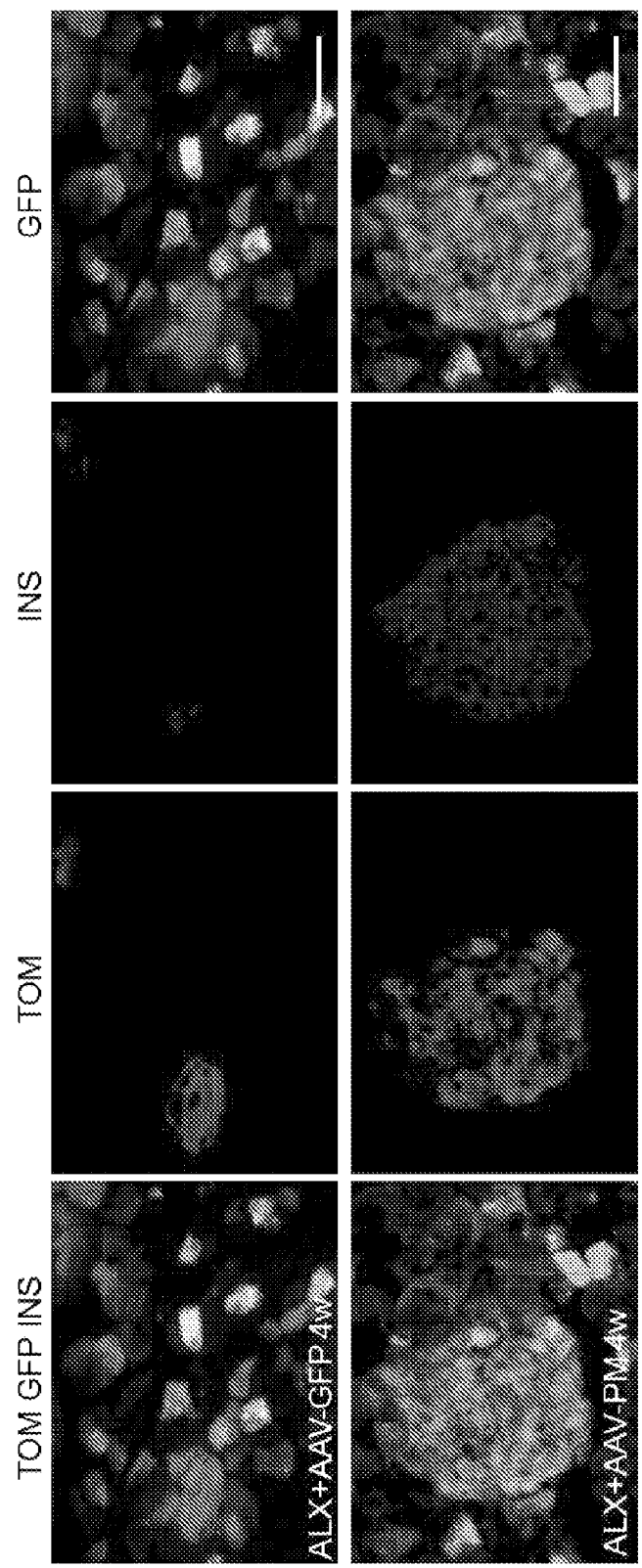
FIGS. 2A-2B: Neogenic beta cells derived from reprogrammed alpha cells. (A) Immunostaining for insulin (INS) after infusion of control AAV-GFP (upper panels) or AAV-PM (lower panels), along with direct fluorescence for tomato (TOM, from GCG-Cre activity) and for green fluorescence (GFP, from viral infection). Both AAV-GFP and AAV-PM viruses carry a GFP cassette. (B) Bromodeoxyuridine (BrdU) was continuously provided in the drinking water during the 4 weeks after viral infusion. Quantification showed that 78.5±6.6% of TOM+INS+cells had incorporated BrdU, suggesting that these cells mainly originated from converted alpha cells, with significant proliferation. Scale bars are 20 μM.
Figure 2B:
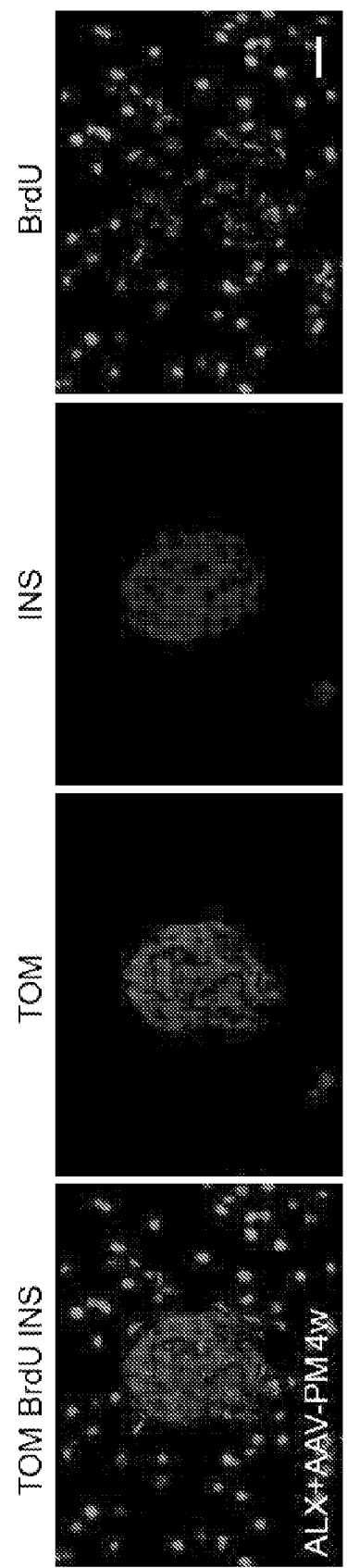
Figure 8A:
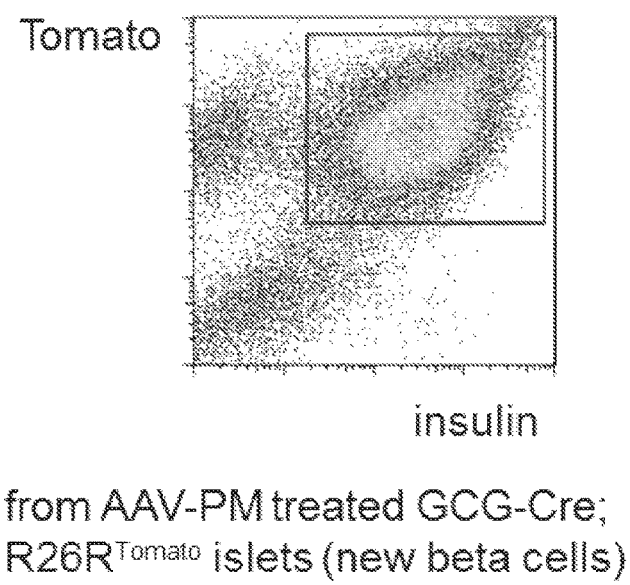
FIGS. 8A-8C: Reprogrammed alpha cells are transcriptionally similar, but not identical to normal beta cells. (A-C) New beta cells were isolated 1 month after AAV-PM infusion from ALX-treated GCG-Cre; R26R$^{Tomato}$ mice, based on expression of tomato red (alpha-cell lineage) and insulin staining by flow cytometry (A). Gene profiling of these new beta cells was performed by reverse transcriptase quantitative polymerase chain reaction (RT-qPCR), and compared to purified normal beta cells (from MIP-GFP mice), and to undisturbed alpha cells (from Tomato-positive cells in GCG-Cre; R26R$^{Tomato}$ mice without any treatment). (B) RT-qPCR for insulin and glucagon gene transcripts. (C) RT-qPCR for Pdx1, MafA, Nkx6.1, NeuroD1 and Glut2 gene transcripts. *: $p<0.05$. **: $p<0.01$ (compared to controls). NS: non-significant.
Figure 8B:
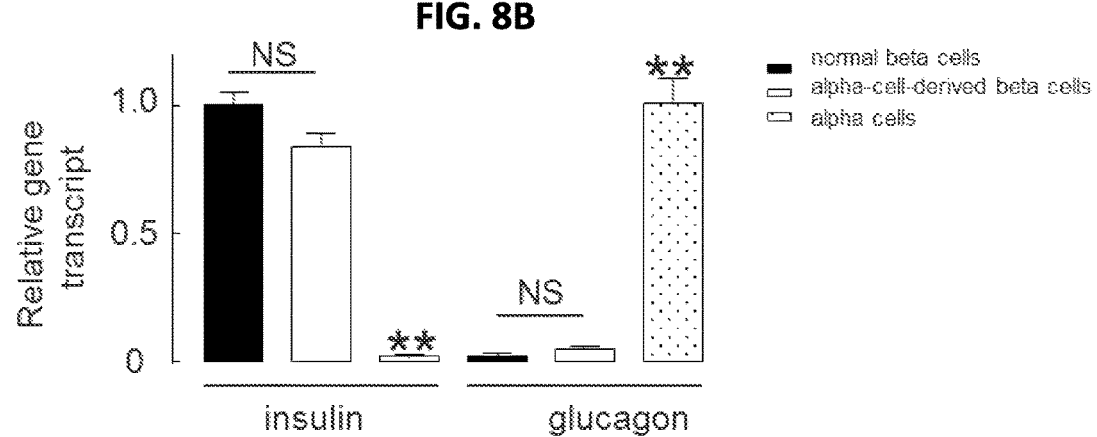
Figure 8C:
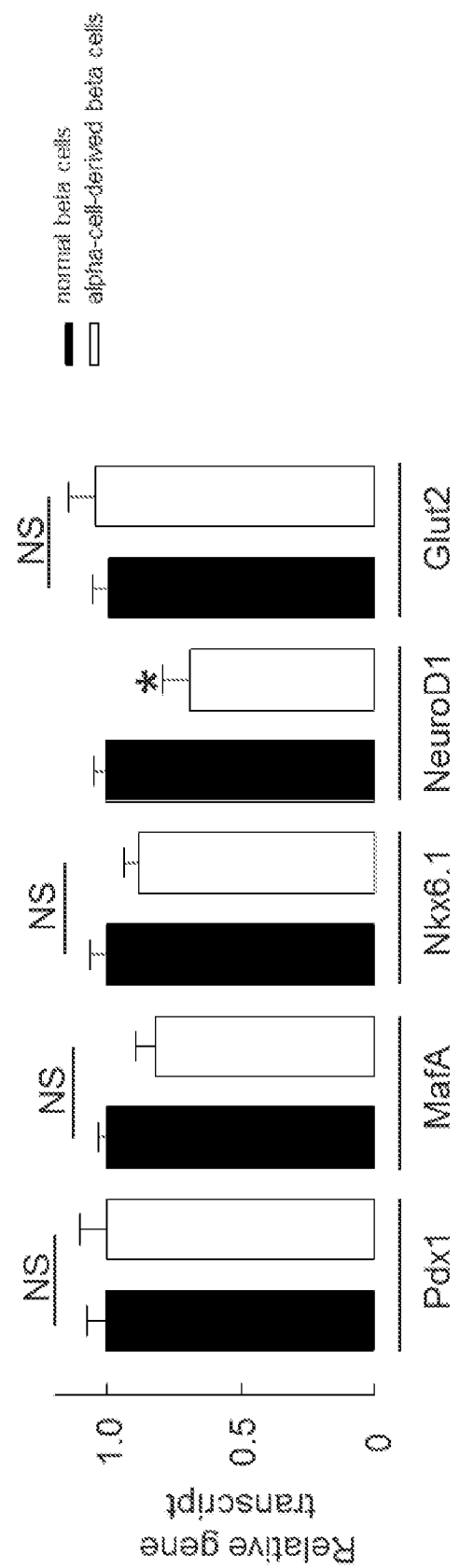

In the GCG-Cre; R26R$^{Tomato}$ mice, it was found that about 80% of the beta cells after AAV-PM infusion in ALX-treated mice were labeled with tomato (FIG. 2A), suggesting an alpha-cell origin. FAC sorted tomato-positive beta cells appeared to be transcriptionally similar, but not identical to mature beta cells sorted from MIP-GFP mice (FIG. 8). Very few beta cells were not tagged with tomato red (FIG. 1B, E), presumably representing those beta cells that either derived from the few surviving beta cells after ALX treatment, or else derived mainly from unlabeled reprogrammed alpha cells. In pancreases with infusion of control AAV-GFP, no INS+ cells were found to be labeled with tomato (FIG. 2A). The mice were given continuous BrdU in the drinking water starting immediately after the viral infusion for 4 weeks. It was found that 78.5±6.6% of the tomato+ INS+ cells had incorporated BrdU, suggesting that a significant proliferation had occurred in the neogenic beta cells reprogrammed from alpha cells (FIG. 2B).

Example 5

Figure 3B:
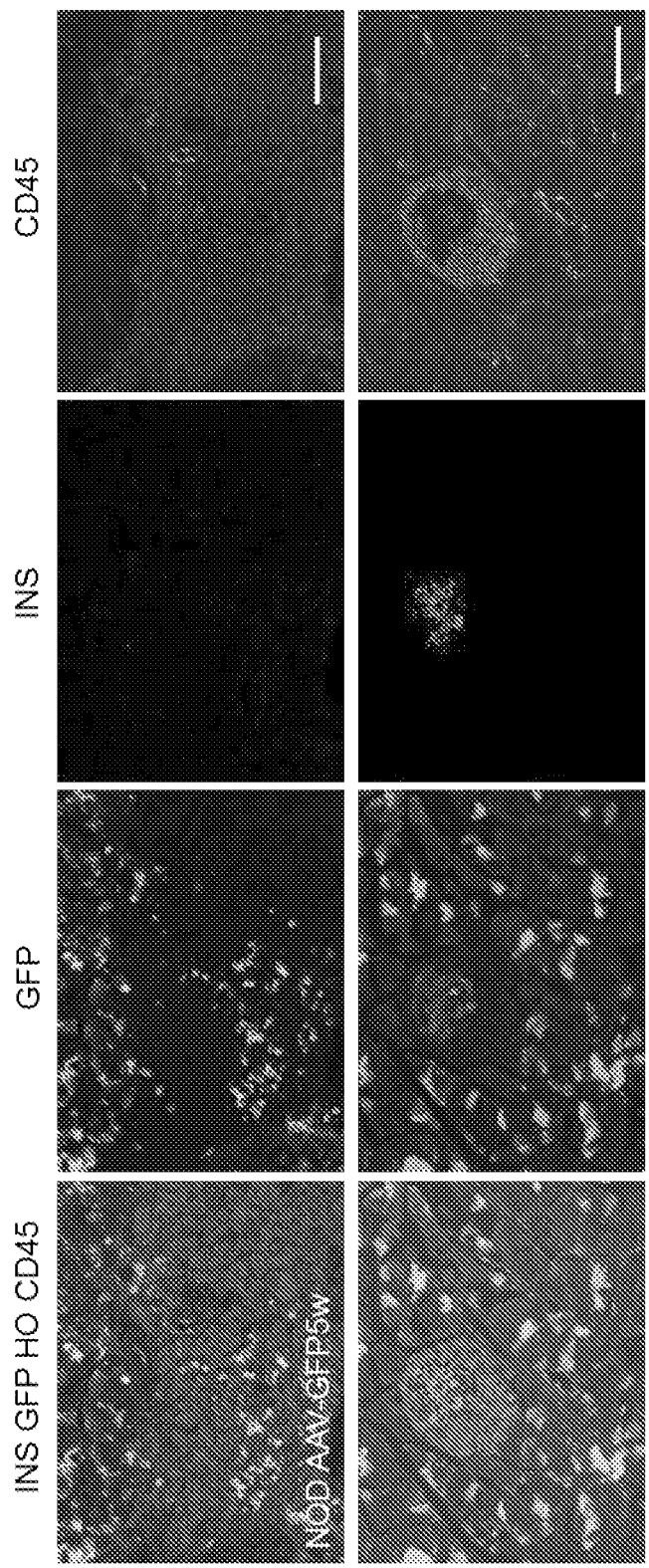
Figure 3C:
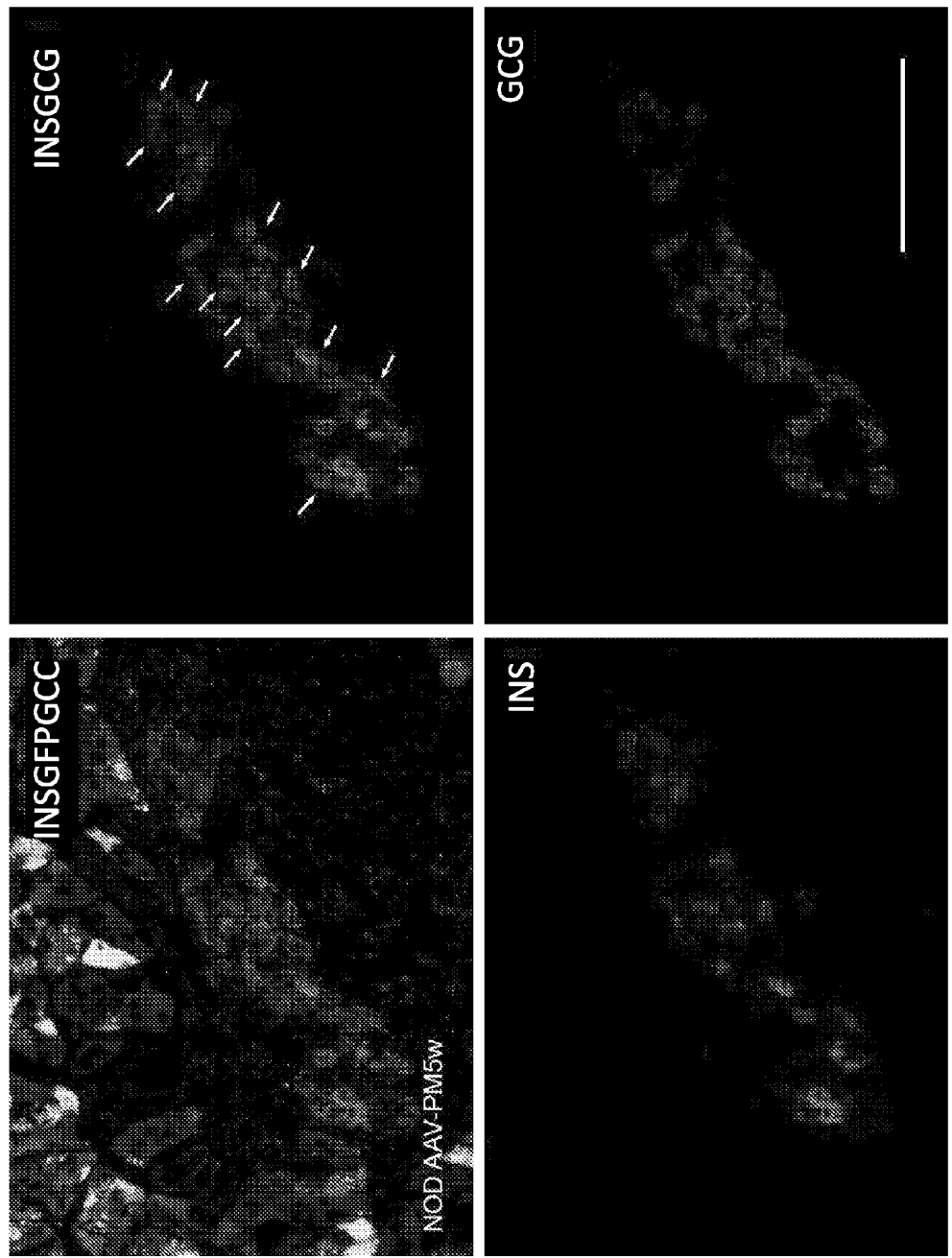
Figure 9A:
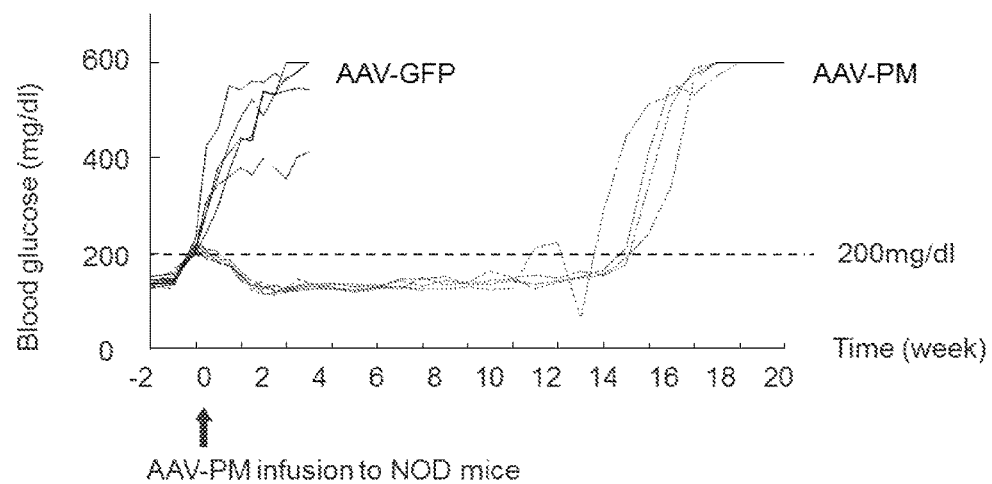
FIGS. 9A-9B: Intraductal infusion of AAV-PM reversed hyperglycemia in NOD mice. (A) Glucose curves for individual mice in FIG. 3A. (B) Delayed intraductal infusion of AAV-PM is less effective in rescuing blood glucose in NOD mice. When the viral infusion was delayed until the blood glucose of female NOD mice surpassed 350 mg/dl, blood glucose levels were normalized in 3 of 7 mice infused with AAV-PM (individual mouse represented by each curve), again for 3-4 months, but in none of the AAV-GFP controls.
Figure 9B:
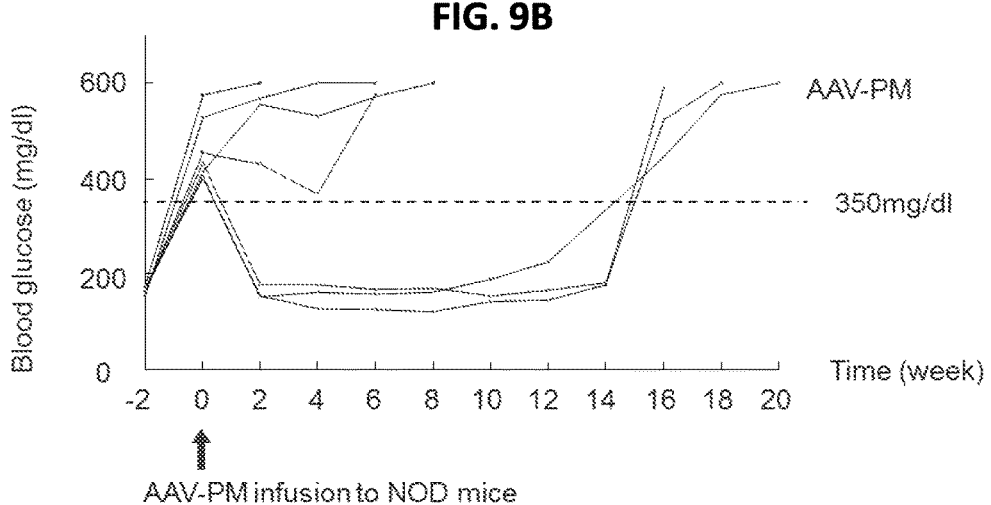

AAV-PM Infusion in Hyperglycemic NOD Mice LED to Prolonged Normalization of Blood Glucose Since the beta cells derived from alpha cells were not transcriptionally identical to preexisting normal beta cells (FIG. 8), it was examined whether they would be recognized by an autoimmune diabetic immune system. Thus, NOD mice were given a single ductal infusion of the PM virus early after the onset of hyperglycemia, when the blood glucose of the mice had surpassed 200 mg/dl. It was found that the glycemia in these mice normalized for about 4 months. The mice receiving control AAV-GFP experienced continuously increasing blood glucose and died within 5 weeks (FIG. 3A, and FIG. 9A). Immunohistological analyses showed that the NOD mice that received AAV-PM had significantly more beta cells (FIG. 3B) as a basis for their normalized blood glucose (FIG. 3A), although the insulitis (based on CD45 staining for immune cells) did not disappear (FIG. 3B). Moreover, 54.5±6.6% of the INS+ cells also expressed GCG (FIG. 3C), suggesting that these insulin-producing cells may be reprogrammed alpha cells. When the intraductal infusion with AAV-PM was instead performed later, after the blood glucose had reached 350 mg/dl, it was found that the blood glucose was normalized in 3 out of 7 mice, and for 3 to 4 months (FIG. 9B).

Example 6

Assessment of the Status of the NOD Immune System Following Viral Therapy

Figure 4B:
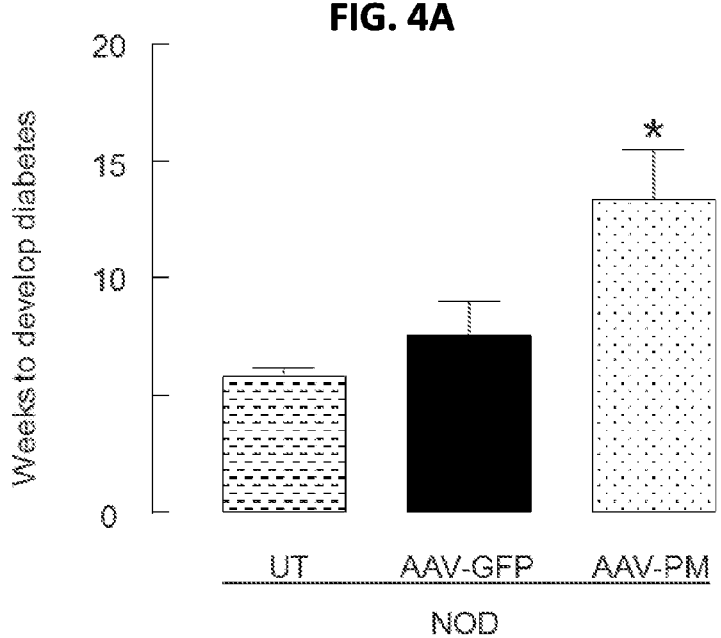
Figure 4B:
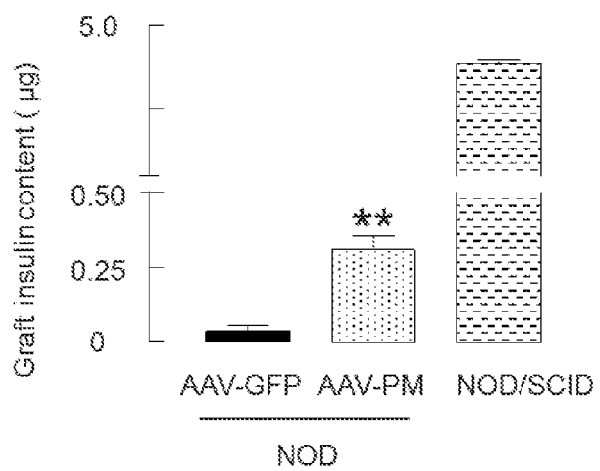
Figure 4D:
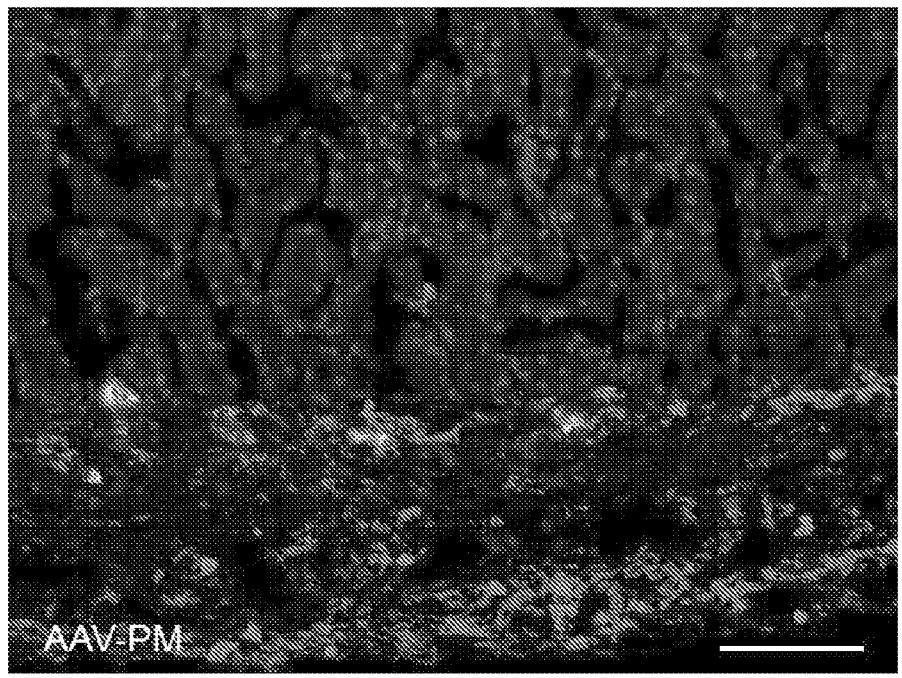
Figure 4D:
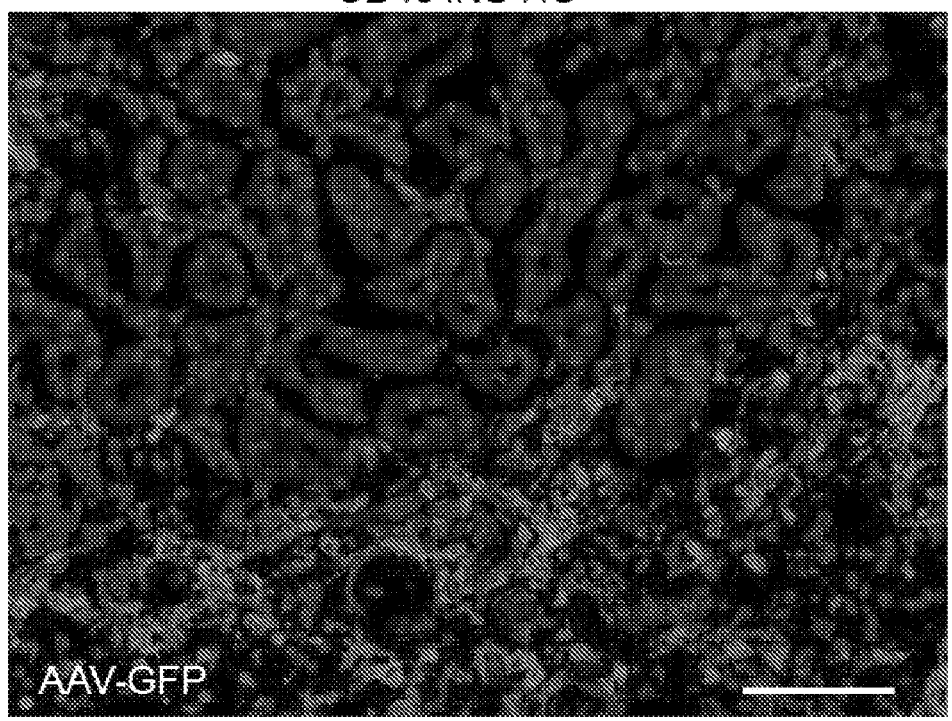

It is well-known that islet transplants into an autoimmune diabetes environment will be quickly destroyed by the "rapid recurrent" form of immune rejection (Ramesh, A., Chhabra, P. & Brayman, K. L. Curr Diabetes Rev 9, 294-311 (2013)), even if the patient is adequately immunosuppressed for a kidney transplant (Vendrame, F. et al. Diabetes 59, 947-957, doi:10.2337/db09-0498 (2010)). One possible explanation for the resistance of the neogenic beta cells to such a rapid recurrent autoimmune rejection is that the pancreatic ductal infusion with AAV-PM could directly alter the autoimmunity in the NOD mouse, resulting in long-term survival of the neogenic beta cells. To examine this possibility, splenocytes were isolated from AAV-PM-treated NOD mice 4 weeks after viral infusion and performed an adoptive transfer into NOD/SCID mice. Splenocytes from untreated hyperglycemic NOD mice (UT) and from AAV-GFP-treated NOD mice were used as controls (FIG. 4A). It was found that the development of diabetes in recipient NOD/SCID mice after delivery of splenocytes from AAV-PM-treated NOD mice was delayed, but still present (FIG. 4A). The timing and cadence of the hyperglycemia onset mirrored that that would be seen if young, naive NOD splenocytes (harvested prior to the onset of hyperglycemia) had been used (Christianson, S. W., Shultz, L. D. & Leiter, E. H. Diabetes 42, 44-55 (1993)). To further test the competence of the NOD autommunity, NOD/SCID mouse islets (300) were transplanted under the kidney capsule of AAV-PM-treated and AAV-GFP-treated NOD mice 4 weeks after viral infusion, as well as into undisturbed NOD/SCID mice as controls (FIG. 4B). Slightly higher graft insulin content was detected in AAV-PM-treated NOD mice (but still much lower than control grafts), compared to that of AAV-GFP-treated NOD mice (FIG. 4C), which was further confirmed by insulin immunohistochemistry of the graft under the kidney capsule (FIG. 4D). Also of importance here is that the presumed reactivation of the autoimmunity, targeted against the transplanted islets, did not lead to an autoimmune attack on the neogenic beta-cells (from alpha-cells) in the pancreas, as the blood glucose remained normal (not shown). These latter data further support that the immune system of the NOD mice is intact, and is behaving as if it were not seeing beta-cell antigen prior to the transplant (i.e. was naive) and thus had a delayed response to the transplanted islets.

Figure 10:
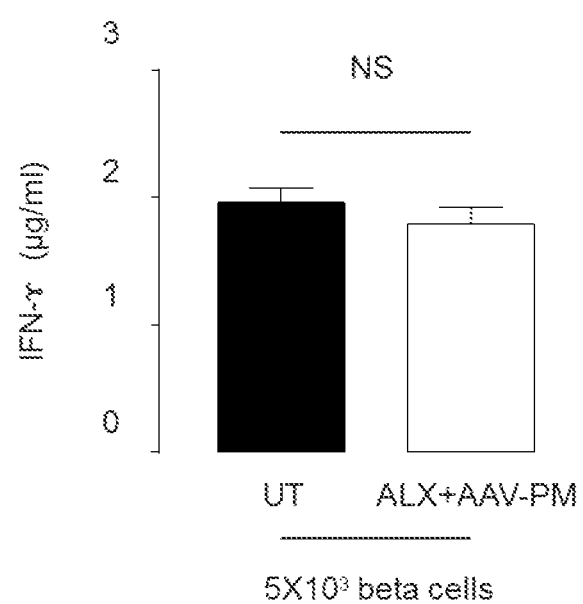
FIG. 10: Neogenic beta cells have immunogenicity comparable to normal beta cells in vitro. The antigenicity of neogenic islet cells from the mice treated with ALX and AAV-PM (2 weeks after viral infusion and with a normalized blood glucose) was measured against control islet cells by diabetogenic BDC2.5 T cell assay. Data are mean IFNγ secretion±SEM of 3 independent experiments, with each group assayed in triplicate.

Another possible explanation for the resistance of the alpha-cell-derived beta-cells to autoimmune attack is that the new beta-cells were sufficiently distinct from normal beta-cells that they were not recognized by the autoimmune cells. Isolated islets from AAV-PM-treated C57BL/6 mice (after ALX-induced beta-cell ablation) were placed in vitro in a T-cell killing assay. Diabetogenic BDC2.5 T-cells (Piganelli, J. D. et al. Diabetes 51, 347-355 (2002); Haskins, K., Portas, M., Bergman, B., Lafferty, K. & Bradley, B. Proc Natl Acad Sci USA 86, 8000-8004 (1989)) showed a reactivity against these islets (comprised of reprogrammed beta-cells) that was similar to the T-cell reactivity against normal islets (FIG. 10). Thus, it appears that simple phenotypic differences alone between reprogrammed beta-cells and normal cells cannot explain the lack of an autoimmune attack.

Example 7

Figure 5A:
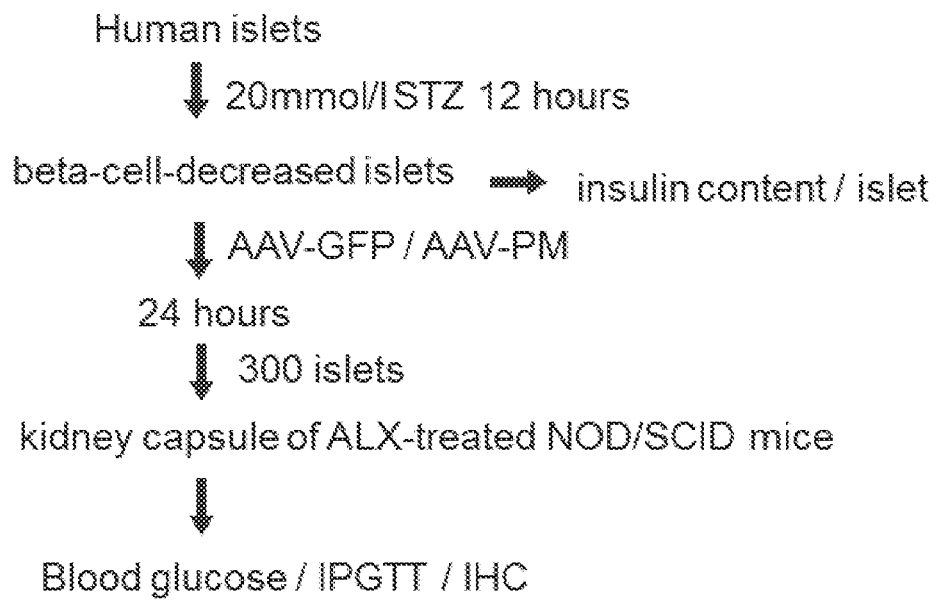
Figure 5B:
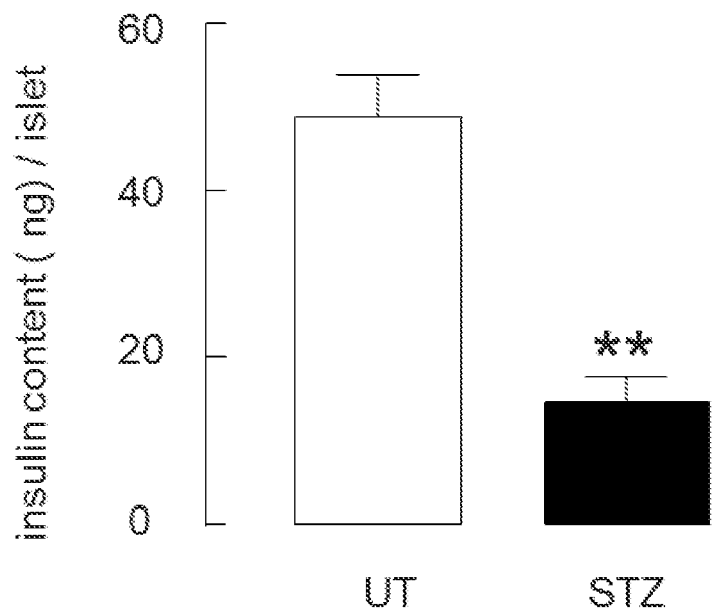
Figure 5E:
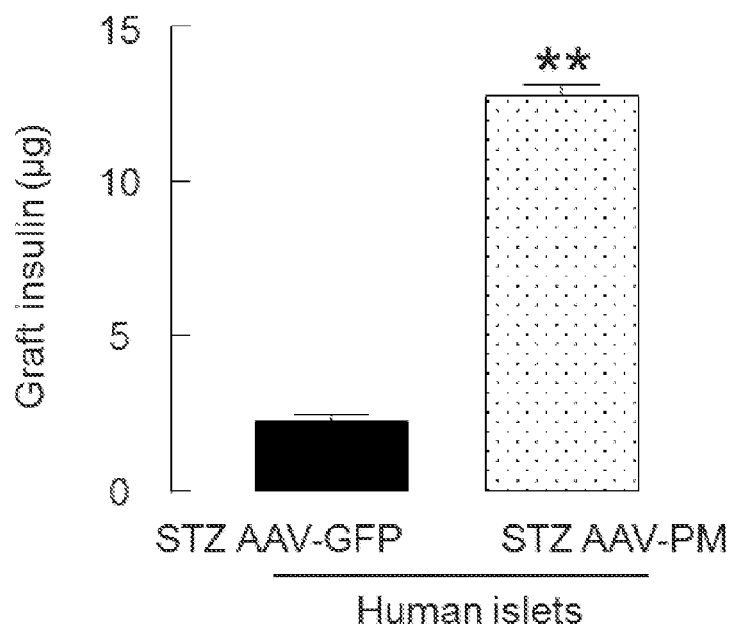
Figure 5F:
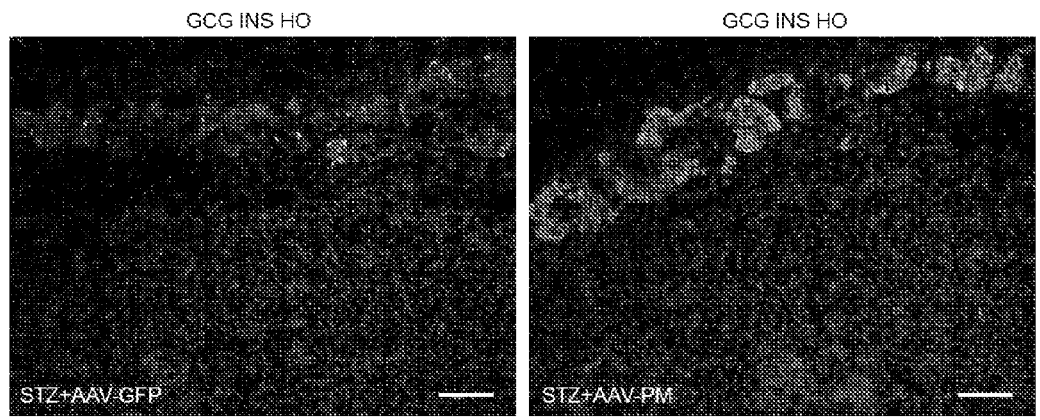
Figure 6A:
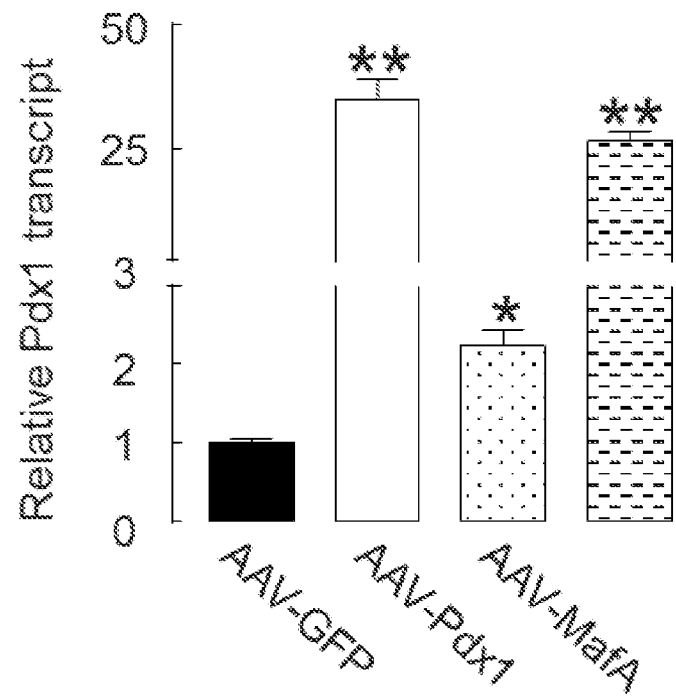
Figure 6B:
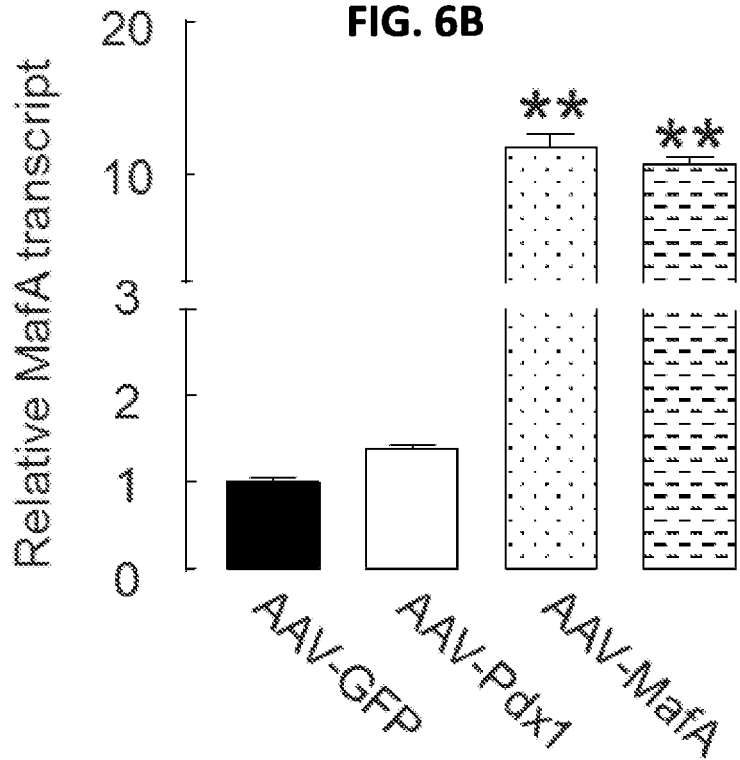
Figure 6E:
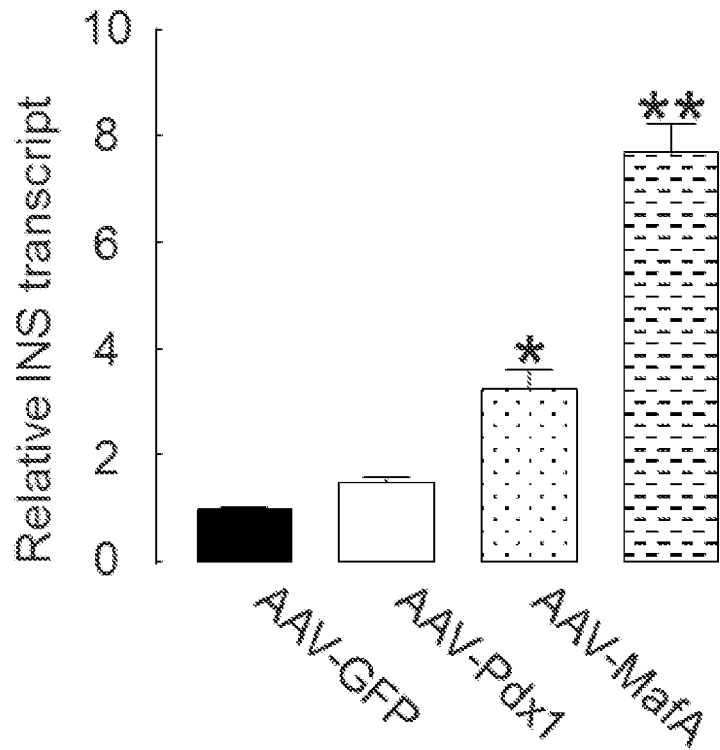
Figure 6F:
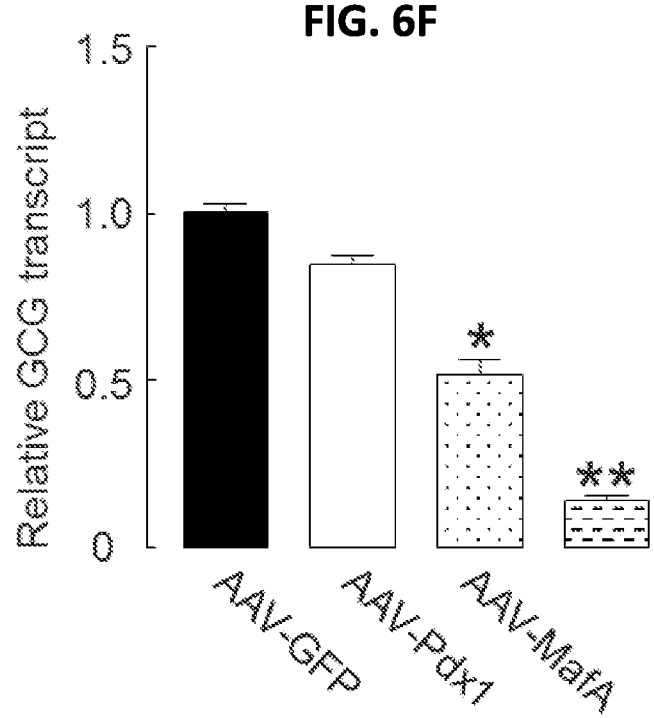
Figure 6G:
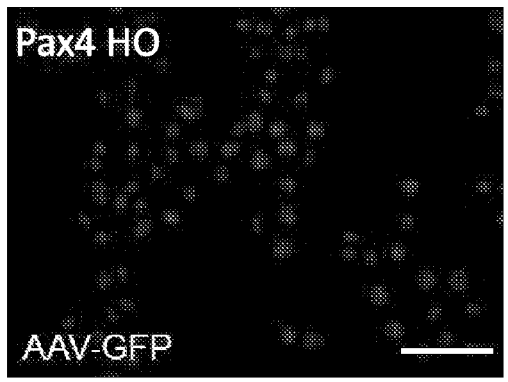
Figure 6G:
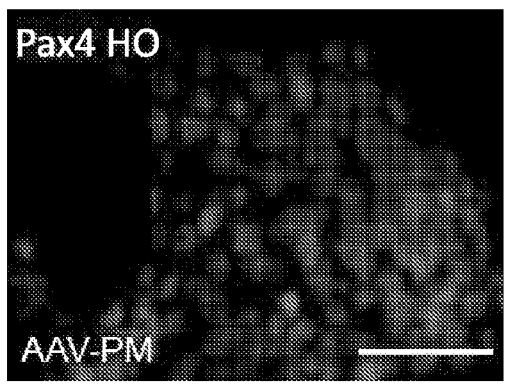
Figure 6H:
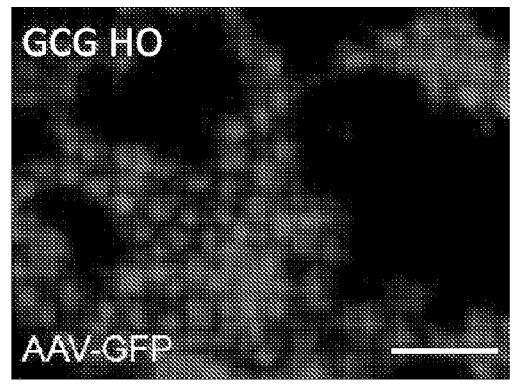
Figure 6H:
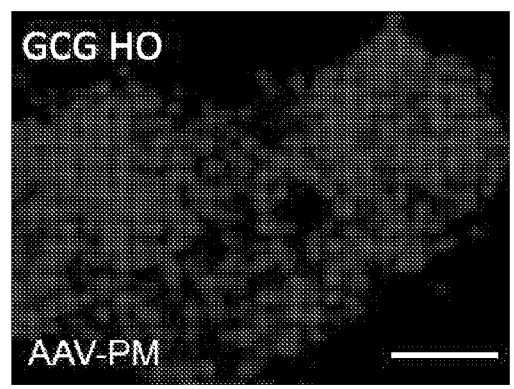
Figure 6I:
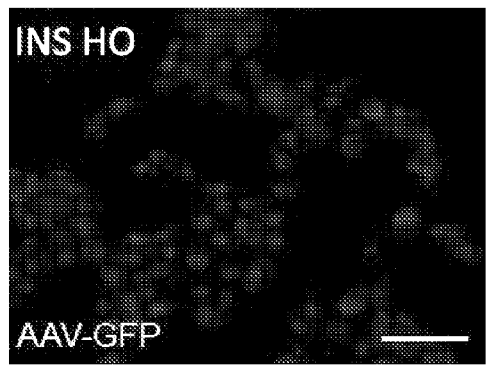
Figure 6I:
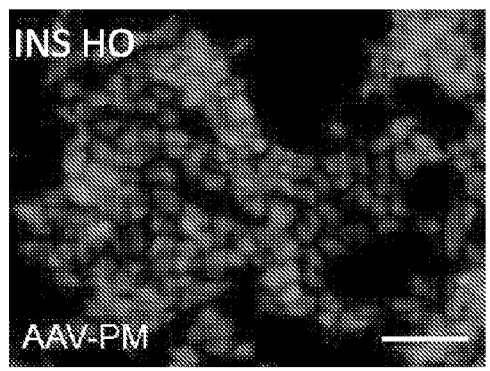

AAV-PM Induced the Generation of Functional Beta Cells from Alpha Cells in Human Islets Based on data from these mouse studies, it was tested whether human alpha cells may be reprogrammed into functional beta cells through a similar strategy. Human islets are resistant to ALX, but high-dose STZ has been reported to ablate a large proportion of human beta cells in vitro[53]. Here, human islets were treated with 20 mmol/l STZ for 12 hours to destroy beta cells, after which the islets were treated in vitro with either AAV-PM or AAV-GFP for 24 hours to trigger alpha-to-beta cell conversion, and then transplanted into ALX-treated hyperglycemic NOD/SCID mice (FIG. 5A). The beta-cell-toxic effect of STZ was confirmed by histology (not shown) and by examining insulin content per islet (FIG. 5B). It was found that one week after transplantation, the ALX-treated NOD/SCID mice that received human islets treated with STZ and AAV-PM had significantly lower blood glucose levels (FIG. 5C), and significantly better glucose tolerance curves, compared to mice transplanted with STZ and AAV-GFP-treated human islets (FIG. 5D). A significantly higher insulin content was detected in the graft of AAV-PM-treated human islets compared to the graft of AAV-GFP-treated human islets (FIG. 5E), which was further confirmed by immunohistochemistry (FIG. 5F). These data suggest that AAV-PM induced the generation of functional beta cells from alpha cells in human islets.

Overexpression of the transcription factor Pax4 in pancreatic progenitors (Collombat, P. et al. Cell 138, 449-462, (2009)), or Pdx1 in newly-formed alpha cells (Yang, et al., Genes Dev 25, 1680-1685, (2011)), may result in a conversion from an alpha cell phenotype to a beta-like cell phenotype, a phenomenon further supported by epigenetic analysis (Bramswig, N. C. et al. J Clin Invest 123, 1275-1284, (2013)). However, this phenomenon seems unlikely to occur in the fully-developed alpha cells in adults (Yang, Y. P. et al., Genes Dev 25, 1680 1685, (2011)), except perhaps in the event of a severe beta-cell loss (Thorel, F. et al. Nature 464, 1149-1154, doi:nature08894 [pii] 10.1038/nature08894 (2010)).

In the experiments disclosed herein, a strong induction of insulin as well as a significant suppression of glucagon was observed in an AAV-PM-treated alpha cell line. Although the insulin upregulation was not dramatic, it is possible that this transformed cell line may be less able to undergo such transdifferentiation, compared to primary alpha cells. However, the in vitro data suggested that a reprogramming event was occurring, since AAV-PM not only induced a shift in hormone expression, but also induced expression of Ngn3 (Zhou et al., Nature 455, 627-632, (2008)) and Pax4 (Collombat, P. et al. Cell 138, 449-462, (2009)) in the aTC cells, two transcription factors that have been shown to trigger beta-cell neogenesis from non-beta cells. Moreover, a significantly lower potential was observed for AAV-Pdx1 alone, compared to AAV-PM, to trigger alpha-to-beta cell conversion (Yang, Y. P., et al., Genes Dev 25, 1680-1685, (2011)).

PM overexpression was subsequently shown to correct hyperglycemia in both ALX-induced diabetes and in autoimmune diabetic NOD mice, suggesting that a true beta cell reprogramming was occurring, rather than simply activation of the insulin promoter and suppression of the glucagon promoter in alpha cells.

In the experiments disclosed herein, GCG-Cre; R26R$^{Tomato}$ reporter mice were used to lineage-trace alpha cells. Although this transgenic GCG promoter that drives Cre is not strong (Herrera, P. L. Development 127, 2317-2322 (2000); Shiota, C. et al. Am J Physiol Endocrinol Metab 305, E1030-1040, (2013)), the highly sensitive tomato reporter allowed for more than 70% of the GCG-lineage cells to be successfully labeled. In the control diabetic AAV-GFP-infused mice, very few insulin-positive cells were detected, and none of them were tagged with tomato red, suggesting that neither the hyperglycemia, nor the viral infection alone, without overexpression of Pdx1 and MafA in target cells, is sufficient to trigger alpha-to-beta cell conversion. Of note, some of the duct cells and acinar cells were also found to be tagged with tomato, suggesting that the glucagon promoter in duct or acinar cells may be activated by overexpression of Pdx1 and MafA. However, these tomato-labeled exocrine cells did not stain positive for insulin, suggesting that they did not convert into insulin-producing cells.

Zhou et al. found conversion of acinar cells into insulin-producing cells by overexpression of Pdx1, Ngn3 and MafA (Zhou, Q., et al., Nature 455, 627-632, (2008)). In the results presented herein, acinar-to-beta cell conversion was not observed when Pdx1 and MafA were overexpressed. Thus, Ngn3 may be indispensable specifically for acinar-to-endocrine conversion, but likely is not required for a reprogramming between different endocrine cell types, as in the conversion from alpha cell to beta cell. However, without being bound by theory, in the beta cells, persistent expression of viral constructs that express Ngn3 can be particularly detrimental for beta cell function.

The prolonged protection (4 months) of the alpha-cell-derived beta cells in NOD mice could theoretically translate to one or two decades in humans. Without being bound by theory, the prolonged protection could stem from two possible mechanisms. The first possibility is that the ductal viral infusion directly altered the autoimmunity, leading to long-term survival of the neogenic beta cells. However, the fact that the control virus infusion had no protective effect argues against this possibility. The delayed, but eventually effective attack on beta-cells in both the adoptive transfer experiments and the NOD/SCID islet transplants, suggested that the autoimmune NOD immune system was intact, but had reverted to a "naive" state in which there was active exposure to antigen. The second possible explanation is that the beta-cells derived from alpha-cells are not recognized by the autoimmune system. By RT-qPCR, it was found that expression levels of beta-cell-specific genes were similar, but not identical to true beta-cells. In addition, we found that diabetogenic immune cells rapidly recognized and destroyed the beta-cells derived from alpha-cells in vitro. Thus, it may be that these new beta-cell-like cells must be localized to the islet microenvironment in order to avoid the rapid recurrent autoimmune attack. If so, such a conclusion would have important ramifications for any future clinical strategy to deliver exogenous beta-cells to T1D. The induction of endogenous beta-cell neogenesis in situ in the islet locale may be critically necessary for effective treatment of T1D. In addition, the delivery of gene therapeutic virus through the pancreatic duct can be used in humans, since such pancreatic injections are routinely performed in humans through a non-surgical procedure known as endoscopic retrograde cholangiopancreatography (ERCP).

Example 8

Glucagon Promoter Analysis

The activity of the glucagon promoter was studied in vivo, in order to improve the alpha-to-beta transdifferentiation system by switching from a CMV global promoter to an alpha cell specific glucagon promoter in an AAV construct. In order to optimize the glucagon promoter, we assessed the effectiveness and specificity of a 0.5 KB promoter (SEQ ID NO: 1) and 1.2 KB promoter (SEQ ID NO: 2), based on upstream were used in transgenic mice. We focused on both mouse and human sequences (see SEQ ID NOs: 1-3).

The AV virus preparation is a unique approach (see also Guo, et. al., Lab Invest. 2013 November; 93(11):1241-53; Guo et al., Bioengineered. 2013 March-April; 4(2):103-6). It entails a simplified process that allows virus preparation fairly quickly and has been used by others successfully as well. In addition, a 2A linker was added this construct to allow a bicistronic message for the two transcription factor cDNA's within one virus, rather than having the complexity and difficulty of having two different viruses.

Figure 11:
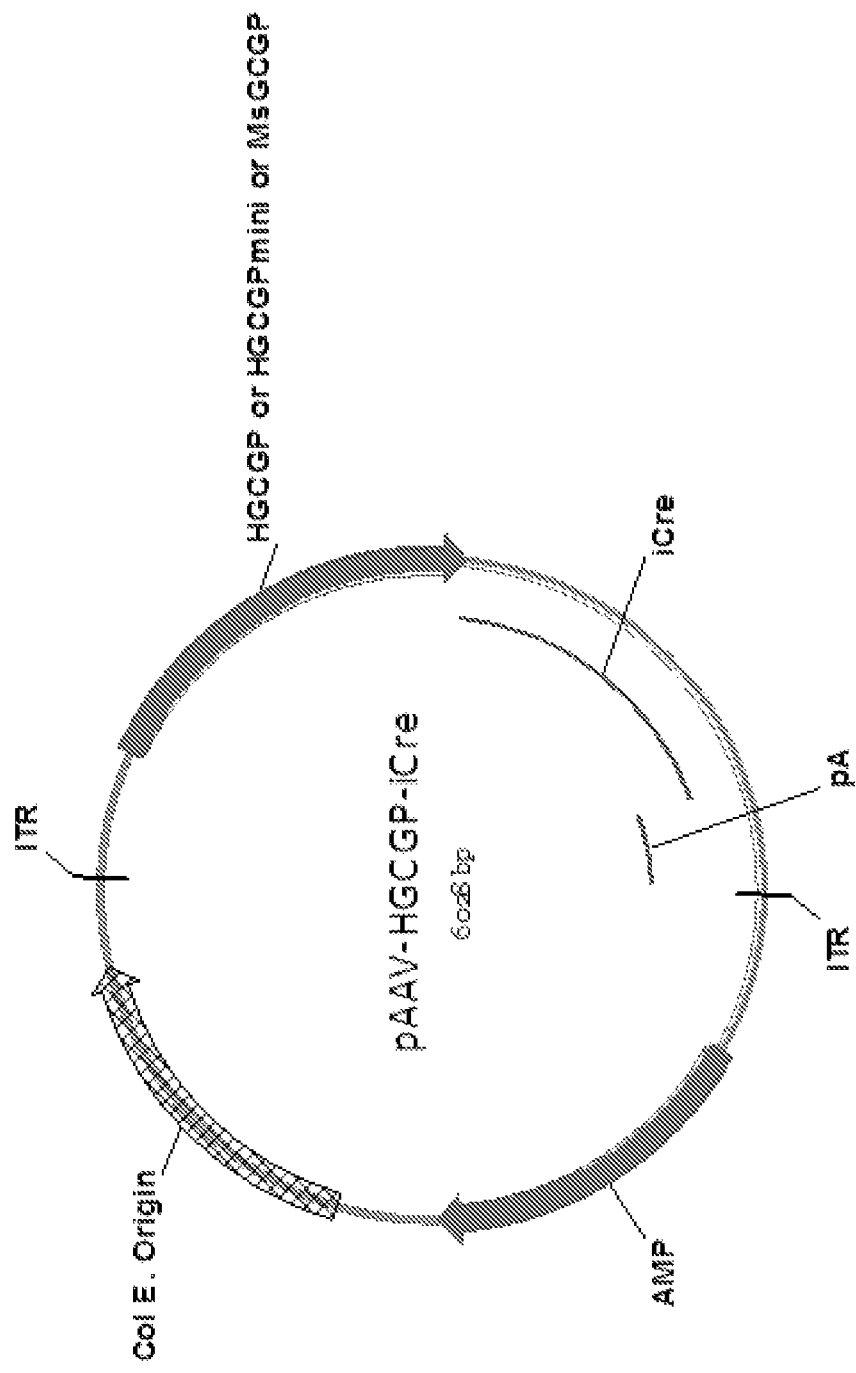
FIG. 11: Plasmid map of the AAV construct used for glucagon promoter driving cre expression.
Figure 12A:
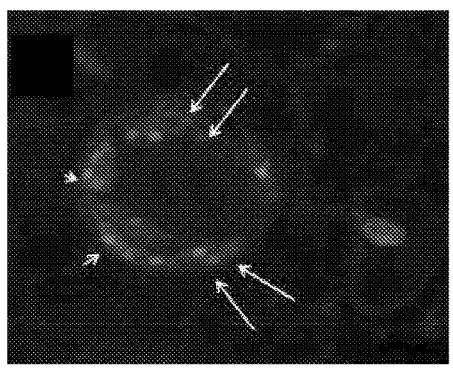
FIGS. 12A-12F: A shorter glucagon promoter sequence surprisingly yields better efficiency and specificity of expression in alpha cells. Panels A and B show a mouse pancreatic islet after infusion of an AAV virus carrying a 1.2 kb glucagon promoter driving cre expression into a tomato red cre-reporter mouse. Only a few alpha cells (stained for glucagon in the mantle region) are positive for tomato (arrows in A denote examples of glucagon-positive/tomato-negative levels, and arrowheads denote glucagon-positive/tomato-positive cells). Several insulin-positive cells (stained cells in the central region in B) are tomato-positive as well (arrows in B). (C-F) In contrast, a similar islet in a cre reporter mouse, but after infusion with a short 0.5 kb glucagon promoter shows that almost every glucagon cell (glucagon staining in panel D) is also stained with tomato (panel C). Few if any insulin-positive cells are tomato labeled (insulin staining in panel E). The merge of all three stains is shown in F).
Figure 12B:
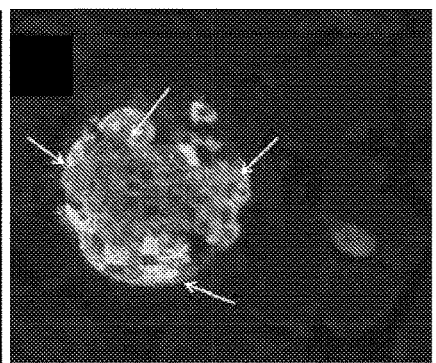
Figures 12C, 12D:
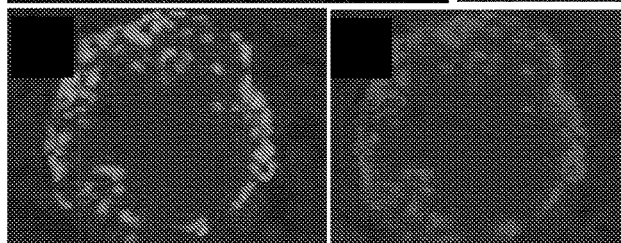
Figures 12E, 12F:
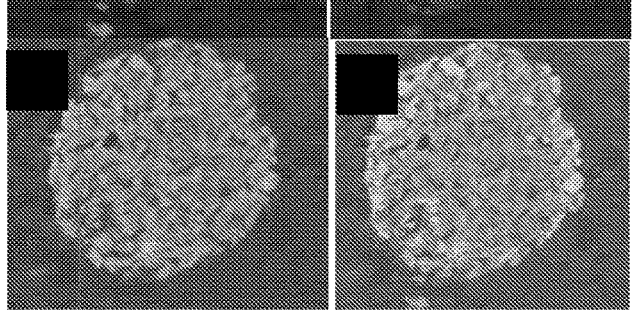

The promoters were ligated into the AAV vector construct (FIG. 11) and initially tested for viability and function in both HEK cells as well as mouse alpha TC cell lines. All of the plasmids and viruses functioned well in vitro. The AAV were then administered intraductal in vivo delivery system in a Cre reporter mouse where the different test glucagon promoters had been inserted in front of a Cre recombinase cDNA. After performing this ductal infusion, the shorter sequence surprisingly led to a more robust and more specific expression in alpha cells (FIG. 12). Surprisingly, the longer sequence had a weaker penetrance of labeling of alpha cells and also was present in non-alpha cells, especially beta cells, thus implying that the shorter sequence provides an unexpectedly superior result, and can be used for our in vivo transdifferentiation.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of producing pancreatic beta cells in a subject, comprising
administering to the subject a vector comprising a glucagon promoter operably linked to a nucleic acid sequence encoding heterologous Pancreas duodenal homeobox protein (Pdx) 1 and a nucleic acid sequence encoding Musculoaponeurotic fibrosarcoma oncogene homolog A (MafA), wherein the vector does not encode Neurogenin 3 (Ngn3), wherein the subject is not administered any other nucleic acid encoding Ngn3, wherein the glucagon promoter a) consists of the nucleic acid sequence of SEQ ID NO: 1, or b) comprises the nucleic acid sequence of SEQ ID NO: 3, and wherein the vector is administered intraductally into a pancreatic duct of the subject,
thereby inducing alpha cells to transform into pancreatic beta cells in the subject.

2. The method of claim 1, wherein the vector is an adenovirus vector or an adeno-associated virus vector.

3. The method of claim 2, wherein the vector is an adeno-associated virus vector, and wherein the adeno-associated virus vector is an adeno-associated virus 8 vector.

4. The method of claim 2, wherein the vector is an adeno-associated virus vector.

5. The method of claim 1, wherein the glucagon promoter consists of the nucleic acid sequence of SEQ ID NO: 1.

6. The method of claim 1, wherein the glucagon promoter comprises the nucleic acid sequence of SEQ ID NO: 3.

7. The method of claim 4, wherein the nucleic acid sequence encoding Pdx1 and the nucleic acid sequence encoding MafA are linked using a connector.

8. The method of claim 7, wherein the connector is a 2A connector.

9. The method of claim 2, wherein intraductally administering comprises the use of endoscopic retrograde cholangiopancreatography (ERCP).

10. The method of claim 2, wherein the subject is not administered an immunosuppressive agent.

11. The method of claim 1, wherein the subject is a human.

12. The method of claim 1, wherein the subject has type I diabetes.

13. A composition comprising:
a) an adeno-associated virus vector comprising a glucagon promoter operably linked to a nucleic acid sequence encoding Pdx1 and a nucleic acid sequence encoding MafA, wherein the vector does not encode Neurogenin 3 (Ngn3), and wherein the glucagon promoter a) consists of the nucleic acid sequence of SEQ ID NO: 1, or b) comprises the nucleic acid sequence of SEQ ID NO: 3;
b) a buffer; and
c) a contrast dye for endoscopic retrograde cholangiopancreatography.

14. The composition of claim 13, wherein the composition does not comprise a nucleic acid encoding Ngn3 or Ngn3 polypeptide.

15. The composition of claim 13, wherein the glucagon promoter comprises the nucleic acid sequence set forth as SEQ ID NO: 3.

16. The composition of claim 13, wherein the contrast dye is a low-osmolar low-viscosity non-ionic dye, a low-viscosity high-osmolar dye, or a dissociable high-viscosity dye.

17. The composition of claim 16, wherein the contrast dye is Iopromid, Ioglicinate, or Ioxaglinate.

18. The composition of claim 13, wherein the adeno-associated virus vector is an adeno-associated virus 8 vector.

19. The composition of claim 13, wherein the nucleic acid sequence encoding Pdx1 and the nucleic acid sequence encoding MafA are linked using a connector.

20. The composition of claim 19, wherein the connector is a 2A connector.

21. The composition of claim 13, wherein the adeno-associated virus vector comprises a nucleic acid sequence encoding a label.

22. The composition of claim 13, wherein the glucagon promoter consists of the nucleic acid sequence set forth as SEQ ID NO: 1.

\* \* \* \* \*